United States Patent
Vukasinovic

(10) Patent No.: US 9,334,473 B2
(45) Date of Patent: May 10, 2016

(54) THREE DIMENSIONAL CELL CULTURE COMPOSITIONS AND METHODS OF USE

(71) Applicant: Jelena Vukasinovic, Atlanta, GA (US)

(72) Inventor: Jelena Vukasinovic, Atlanta, GA (US)

(73) Assignee: Jelena Vukasinovic, Atlanta, GA (US)

( * ) Notice: Subject to any disclaimer, the term of this patent is extended or adjusted under 35 U.S.C. 154(b) by 48 days.

(21) Appl. No.: 13/962,403

(22) Filed: Aug. 8, 2013

(65) Prior Publication Data

US 2014/0051168 A1 Feb. 20, 2014

Related U.S. Application Data

(60) Provisional application No. 61/684,200, filed on Aug. 17, 2012.

(51) Int. Cl.
*C12N 5/00* (2006.01)

(52) U.S. Cl.
CPC ............ *C12N 5/0062* (2013.01); *C12N 5/0068* (2013.01); *C12N 2533/12* (2013.01); *C12N 2533/30* (2013.01); *C12N 2533/90* (2013.01)

(58) Field of Classification Search
CPC ............... C12N 5/0062; C12N 5/0068; C12N 2533/90; C12N 2533/30; C12N 2533/12
USPC .................................................. 435/395, 397
See application file for complete search history.

(56) References Cited

U.S. PATENT DOCUMENTS 5,266,476 A * 11/1993 Sussman et al. ............... 435/399
6,471,993 B1 * 10/2002 Shastri et al. .................. 424/486
7,767,446 B2    8/2010 Robbins et al.

OTHER PUBLICATIONS

Karageorgiou et al. (2005). Porosity of 3D biomaterial scaffolds and osteogenesis. Biomaterials, v26, p. 574-5491.*
Liu et al (2009). Bioreactive borosilicate glass scaffolds: improvement on the strength of glass-based scaffolds for tissue engineeriung. J Mater Sci: Mater Med, v20, p. 365-372.*
Howe (2006). Coated Glass and Vicryl Microfibers as Artificial Axons. Cells, Tissues, and Organs, v183(4), p. 180-194.*
Oh et al. (2003). Fabrication and characterization of hydrophillic poly(lactic-co-glycolic acid)/poly(vinyl alcohol) blend cell scaffolds by melt-molding particulate-leaching method. Biomaterials, v24, p. 4011-4021.*
DeLong et al. (2005). Covalently immboilized gradients of bFGF on hydrogel scaffolds for directed cell migration. Biomaterials, v26, p. 3227-3234.*
Tanriverdi et al. (2007). Electrospinning and characterization of alumina borosilicate ceramic nanofibres. Materials Science-Poland, v25(4), p. 957-968.*
Singh et al. (2008). Strategies and applications for incorporating physical and chemical signal gradients in tissue engineering. Tissue Engineering Part B, v14(4), p. 341-366.*
Iida (2004). Matrigel Invasion Assays. online publication at http://www.iprotocol.com.*
Nazhat et al. (2006). Controlled Microchannelling in Dense Collagen Scaffolds by Soluble Phosphate Glass Fibers. Biomacromolecules, v8, p. 543-551.*
Hench (2006). The story of Bioglass. J Mater Sci: Mater Med, v17, p. 967-978.*
Comley, D.J., 2010. 3D cell culture easier said than done. Drug Discovery World. 11(3): 25-41.
Cullen, D. K., Vukasinovic, J., Glezer, A., LaPlaca M.C. 2007. Microfluidic engineered high cell density three-dimensional neural cultures. J Neural Eng 4(2):159-172.
Fait, E., Malkusch, W., Gnoth, S.-H. et al. 1998. Microvascular patterns of the human large intestine: morphometric studies of vascular parameters in corrosion casts. Scanning Microscopy 12(4):641-651.
Fissell, W.H, Hofmann, C.L., Ferrell, N. et al. 2009. Solute partitioning and filtration by extracellular matrices. Am J Physiol Renal Physiol 297(4):F1092-F1100.
Marasanapalle, V., Li, X., Polin, L., et al. 2006. Novel in vitro model barriers for evaluation of the permeability of antitumor compounds, thioxanthones. Invest New Drugs 24(2):111-116.
Martini, J. and Honig, C.R. 1969. Direct measurement of intercapillary distance in beating rat in situ under various conditions of O2 supply. Microvasc Res. 1(3):244-256.
McCarty, W.J. and Johnson, M. 2007. The hydraulic conductivity of matrigel. Biorheology 44(5-6):303-317.
Rambani, K., Vukasinovic, J., Glezer, A. et al. 2009. Culturing thick brain slices: an interstitial 3D microperfusion system for enhanced viability. J Neurosci Methods 180(2):243-254.
Spencer, B.J. and Verma, I.M. 2007. Targeted delivery of proteins across the blood-brain barrier. Proc Natl Acad Sci U S A. 104(18):7594-7599.
Swartz, M. A., and Fleury, M.E. 2007. Interstitial flow and its effects in soft tissues. Annu. Rev. Biomed. Eng. 9: 229-256.
Sailon, A. M., Allori, A. C., Davidson, E. H., Reformat, D. D., Allen, R. J., & Warren, S. M. (2009). A novel flow-perfusion bioreactor supports 3D dynamic cell culture. BioMed Research International, 2009.
SIGMA, "ECM gel from Engelbreth-Holm-Swarm mouse sarcoma", ProductInformation, Catalog No. E1270, Published Oct. 2006.

(Continued)

*Primary Examiner* — Scott Long
*Assistant Examiner* — Sean C Barron
(74) *Attorney, Agent, or Firm* — Meunier Carlin & Curfman LLC

(57) ABSTRACT

Described herein is a three-dimensional cell culture scaffold composition comprising an absorbent rigid (AR) component, and in some embodiments, further comprises a gel component. The absorbent rigid component preferably comprises a glass fiber material. It is a surprising finding of the present invention that an AR component having a void volume of between approximately 70% and 95% results in a three-dimensional cell culture composition that allows for robust, high-throughput screening and high-content screening accessible tissue models with preserved cell morphology, heterogeneity of cell types and cell populations, extracellular matrix constituents, functional cell-cell and cell-extracellular matrix interactions and signaling with sufficient specificities to tissue physiology and pathology.

6 Claims, 28 Drawing Sheets

(56) References Cited

OTHER PUBLICATIONS

Deepa et al., Composition of Perineuronal Net Extracellular Matrix in Rat Brain, Journal of Biological Chemistry, vol. 281, No. 26, pp. 17789-17800 (2006).

Nguyen et al., Characterization of Type I and IV Collagens by Raman Microspectroscopy: Identification of Spectral Markers of the Dermo-Epidermal Junction, Spectroscopy: An International Journal, vol. 27, Issue 5-6, pp. 421-427 (2012).

Sykova et al., Diffusion in Brain Extracellular Space, Physiol. Rev., vol. 88, pp. 1277-1340 (2008).

* cited by examiner

A

B

C

D

E

F

THREE DIMENSIONAL CELL CULTURE COMPOSITIONS AND METHODS OF USE

CROSS REFERENCE TO RELATED APPLICATIONS

This application claims the priority benefit of U.S. Provisional Patent Application Ser. No. 61/684,200 filed on Aug. 17, 2012.

STATEMENT REGARDING FEDERALLY SPONSORED RESEARCH OR DEVELOPMENT

This invention was made with government support under 1 R43 NS065543 and 5 R43 NS065543 awarded by the National Institutes of Health. The U.S. government has certain rights in this invention.

BACKGROUND OF THE INVENTION

To reduce high attrition rates and accelerate discovery and development timelines, the pharmaceutical industry seeks in vitro alternatives to interrogate drug candidates prior to animal, humanized animal and human studies. Enormous cost, ethical concerns and increased pressure from regulatory agencies to replace, reduce and refine animal use in drug discovery and toxicity testing all drive demand for cell-based models that can be used for in vitro screening to triage toxic and ineffective leads earlier, prior to in vivo studies. However, it has been difficult finding a cell-based model that not only mimics the function of living tissues but that can also be appropriately analyzed in the drug screening context.

Cost-efficient interrogation of drug candidates often requires high throughput methodology. Cell monolayers, or a layer of cells growing, for example, in a petri dish, were commonly used in cell-based assays and were optimal for high throughput screening processes. However, it was soon found that cell monolayers had a very low success rate in predicting in vivo therapeutic outcomes of drug candidates.

The poor results obtained with cell monolayers have been attributed to the vast differences in the monolayer cell environment and the in vivo cell environment. Cell morphology, extracellular matrix interactions, three-dimensional organization, oxygen tension and access to both the therapeutics being tested and other extracellular factors all differ greatly between cells found in a monolayer and cells found in vivo.

Recently, three-dimensional (3D) cell cultures have emerged as an alternative to a flat layer of cells as a means to model tissues with improved physiological relevance for biomedical research and in vitro drug testing of all stages. 3D cell cultures are cellular networks in which cells are round and organized in three dimensions, an environment and cell morphology that are more similar to that found in vivo. Examples include three-dimensional cell aggregates such as tumor spheroids, embryoid bodies and hanging drop cell cultures; cultures grown in three-dimensional scaffolds; and the cultures grown in extracellular matrix gels or gels mimicking the extracellular matrix, among others. According to Comley (Comley, D. J., 2010. Drug Discovery World. 11(3): 25-41), the formats that showed the most promise in 3D cell culturing were gel/hydrogel, followed by ECM (extracellular matrix) sheet, aggregates/spheroids, and then collagen tissue constructs. This study was based on industry-wide global market survey results from 78 university/research institute/not-for-profit facilities, 28 biotech companies, 11 others, nine hospitals/clinics, seven pharmaceutical companies, four government/military/defense facilities, two fee-for-service providers, one biomanufacturing/bioprocessing lab, one diagnostics company, and one agrochemical company.

The Comley article describes that most of the prior art advances in 3D cell culture revolved around the use of a hydrogel or collagen scaffold (termed a biomimetic scaffold) (Comley, J., Drug Discovery World, Summer, pp. 25-41, 2010.) Gel/hydrogel based formats have become favored by the industry because they are better able to mimic the cellular environment found in tissues in vivo. When grown in extra-cellular matrices or gels functionalized to mimic extracellular matrix, the cells are round and interact with the other cells and the matrix in a manner that is closer to the in vivo situation. Oxygen tension, extracellular availability of soluble factors, cell adhesion molecules and the stiffness of the extracellular environment can be adjusted by adjusting the gel composition to reflect those in native tissues. Two other platforms for 3D cell culture being pursued by prior art researchers were structural scaffolds and microfluidic devices, structural scaffolds being defined as materials made from the same material as 2D plate surfaces such as polystyrene and having some 3D microstructure.

Despite advances made by many prior art researchers, the Comley article describes that most prior art 3D cell culture applications were riddled with problems and failed to meet the needs of their consumers. The article specifically notes that these prior art compositions and methods provided a "[v]irtual lack of proven automated solutions," and that "all methods need[ed] higher throughput." The study went on to note that there was "poor reproducibility between batches of biometric scaffolds," there was a "limited ability to scale up or down a single 3D format," and that "better visualization [and] wider applicability to HCS [(high content screening)]" was needed.

Low production control, low throughput, difficult handling, and incompatibility with high-throughput screening and high-content screening readouts remain key limitations for widespread adoption of gel-based 3D cell culture models as a mainstream approach in routine screening workflows. The four most significant problems with using gel-based cultures for drug screening are described below.

First, sol-state gels comprising cells are difficult to plate so that characteristic culture dimensions are consistent and reproducible and it is difficult to do so in sufficient throughput needed in pharmaceutical testing. For those gels having a gelling mechanism that depends on temperature, gelling may start during culture dispensing at plating. This produces culture-to-culture variations in culture shape and height for the same volume of dispensed sol-state extracellular matrix (ECM) gel plus cells due to temperature variations during both dispensing and gelling. An example of such gel is BD™ MATRIGEL™.

Second, cellular distribution within the gel is non-uniform in three dimensions and/or difficult to control. This is true for various types of gels and gelling mechanisms including but not limited to thermo-reversible gels (i.e., the BD™ MATRIGEL™), gels requiring physiological temperature to initiate or accelerate polymerization (i.e., Collagen type I), gel precursors which gel by addition of cross-linking agents (i.e., Glycosan HYSTEM™) and those which self-assemble (i.e., BD™ PURAMATRIX™), among others. Regardless of the gelling method, whether mediated by chemical or physical cross-linking, cells settle if gelling is slow. Typical gelling time scale is at the order of tens of minutes, during which time cells may be settling. This leads to non-uniform cell distribution within gel 3D cultures, which is further exacerbated by variations in environmental parameters causing additional culture-to-culture inconsistencies.

Inconsistent culture dimensions and cell density across these dimensions yield culture-to-culture inconsistent supply of nutrients, removal of catabolic waste products and intra-culture concentrations of trophic factors, autocrine and paracrine signaling molecules cells secrete to regulate their environment, growth and many other functions. Some signaling molecules degrade quickly, limiting the scope of their effectiveness to the immediate cell surroundings. Others affect only nearby cells because they are taken up quickly, or because their transport is hindered by the extracellular matrix. For these reasons, inconsistent cultures at plating are more likely to yield inconsistent tissue analogs for drug testing. Variations in cell function and secretion of drug metabolizing enzymes influence pharmacokinetic and pharmacodynamic studies, resulting in potentially less conclusive cellular outcomes and problems with interpretation of results.

Third, gels are flexible and not suitable for vigorous experimentation and routine handling. Even at low throughput levels, the prior art tissue reconstructions are too delicate for routine handling, assaying and screening, especially after days in culture, a period which is required for 3D cell cultures to mature into functional tissue reconstructions for drug testing in the same. During this period in culture, gels may deteriorate before cells secrete and reconstitute their own endogenous matrix support, or gels may become too frail so that a culture disintegrates on routine pipetting. While gels degrade by a variety of mechanisms depending on their chemistry, presence of cells and environment, they typically break down (lose mass or dissolve) by mechanisms that reverse gelling, such as enzymatic or hydrolytic degradation or cell-mediated matrix remodeling and digestion, among other factors.

Fourth, temporal variations in gel composition and its structural integrity contribute to variability in three-dimensional gel-based cell culturing. This variability is present batch-to-batch, and even culture-to-culture, in the same batch owing to susceptibilities to environmental factors that govern gelling and due to matrix remodeling by cells, which is different culture-to-culture due to inadequate control of cell distribution at plating.

Each of these issues likely contributes to the findings of the Comley article relating to the lack of appropriate three-dimensional cell cultures for high-throughput screening and high-content screening applications. Accordingly, what are needed in the art are 3D cell culture compositions and methods of using said compositions to transform inconsistent, low experimental count 3D cultures into consistent and reliable high-throughput screening and high-content screening diagnostic tools. More specifically, what are needed are imaging-accessible 3D cell culture compositions and methods of using the same to reproducibly plate consistent cultures in high-throughput; routinely culture, handle, apply test agents and assay said cultures in high-throughput; and routinely screen in said cultures, days and weeks after culture plating, using standard high-throughput screening and high-content screening tools.

BRIEF DESCRIPTION OF THE DRAWINGS

FIG. 1A shows mechanically dispersed Polyvinyl Alcohol fiber VPB 105-2 prior to wet dispersion. FIG. 1B shows the PVOH fiber slurry in 70% Ethanol after 24-hour wet dispersion and mixing using a magnetic stirrer and periodic vortexing. FIG. 1C shows a hydrophilic and absorbent PVOH rigid absorbent substrate in its dry state following drying and pressing to a desired thickness of 400 µm.

FIG. 8A-8B are 10× (x=1.18 mm, y=0.88 mm) images of cultures, which were cultured for 3 days in uncoated and coated substrates, with spheroids and differentiated 3D cultures of cells, respectively. FIG. 8C-8D are 10× images of cultures cultured in coated substrates, showing 3D cell spheroids and differentiated 3D cultures of cells, respectively, residing on the bottom side of the substrate. FIGS. 8E-8F are 4× (x=3 mm, y=2.25 mm) top and bottom images of uncoated substrate comprising spheroids after 4 days in culture.

FIG. 9 contains fluorescence micrographs of Calcein AM/Hoechst 33342 labeled multipotent stem cells cultured in a pair of overlaid steam autoclaved G041 substrates.

FIG. 10A shows a 1-week culture of neurons and mixed glia in PDL-coated substrate. FIG. 10B shows a 2-week culture of neurons and mixed glia delivered into uncoated substrate in 7.5 mg/ml MATRIGEL™. In FIGS. 10A-10B, cells types were labeled selectively to distinguish them; Calcein Blue AM labeled live cells blue, 5-(and-6)-CFDA was selective for neurons and ALEXA FLUOR™ 568 isolectin GS-IB4 conjugate selective for microglia. FIGS. 10C-10D show cultures of astrocytes and microglia seeded in 3.75 mg/ml MATRIGEL™ into uncoated and PDL-coated substrates, respectively, cultured for 1 day and stained by Calcein AM. FIG. 10E shows astrocytes and microglia seeded in 3.75 mg/ml MATRIGEL™ into uncoated substrate, cultured for 1 week in the same serum-free medium, and then for 3 days without medium but overlaid by another substrate containing substrate-bound and MATRIGEL™-bound serum-free medium. Calcein AM labeling of live cells showed that cells survived.

FIGS. 14A and 14B are 4× images (x=3 mm, y=2.25 mm) after 2 and 7 days in culture, respectively. FIGS. 14C and 14D are 10× (x=1.18 mm, y=0.88 mm) images after 2 and 7 days in culture, respectively. FIGS. 14E and 14F are 4× and 10× images after 24 days in culture, respectively.

FIGS. 15A and 15B are 10× images (x=1.18 mm, y=0.88 mm) of 2×10⁶ cells at seeding after 7 and 24 days in culture, respectively. FIGS. 15C and 15D are 10× images of 10⁶ cells at seeding after 9 and 24 days in culture, respectively. FIGS. 15E and 15F are 10× images of $2.5 \times 10^5$ and $1.25 \times 10^5$ cells at seeding, respectively, imaged after 24 days in culture.

FIGS. 17A, 17C, 17E, and 17G stand for an 4× image (x=3 mm, y=2.25 mm). FIGS. 17B, 17D, 17F, and 17H stand for an 10× image (x=1.18 mm, y=0.88 mm).

FIGS. 18A-18B show cells cultured in PDL-coated substrates after 8 and 30 days in culture, respectively, at 4× (x=3 mm, y=2.25 mm). FIGS. 18C-18D show cells and matrix in PDL-coated substrates after 30 and 56 days in culture, respectively, at 10× (x=1.18 mm, y=0.88 mm). FIGS. 18E-18F show cells and matrix at 10× in Fibronectin-coated substrates after 42 and 56 days in culture, respectively.

FIGS. 19A-19B show cells and matrix after 30 and 56 days in culture, respectively, at 4× (x=3 mm, y=2.25 mm). FIGS. 19C-19D show cells after 42 days in culture in 2 cultures at 10× (x=1.18 mm, y=0.88 mm). FIGS. 19E-19F show cells and matrix at 4× and 10×, respectively, after 56 days in culture.

In FIGS. 20A-20B cells were seeded in a 50 μl drop of cells and MATRIGEL™ delivered to wells of a 12-well plate. The culture looked like a plano-convex lens. FIG. 20A shows cell distribution at culture base and FIG. 20B shows cells distribution in a plane which was about 100 μm above the culture base at 10× (x=1.18 mm, y=0.88 mm). In FIGS. 20C-20D cells were seeded in a 50 μl drop of cells and MATRIGEL™ delivered to steam-autoclaved G041 substrates seated in wells of a 12-well plate. FIG. 20C is the top view of the culture and FIG. 20D is the bottom view of the culture taken after the substrate was flipped to image. FIGS. 20C-20D were taken at 4× (x=3 mm, y=2.25 mm).

FIG. 21 contains images of neural-astrocytic cell cultures in 8 mg/ml MATRIGEL™, their confocal micrographs, and 3D-rendering of said cultures with color coded cell depth. FIGS. 21A, 21D, and 21G refer to culture photographs after 10 days in culture and prior to staining; FIGS. 21B, 21E, and 21H refer to confocal micrograph of the culture with respective index 1; and FIGS. 21C, 21F, and 21I refer to 3D rendering of confocal image stack through the full thickness of the culture of respective index 1. MATRIGEL™ controls (FIGS. 21A-21C) were seeded, cultured, stained and imaged as cultures with FIGS. 21D-21F and FIGS. 21G-21I. Cultures in FIGS. 21D-21F and FIGS. 21G-21I were seeded, cultured, stained and imaged as cultures shown in FIG. 11.

FIG. 22A is a photograph of the plate right after delivery of ALAMARBLUE™. FIG. 22B shows the plate after 5 hours incubation in ALAMARBLUE™ solutions (the in situ ALAMARBLUE™ assay). FIG. 22C shows a 48-well plate into which the ALAMARBLUE™ solutions were correspondingly transferred to (the post-transfer assay).

DETAILED DESCRIPTION OF THE INVENTION

Figure 1A:
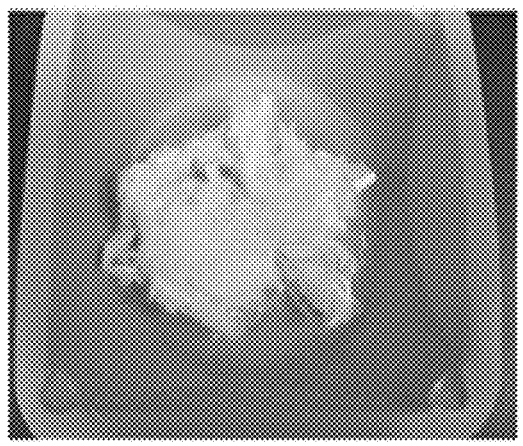
FIGS. 1A-1C are photographs showing several steps in the fabrication of rigid absorbent substrate using a wet laid process.

Described herein is a three-dimensional cell culture scaffold composition comprising an absorbent rigid component, and in some embodiments, further comprises a gel component. The absorbent rigid component preferably comprises a glass fiber material. In some embodiments, the absorbent rigid component comprises glass fibers and absorbent fibers. In other embodiments, the absorbent rigid component comprises glass fibers having an absorbent coating. The scaffold composition is configured such that the absorbent rigid component has a dry-state, interior, non-rigid and non-absorbent volume (hereinafter referred to as a "void volume") of between approximately 70% and 95%. In some embodiments, this void volume of the scaffold composition comprises a gel and one or more cells.

It is a surprising finding of the present invention that an absorbent rigid (AR) component having a void volume of between approximately 70% and 95% results in a 3D cell culture composition that allows for robust, high-throughput screening and high-content screening accessible tissue models with preserved cell morphology, heterogeneity of cell types and cell populations, extracellular matrix (ECM) constituents, functional cell-cell and cell-ECM interactions and signaling with sufficient specificities to normal tissue physiology and pathology. In some embodiments, the void volume is between approximately 75% and 95%, 80% and 95%, 85% and 95%, or 90% and 95% of a total AR dry-state volume. In a preferred embodiment, the void volume is approximately 90% of a total AR dry-state volume.

The AR component of the present invention preferably comprises a rigid material having an optical transmission of at least 70% at a normal incidence for up to 0.5 mm-thick flat material sample in the range of wavelengths between approximately 400 nm and 2 µm, and still more preferably, an optical transmission of at least 80% at a normal incidence for 0.5 mm-thick flat material sample in the range of wavelengths between 350 nm and 2 µm. In one embodiment, the AR component comprises a rigid fiber material, and preferably a glass fiber. The glass fiber may be a borosilicate glass fiber selected from the group of A, C, D, E, S and R borosilicate glass fibers. The glass fiber is preferably between approximately 3 and 30 µm in diameter, more preferably between 5-15 µm in diameter. In some embodiments, the glass fiber is approximately 3, 4, 5, 6, 7, 8, 9, 10, 11, 12, 13, 14, 15, 16, 17, 18, 19, 20, 21, 22, 23, 24, 25, 26, 27, 28, 29 or 30 µm in diameter.

In some embodiments, the absorbent rigid component comprises a mixture of glass fibers and absorbent fibers. The AR component may comprise between approximately 70% and 99.99% glass fibers and between approximately 0.01% and 30% absorbent fibers, wherein the % is the content weight percent. In a preferred embodiment, the absorbent rigid component comprises approximately 90% glass fibers and 10% absorbent fibers.

The AR component is preferably insoluble and non-degradable. As used herein, the term "insoluble" refers to a material or combination of materials that is not soluble in water at 37° C. As used herein, the term "non-degradable" refers to an AR component which does not lose more than approximately 15% of its weight following 10 days in culture in a culture medium at 37° C. and a 5% $CO_2$ environment.

As used herein, the term "absorbent fibers" refers to fibers constructed from an absorbent material. The term "absorbent material" refers herein to a material that absorbs and holds aqueous solutions by the capillarity of pores within the material, or a material that swells as a result of uptake and retention of aqueous solutions, or a material that does both. In various embodiments, an absorbent material increases in at least one dimension by at least 0.01%, at least 0.1%, at least 1%, at least 10%, or even more when immersed in water for a period of 30 minutes at the physiological temperature. It is to be understood that many absorbent materials reach the equilibrium swelling in a period of hours and that at 30 minutes, the material dimensions may not be final. In other embodiments of the present invention, the AR component comprises glass fibers coated with an absorbent material. It is to be understood that the absorbent fibers can be binder fibers, such that the binder fibers are adhesive-like fibers which bond glass fibers together to form a matrix of glass and absorbent fibers.

A non-limiting list of absorbent materials that may be used with the present invention includes hydrophilic and biocompatible grades of the following materials and their derivatives: poly(vinyl alcohol); ethylene vinyl alcohol co-polymers (typically non-biodegradable materials which degree of hydrophilicity depends on distribution of ethylene (hydrophobic) and vinyl alcohol (hydrophilic) groups); co-polymers of polyvinyl alcohol and ethylene vinyl alcohol; polyacrylate compositions; polyurethane compositions; poly(ethylene glycol) (PEG), otherwise known as poly(oxyethylene) (POE) and poly(ethylene oxide) (PEO), and its derivatives including but not limited to polyethylene glycol methacrylate (PEGMA), polyethylene glycol dimethacrylate (PEGDMA) and polyethylene glycol diacrylate (PEGDA); cellulose and its derivatives including but not limited to methyl cellulose, carboxymethyl cellulose, ethyl cellulose, hydroxyethyl cellulose, hydroxypropyl cellulose; hydrophilic alginic acid, also known as algin or alginate and its derivatives; nitrogen-containing materials such as polyacrylamide (without acrylamide toxic residuals), polyvinylpyrrolidone, polyvinylamine, and polyethyleneimine; electrically charged materials such as poly(lactic acid) also known as polylactide (PLA) in various forms (e.g. poly-L-lactide (PLLA) and its derivatives, poly-D-lactide (PDLA) and its derivatives, poly (L-lactide-co-D,L-lactide) (PLDLLA) and its derivatives), poly(glycolic acid) (PGA) also known as polyglycolide, co-polymers of lactic acid and glycolic acid poly(lactic-co-glycolic acid) (PLGA), co-polymers of PLA and/or PGA with PEG; polymethacrylic acid; poly(hydroxyethyl methacrylate) poly-HEMA, among other absorbent, hydrophilic and biocompatible materials known in the art. Other, non-limiting exemplary insoluble absorbent materials may be derived from a mixture of water-soluble polymers. A mixture of an anionic water-soluble polymer and a cationic water-soluble polymer produces a gel-like insoluble material as a result of neutralization. A mixture of an uncharged water-soluble polymer and an anionic water-soluble polymer may also be neutralized with a mixture of an uncharged water-soluble polymer and a cationic water-soluble polymer.

As used herein the term "biocompatible" refers to cyto-compatible materials which are not toxic and are non-injurious to cells in culture. In various embodiments, a biocompatible material is also cyto-compatible material that does not interfere with cellular functions in vitro, or a cyto-compatible material that does not interfere with cellular functions in vitro and is not immunogenic in vitro. Further, it is understood that certain materials in the above list are degradable and/or soluble in water; however, many polymers are cross-linkable to render them insoluble and non-degradable as per the above stated definitions of insoluble and non-degradable, and many of the above polymers and co-polymers can be combined in various co-polymer compositions to render them insoluble and non-degradable, and further cross-linked to limit water solubility and degradation rates to meet previous definitions of insoluble and non-degradable. Further, it is also understood that these materials are typically less rigid than glass; however, when referring to a rigid absorbent component, it is meant that the resultant matrix comprising glass and absorbent materials is a rigid matrix. It is also understood that the rigid absorbent component is absorbent because of the capillarity of the pores within the rigid component, which preferably has the form of a fibrous matrix, and in certain embodiments is further absorbent due to presence of an absorbent material in the fibrous matrix.

In one embodiment, the absorbent fiber material is both biocompatible and insoluble in water at the temperature of 37° C. and selected from the group consisting of biocompatible and insoluble grades and derivatives of: chemically or physically cross-linked polymers of vinyl alcohol, or un-cross-linked poly(vinyl alcohol) polymers which are insoluble in water at 37° C. owing to their high degree of hydrolysis, high degree of polymerization, and high molecular weight; ethylene vinyl alcohol co-polymers (non-limiting examples are EVAL® resins from Kuraray which are insoluble in water and not readily soluble in most common solvents and water even at elevated temperatures); co-polymers of polyvinyl alcohol and ethylene vinyl alcohol; polyacrylate compositions; polyurethane compositions; cross-linked poly(ethylene glycol) (PEG), polyethylene glycol methacrylate (PEGMA), polyethylene glycol dimethacrylate (PEGDMA) and polyethylene glycol diacrylate (PEGDA); cross-linked cellulose derivatives; cross-linked nitrogen-containing materials such as polyvinylpyrrolidone, polyvinylamine, polyethyleneimine; poly(lactic acid) and poly(glycolic acid); poly(hydroxyethyl methacrylate) etc. In a preferred embodiment the absorbent fiber is a poly vinyl alcohol fiber.

Also included in the present invention is an absorbent rigid component comprising glass fibers having an absorbent coating and/or another coating. The absorbent coating can be made from any absorbent material as described above.

In one embodiment, glass fibers are coated with poly vinyl alcohol (PVOH). The PVOH coating solution can be an approximately 1% weight to volume solution and can be selected from a range of PVOH molecular weights including, but not limited to, approximately 31-50 kDa and 146-186 kDa. Other coatings that may be applied to the rigid fibers include, but are not limited to, Poly-D-Lysine (PDL), Poly-L-Lysine (PLL), MATRIGEL™ matrix, Laminin, Collagen I, Collagen IV, Collagen II, Collagen III, Gelatin, Fibronectin, Poly-L-Ornithine, Polyethyleneimine, and their combinations, such as PDL/Laminin, Laminin/Fibronectin, Poly-L-Ornithine/Laminin, etc. These extracellular matrix proteins and attachment factors are typically used in conjunction with cell-ware and culture-ware products to make surfaces more cell adhesive for cells to attach, while supporting, promoting or regulating cells' growth, and in some cases maintenance of differentiated function. However, in some applications these coatings may be substituted with those that prevent cell adhesion and attachment, such as poly(2-hydroxyethyl methacrylate), alginate, or poly(ethylene glycol). Alteration of the coating is a method to control cellular distribution in the absorbent rigid component. For example, cells can be stimulated to cluster, aggregate and form cell spheroids or allowed to adhere and spread within the absorbent rigid (AR) component. Alteration of the coating is also method to control cellular distribution between the later added gel component and the absorbent rigid component. In other words, cells can be stimulated to grow more on the rigid absorbent component or more in the gel component or equally in both by tuning the cell adhesion molecules present in the gel and the coating of the rigid absorbent component. In some embodiments, these additional coatings are applied on top of the PVOH coating.

The AR component of the scaffold can be made by any method known to those of skill in the art that provides for a void volume of between approximately 70% and 95%. In one embodiment, the AR component comprises rigid fibers and absorbent fibers and is made using a standard wet-laid nonwoven manufacturing process. Wet-laid nonwovens are nonwovens made by a process which is similar to papermaking in which the fibers are suspended and mixed in heated or unheated water or other liquid to produce materials comprising uncut or cut natural fibers and/or synthetic fibers and/or additives. Specialized machines separate water from the fibers to form a uniform sheet of material, which is then bonded and dried. However, in paper compositions the fibers are packed together into a dense structure, and chemical groups attached to their surfaces form hydrogen bonds with similar groups on neighboring fibers. In contrast, textile fibers tend to be longer, stronger, and relatively inert. The end result is that paper tends to be weak, smooth, and dense, while textile nonwovens are stronger, bulkier, less smooth and more porous. For use with cells in long-term culture, long-term submersion in cell culture media, drug and other compounds, buffers, etc., cellulose-based nonwovens may disintegrate and textile-based fibers are, therefore, more preferred.

Typical manufacture of nonwoven bonded fabrics by the wet-laid method includes the steps of swelling and dispersion of the fiber in water, transport of the suspension on a continuous traveling screen, continuous web formation on the screen as a result of filtration, and the drying and bonding of the web. The nonwoven composition is dictated by the amount and types of rigid and/or absorbent fibers, absorbent particles, and/or other additives in the suspension. Diverse short cut (usually a few millimeters to a few centimeters) and long staple fibers, both rigid and absorbent, are available commercially, and absorbent materials may serve as the binder.

In one embodiment, a wet-laid nonwoven manufacturing process is used to make an AR component that comprises glass fibers and poly vinyl alcohol (PVOH) fibers. In this embodiment, absorbent PVOH fibers (e.g., Kuralon brand available from Engineered Fibers Technology) and milled or chopped strand glass fibers (in a range of diameters and cut length from various suppliers, e.g., Lauscha Fiber International Corp. or Saint-Gobain Vetrotex, among other suppliers) are suspended and mixed in a slurry using a beaker and a magnetic stirrer. The mixed fiber suspension is poured onto a screen allowed to dry and then transferred onto a Teflon film and covered by another Teflon film and as such rolled through a hot or cold laminator to obtain desired material thickness and bond. If cold-rolled, the material may be bonded by transferring it under the platen of a T-shirt heat press to compress the material to a final desired thickness for the PVOH fibers to bond to glass fibers using pressure and heat.

When making an absorbent rigid component that comprises glass fibers and PVOH fibers or glass fibers having a PVOH coating, the PVOH fibers can be dissolved at various temperatures providing a method to control the amount of PVOH fiber in the final composition or the thickness and concentration of the PVOH coating on the glass fibers, resulting from the PVOH fiber dissolution. For example, Kuralon brand fibers (supplier Kuraray, distributor Engineered Fibers Technology LLC) dissolve at temperatures of 60° C. (distributor part No. VPB105-2), 70° C. (No. VPB105-1), 80° C. (No. VPB101, VPB071, VPB041), 99° C. (distributor part No. VPB102), and >100° C. (No. VPB103, VPB203, VPB303, VPB033, VPB053) according to the distributor. In laboratory conditions, this can be done by, for example, heating the water suspension of glass and PVOH fibers in a beaker using a heated magnetic stirrer, followed by drying on a screen and hot or cold rolling the material into a desired thickness. Alternatively, glass fibers may be mixed in a beaker on a heated magnetic stirrer in the PVOH solution, and then poured on a screen followed by material rolling and heat treatment to achieve the bond between PVOH coated glass fibers.

Further, when making an absorbent rigid component that comprises glass fibers and PVOH fibers, the resultant matrix can be additionally impregnated by the PVOH, providing an additional method to control the amount of absorbent material in the final AR component. For example, if the suspension of glass fibers and PVOH fibers comprises a blend of PVOH fibers, wherein at least one PVOH fiber type has a lower, and at least one PVOH fiber type has a higher, dissolution temperature than that at which the fiber suspension is mixed and maintained, then dissolved PVOH fibers may be used to impregnate glass and non-dissolved PVOH fiber matrix. Alternatively, glass and PVOH fibers may be heated and mixed in a solution comprising dissolved PVOH to impregnate glass and non-dissolved PVOH fiber matrix.

When making an AR component that comprises glass fibers and PVOH fibers, glass fibers having a PVOH coating, or glass fibers and PVOH fibers collectively PVOH coated, the PVOH fibers and/or dissolved PVOH in a fiber suspension may be substituted by or complemented with the PVOH particles which swell or dissolve, so as to serve as a substitute of PVOH fibers or an additional binder for the glass fibers, providing yet an additional method to control the AR component composition, wet strength and structural stability for vigorous routine handling during and following days in culture.

An exemplary absorbent rigid component comprising glass fibers and PVOH fibers is produced by Millipore Corporation as the G041 fiber substrate. The G041 fiber substrate comprises borosilicate glass fibers and poly vinyl alcohol fibers. Since the making of these materials is quite common, wet-laid glass fiber nonwovens with the PVOH fiber binder are available from a number of suppliers other than Millipore, including Pall Corporation absorbent pads (borosilicate glass fiber with the PVOH binder) and CRANEGLAS™ from Crane Nonwovens, among others.

The AR component of the present invention can be produced using various methods known in the art of nonwoven manufacturing or any other custom method of making. An exemplary method is the above described wet-laying of fiber suspension to form fiber web by way of binders in the suspension, and/or binder fibers and/or particles that swell and/or dissolve and/or melt to bond non-dissolving or non-melting fibers together during a subsequent cold or hot rolling step. Another exemplary method is dry-laying of fiber blends comprising various staple or custom-made fibers (including glass and absorbent fibers) which are captured on a screen from air streams comprising fibers, followed by subsequent bonding. Yet another exemplary method comprises spun-laid or melt-blown processes integrating filament extrusion (spinning), drawing, deposition (lay-down) and bonding to simultaneously form both long filament fibers and webs in glass and other materials, and modifications of these processes to co-spin, or mix, shorter and longer filament fibers during or after spinning, drawing or laying down. In yet another exemplary method, uniformly dispersed short and/or long filament fibers of glass and absorbent materials can be made into a web using hydro entanglement, mechanical needle punching, thermal, chemical, ultrasonic, or other types of bonding either alone or in combination with other (e.g., wet- or dry-laid, or spin) processes, and prior to, during, or following material rolling into a desired thickness.

Once obtained, the AR component can be autoclaved for varying periods of time. In some embodiments, the absorbent rigid component is steam autoclaved at approximately 130° C. for approximately 45 minutes, followed by dry heating at approximately 130° C. for approximately 10 minutes, followed by drying for approximately 1 hour (all in the autoclave). In other embodiments, the absorbent rigid component is steam autoclaved at 126° C. for 45 minutes and then left to dry in the autoclave for at least six hours prior to use.

The final absorbent rigid component composition governs its hydrophilicity, absorbency, wet strength, and optical properties. As defined herein, "wet strength" is the measure of how well the AR component holds together upon bearing a force (including wetting). The wet strength is routinely expressed as the ratio of wet to dry tensile force at break. It is also understood that geometrical properties of the absorbent rigid component, including but not limited to pore size, porosity, tortuosity, uniformity of dispersion of glass fibers and absorbent fibers, and/or the absorbent rigid component composition, the size of fibers and their finish, impregnation and treatment using various methods known in the art (e.g. corona and gas plasma treatment) provide a method to control (1) the wicking rate, sorptivity, and liquid holding capacity of the AR component against the forces of gravity, and therefore, the wicking rate of cells and the sol state gel to the interior of the AR component and the homogeneity of three-dimensional cell and gel distribution, adhesion and attachment to the interior of the AR component; (2) wet strength of the absorbent rigid component; and (3) optical properties for imaging access.

Once the absorbent rigid component of the scaffold is obtained, in some embodiments, the gel component is then added into the void volume of the AR component. As used herein, the term "gel" includes a variety of products in gel form including, but not limited to, collagen, gelatin, elastin, fibrin, fibronectin, laminin, and fibroin, among others; polysaccharide-based glycosaminoglycans such as chondroitin sulfate; hyaluronic acid and its derivatives; chitosan; alginate; cellulose and its derivatives, such as methylcellulose; hydroxypropylcellulose and carboximethylcellulose; dextran; agar; agarose; starch; carrageenan; galactomannan such as guar gum; xanthan or xanthan gum; and pullulan. Examples of commercially available "natural" gels are Life Technologies, AlgiMatrix, BD MATRIGEL™, Glycosan HyStem and Extracel. Examples of commercially available synthetic gels are BD PuraMatrix, Glycosan PEGgel, and QGel SA QGel. The term "MATRIGEL™" is defined herein to refer to a biological product typically comprising Laminin, Collagen IV, Entactin, and heparin sulfate proteoglycan among other constituents. In some embodiments, the MATRIGEL™ is a BD MATRIGEL™ (part No. 354263) Basement Membrane Matrix, Growth Factor Reduced, High Concentration (HC)*LDEV-Free.

Accordingly, provided herein is a 3D cell culture scaffold composition comprising a rigid absorbent component and a gel component, wherein the rigid absorbent component has a void volume of between approximately 70% and 95%, which void volume comprises the gel component and one or more cells. In some embodiments, the void volume is between approximately 85-95%. The rigid absorbent component can comprise a material having an optical transmission of at least 70% at a normal incidence in a range of wavelengths between approximately 400 nm and 2 μm for up to 0.5 mm of material thickness. In some embodiments, the rigid absorbent component comprises a material having an optical transmission of at least 80% at a normal incidence in a range of wavelengths between 350 nm and 2 μm for up to 0.5 mm of material thickness.

A 3D cell culture scaffold composition comprising a rigid absorbent component and a gel component can be a composition wherein the rigid absorbent component comprises glass fibers. In some embodiments, the glass fibers are borosilicate glass fibers. The glass fibers can have a diameter between approximately 3 and 30 μm. One example of such a rigid absorbent component is a Millipore G041 material. In other or further embodiments, the scaffold comprises approximately 90 glass fibers and 10% of absorbent fibers, wherein the absorbent fiber can be a poly vinyl alcohol fiber. In still other or further embodiments, the scaffold comprises glass fibers having an absorbent coating. The absorbent coating can be any of those described herein, and in one embodiment, is poly vinyl alcohol coating. The absorbent rigid component can also further comprise an additional coating.

A three-dimensional cell culture scaffold composition comprising a rigid absorbent component and a gel component as provided herein can comprise any gel component known to those of ordinary skill in the art. In some embodiments, the gel component is selected from a group consisting of a collagen, gelatin, laminin, MATRIGEL™, hyaluronan, alginate, agarose, Pluronic F-127 and a chitosan. When MATRIGEL™ is selected as the gel component, the MATRIGEL™ can have a protein concentration of up to approximately 16 mg/ml.

In a preferred embodiment, the gel is a sol-state gel when it is applied to the AR component. "Sol-state gel" refers herein to a gel that is in liquid form. It should be understood that the gels of the present invention may be "tunable" and may comprise one or more naturally derived polymers, one or more synthetic polymers, and/or one or more grafted cell adhesion molecules. Gels may be derived from plants or algae, secreted by or derived from secretion of animal and human cells, including de-cellularized matrices derived from animal, human and cadaver tissues, and synthetic or derived using suitable molecules and cross-linked to form gels that are substantially insoluble in aqueous solutions, and hydrolytically, enzymatically or otherwise non-degradable, or degradable.

It is a surprising finding of the present invention that a sol-state gel such as MATRIGEL™ instantly wicks into the absorbent rigid component of the scaffold. Even MATRIGEL™ samples containing high protein concentrations of up to 16 mg/ml wick instantly into the AR component. This wicking property and the ability of the AR component to hold cells and gel within the void volume distinguishes the present invention from all prior art 3D cell culture compositions. In some embodiments, the AR component wicks a maximum hold volume of a sol-sate gel within 1-5 seconds or 1-10 seconds. A "maximum hold volume" is defined as the highest volume of a given liquid that a given mass of absorbent rigid material can absorb in a material sample of defined external and internal characteristic dimensions in a dry state. The maximum hold volume can be different for the same weight and volume of material in different thicknesses. The superior wicking capacity of the present invention has been established on video using MATRIGEL™ samples ranging from 8 mg/ml to 16 mg/ml using a positive displacement micropipette, a standard micropipette, and partial or complete submersion of the AR component within the sol-state gel component.

The present invention is the first to describe a three-dimensional cell culture composition that contains a rigid component with an absorbent property used in conjunction with a gel material. This combination allows for the superior functioning of the present invention over prior art compositions. More particularly, the present invention provides a 3D cell culture composition that holds sol-state gel and cells with little or no leaks during gel gelling, high wet strength of the cell culture composition for its routine handling following days in culture, and imaging access for standard high-throughput screening and high-content screening. This allows for ease of high-throughput plating of consistent cultures, and routine handling of cultures in high throughput procedures commonly used during routine compound screening and pharmacological profiling of drug candidates in the life science and drug discovery sectors.

The sol-state gel may be applied to the absorbent rigid component via any method known to those of skill in the art. For example, the sol-state gel may be applied via pipette to the top of the AR component or the AR component may be wholly or partially immersed in the sol-state gel.

The cells comprised within the sol-state gel may be of any type and can be prokaryotic, such as bacteria, and eukaryotic, such as animal and human cells. The cells can be the same or a mixture of different types of cells. In a preferred embodiment, the cells are of animal and/or human origin and normal or diseased of animal and/or humanized animal and/or human origin. Examples include normal, infected, malignant, or otherwise diseased cells from various stages of donor disease progression. These cells may be primary cells, secondary cells, cell lines, transfected, transgenic, or stem cells, among others. A non-limiting list of exemplary cells includes cells from connective, nervous, muscle, epithelial, and vascular tissues. Exemplary cells are cells from brain, spinal cord, heart, liver, intestine, pancreas, gallbladder, kidney, lung, breast, ovary, thyroid, cartilage, muscle, skin, immune system cells, stem cells, etc.

The present invention also includes a method of culturing cells comprising placing the cells in a 3D cell culture scaffold composition, which composition comprises a rigid absorbent component and has a void volume of between approximately 70% and 95%, thereby creating a 3D cell culture. In some embodiments, the void volume is between approximately 85-95%. The rigid absorbent component can comprise a material having an optical transmission of at least 70% at a normal incidence in a range of wavelengths between approximately 400 nm and 2 μm for up to 0.5 mm of material thickness. In some embodiments, the rigid absorbent component comprises a material having an optical transmission of at least 80% at a normal incidence in a range of wavelengths between 350 nm and 2 μm for up to 0.5 mm of material thickness.

A 3D cell culture scaffold composition comprising a rigid absorbent component used according to these methods can be a composition wherein the rigid absorbent component comprises glass fibers. In some embodiments, the glass fibers are borosilicate glass fibers. The glass fibers can have a diameter between approximately 3 and 30 μm. One example of such a rigid absorbent component is a Millipore G041 material. In other or further embodiments, the scaffold comprises approximately 90% glass fibers and 10% of absorbent fibers, wherein the absorbent fiber can be a poly vinyl alcohol fiber. In still other or further embodiments, the scaffold comprises glass fibers having an absorbent coating. The absorbent coating can be any of those described herein, and in one embodiment, is poly vinyl alcohol coating. The absorbent rigid component can also further comprise a coating.

The present invention further describes a method of high content screening of one or more three-dimensional cell cultures. As used herein, the term "high content screening," also known as high-content analysis (HCA) or visual screening, includes any method used to analyze whole cells or components of cells with the readout of one or more parameters simultaneously. High-content screening is frequently implemented in the context of phenotypic screening. Typical parameters analyzed by high content screening include increases or decreases in the production of cellular products, such as proteins or ribonucleic acids, and changes in cell morphology, such as changes within the cytoplasm, nucleus and/or organelles. In some embodiments, the imaging is performed in a high throughput assay. In other or further embodiments, the scaffold and cells are imaged at a depth of between approximately 0 and 450 μm.

It should be understood that the rigid absorbent component and the gel component of the 3D cell culture used in the imaging methods of the present invention can be any as described above or below in the Examples. In a preferred method, the rigid absorbent component comprises a material having an optical transmission of at least 70% at a normal incidence in the range of wavelengths between approximately 400 nm and 2 μm for up to 0.5 mm material thickness. In a more preferred method, the rigid absorbent component comprises a material having an optical transmission of at least 80% at a normal incidence in the range of wavelengths between 350 nm and 2 μm for up to 0.5 mm material thickness.

In some high content screening assays, fluorescent molecules are used to label various different cellular products such that each labeled cellular product can be distinguished from another. Through the use of fluorescent molecules with different absorption and emission maxima, it is further possible to measure and detect changes in whole cells and sub-cellular components in parallel.

The present invention provides compositions and methods that for the first time can be used to image extracellular matrix (ECM) together with cells in long-term culture using high content screening methods. The 3D cell cultures of the present invention are advantageous for high content screening of ECM gel alterations by cells in culture and compounds that modulate matrix alterations that involve confocal microscopy and even more advantageous for high content screening methods that are performed on a high throughput basis. In one embodiment, the present invention provides a method to fluorescently label, image and analyze both cells and gel component in one or more 3D cell cultures wherein the one or more cell cultures comprise a rigid absorbent component and a gel component, wherein the rigid absorbent component has a void volume of between approximately 70% and 95%, which void volume comprises the gel component and one or more cells. Specifically, the invention provides a method of using two- or multi-channel confocal microscopy, wherein each channel has specific excitation and emission bandwidth, to simultaneously image fluorescently labeled extracellular matrix, and one or more cells such that the different cell phenotypes, and in some embodiments, the gel, fluoresce and can be imaged in different colors. Further, three-dimensional cell culture components such as fluorescently labeled cells, and in some embodiments, the gel, were imaged in a z-stack at a depth of between approximately zero and 450 μm.

The three-dimensional cell cultures of the present invention are further advantageous for high throughput screenings that involve plate reader readouts and even more advantageous for high throughput screening methods that are performed after long term cell culture, after a period of approximately 7 to 16 days following cell culture plating. Traditional multi-well plates and plate reading methodologies may be used with the present invention.

The scaffold composition is further advantageous because it can be cut into any shape and size, coated and/or filled with any gel and/or cells. This provides for a method to spot cultures side-by-side where said cultures comprise the same or different cell types to better model tissue heterogeneity in health or disease or study cell sub-populations in a given population of cells. The scaffold composition is further advantageous because it can be cut into any shape and size, coated and/or filled with any gelling or non-gelling polymers, active and inactive biologicals, pharmaceuticals, biopharmaceuticals and test compounds for their quality control testing, toxicity or other forms of testing with or without the cells in culture or with and without cells in suspension Spotting and wicking provide for a method to embed molecules of interest, either as solutions wicked by the material or as substrate-bound molecules. Material may also be coated and further comprise a gel or other embedded material before other molecules are wicked or spotted. A plurality of molecules, the same molecules in different concentrations in their respective solutions, or a plurality of molecules in different concentrations may all be embedded into the material by spotting them onto the material or by wicking. These methods provide for a means to setup gradients of wicked solutions/molecules, or gradients of substrate-bound molecules within the material, wherein the material further comprises a coating, a gel, or both and to test those molecules and their respective concentrations and gradients in situ, directly with the cells in culture or with the cells in suspension. The scaffold composition is further advantageous because it can be partly or wholly overlaid or overlapped by another scaffold composition. This provides for yet another method to form gradients, overlay or overlap cultures, or test molecules and their gradients with the cells in culture or with the cells in suspension suspended within the interior of the AR component.

It should be understood that a gradient can be created with any appropriate molecule, and that the term "molecule" as used herein encompasses all such materials. Molecules subject to gradient formation include, but are not limited to, cytokines such as interlukins (i.e., IL-1, IL-2, IL-3, IL-4, IL-5, IL-6, IL-7, IL-8, IL-9, IL-10, IL-12, IL-11, and IL-13), lymphokines (i.e., GMCSF, and IFN-gamma) and chemokines (i.e., CCL, CXCL, CX3CL, and XCL), TNF, interferons, growth factors (i.e., VEGF, FGF, IGF, and EGF), hormones, and survival factors (i.e., IGF1).

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

Fabrication of Hydrophilic, Absorbent Three-Dimensional Substrate Compositions of Differing Rigidities Using an Exemplary Wet-Laid Method Unless explicitly written otherwise, fabrication of three-dimensional (3D), porous, hydrophilic, absorbent substrates of varying rigidities using an exemplary wet-laid production included the following:

Fiber weighing and initial dispersion. Polymer fibers were dispersed mechanically as shown in FIG. 1A by rubbing a weighed mass of fibers between textured surfaces until they were fluffy. Initial dispersion of glass fibers was done by sonication in 70% EtOH for 1-10 minutes.

Wet dispersion. Dispersion was done in 70% EtOH using a magnetic stirrer for 24 hours at room temperature. During wet dispersion, fiber slurry was periodically vortexed by transferring slurry into 50 ml conical tubes followed by 10 seconds vortexing. Vortexing and two tube inversions per vortexing were done 4 times in a 24-hour period.

Figure 1B:
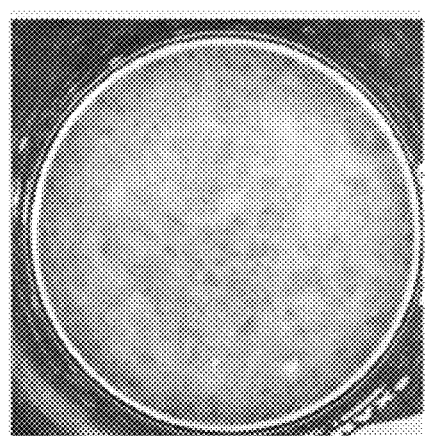

Fiber settling and drying. After wet dispersion, 70% EtOH and the stirring rod were removed as shown in FIG. 1B. Fiber slurry was transferred into another beaker with a siliconized paper covering the beaker bottom. Fiber slurry was uniformly spread over the siliconized paper by way of a rolling cylinder and dried in the chemical fume hood for 48 hours.

Figure 1C:
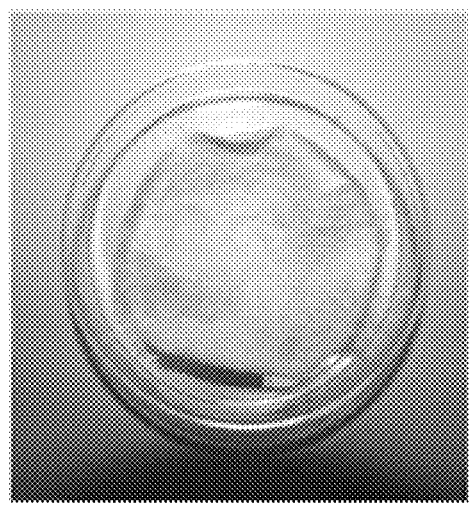

Pressing (for Composition I in Example 2 only). After drying, an absorbent hydrophilic sheet laid on siliconized paper was transferred into a heated press comprising shim standoffs of 400 μm thickness to obtain final thickness of the sheets of approximately 400 μm after pressing as shown in FIG. 1C. No heat was applied.

Dispersion of different fibers at a different mass fraction provided for a method to control substrate composition. Varying surface area of a vessel in which fibers were uniformly spread by way of a roller and dried provided for a method to control substrate thickness and solid-volume-fraction of each component in the substrate composition. Pressing or alternatively vacuuming with or without heating during or after drying provided yet another method to control substrate thickness solid- and void-volume fraction. The term substrate solid-volume fraction refers to the volume of all fibers, including any fiber coating, in a given substrate volume as defined by its external length, width and height after the making Stirring, centrifugation, sonication and other tested forms of mechanical agitation, including but not limited to the addition of 1-2 mm Teflon spheres into the fiber slurry to improve fiber dispersion, provided for a method to control fiber dispersion and 3D fiber distribution within the substrate. Increasing temperature during wet dispersion provided for a method to dissolve some fibers and, therefore, impregnate others. The addition of other agents or other fibers during wet dispersion provided for a method to impregnate fibers and further control substrate composition, wet strength, hydrophilicity, absorbency, and rigidity.

Accordingly, substrate composition, fiber diameters, substrate porosity, tortuosity, thickness, hydrophilicity, absorbency and wet strength were all adjustable by the disclosed exemplary fabrication method and were optimized to yield 400 μm-thick substrates with 10% solid volume fraction for subsequent testing. The steps used in making the substrates are also used in commercial wet-laid non-woven production, thus making the disclosed laboratory scale production method amenable to commercial production. Disclosed exemplary fabrication methods may be substituted by thermal bonding of polymer binder fibers with glass fibers, or fabricated using any other method known in the art of non-woven and paper-making.

Example 2

Characterization of Custom Absorbent 3D Substrate Compositions of Differing Rigidities The following compositions (labeled I through VI) were made using the method in the Example 1 and characterized for their wicking and water retentive properties:

| Label | Fiber slurry composition |
|---|---|
| I | 0.1 g PVOH fiber VPB 105-2 in 75 ml 70% EtOH |
| II | 0.2 g PVOH fiber VPB 102-5 + 0.2 g glass fiber EC-11-3-SP in 300 ml 70% EtOH |
| III | 0.1 g Lyocell fiber Tencel 1.5d + 0.2 g glass fiber EC-11-3-SP in 225 ml 70% EtOH |
| IV | 0.05 g PVOH fiber VPB 105-2 + 0.15 g glass fiber EC-11-3-SP in 150 ml 70% EtOH |
| V | 0.05 g PVOH fiber VPB 102-5 + 0.95 g glass fiber EC-11-3-SP in 750 ml 70% EtOH |
| VI | g glass fiber EC-11-3-SP in 200 ml 70% EtOH |

PVOH fibers: VPB 105-2 and 102-5 were Kuraray Kuralon PVOH fibers, Denier 1 (diameter 11 μm), and a cut length of 4 mm and 5 mm, respectively. According to Engineered Fibers Technology (supplier), fibers dissolved in water at a temperature≥60° C. and >99° C. for VPB 105-2 and 102-5, respectively. Fibrillated fiber, Tencel® 1.5 d was a 1.5 Denier, 6 mm long, fibrillated Lyocell fiber with a high surface area owing to sub-micron to a few micron fibrils covering a broad range of diameters. According to Engineered Fibers Technology (supplier), the fiber was a pure alpha-cellulose fiber of high wet strength and dry modulus (the tensile strength was 2× of dry rayon and 3× of wet rayon), high absorbency and radial swelling when wet with water imbibition of 65%-70%, and good dispersibility of fiber in water. Glass fiber, EC-11-3-SP was chopped textile E-glass type fiber, 11 μm in diameter, 3 mm cut length, with Polyvinyl alcohol sizing at a sizing content of 1.5%, according to Lauscha Fiber International (supplier). The "sizing" meant that glass fibers were coated by PVOH. PVOH coating was generally different from that in PVOH fibers. Polyvinyl Alcohols come in many polymer grades with respect to molecular weight, degree of hydrolysis, degree of polymerization, etc. This affects their solubility, dissolution temperature, hydrophilicity, absorption and, therefore, swelling, which was generally different for PVOH coatings and fibers.

400 μm-thick substrate Compositions I-VI at 10% solid volume, all wicked and absorbed 30 μl drop of sol-state growth factor reduced (GFR) MATRIGEL™ at 8 mg/ml protein concentration. For all compositions, wicking was instantaneous (ice-cold sol-state gel was wicked and spread while it was dispensed) or within 10 seconds. Materials were further tested with larger volumes of water and MATRIGEL™. It was found that compositions I-IV had better retention of water, i.e., did not leak on dispensing 300-600 μl of water while compositions V-VI did leak due to lower content of absorbent materials in their composition. Compositions with a higher percent weight of the absorbent component (approximately greater than 5% for absorbent materials tested), had radially more uniform spread of both water and sol-state MATRIGEL™ drops dispensed using micropipette.

Figure 21A:
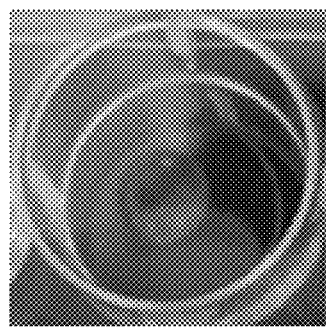
FIGS. 21A-21C refer to cultures seeded without the substrates, FIGS. 21D-21F refer to cultures seeded into uncoated steam-autoclaved G041 substrates, and FIGS. 21G-21I refer to cultures seeded in steam-autoclaved and then PDL-coated substrates.
Figure 21B:
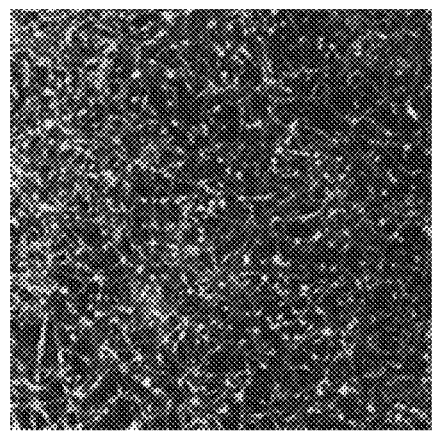
Figure 21C:
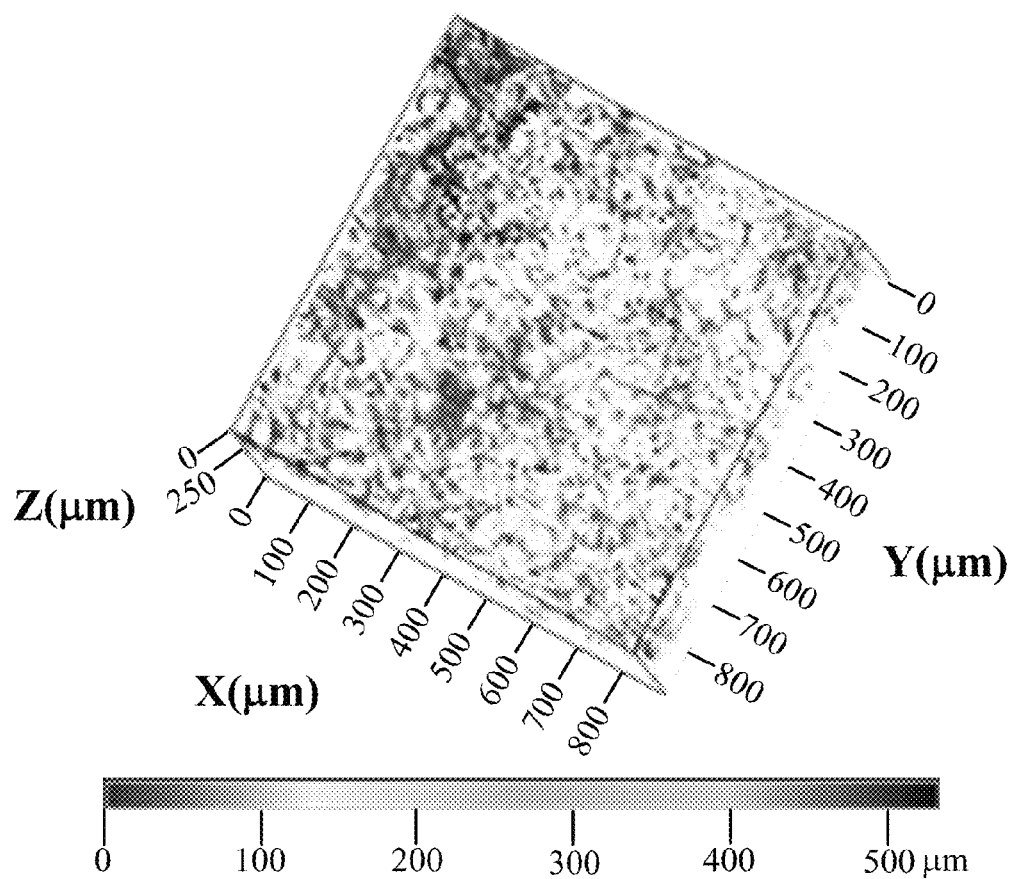
Figure 21D:
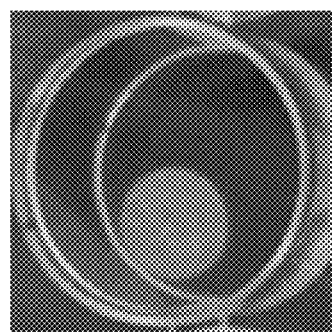
Figure 21E:
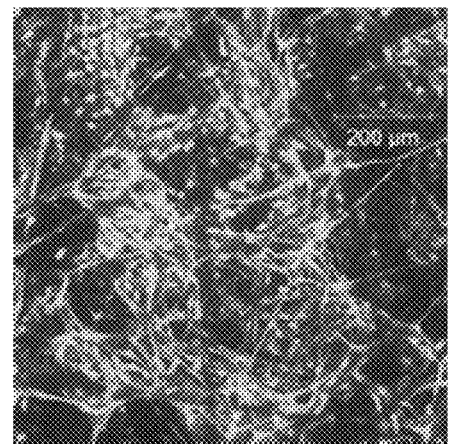

Composition I was imaged dry and wet following the addition of brown-dyed water (FIGS. 21A and 21D). Arrows point to changes in fiber diameter before and after wetting. When wet, fiber diameter approximately doubled and became even more transparent as it absorbed water. After wetting, material dried slowly, making it suitable for the transfer of 3D cultures contained in the material from one dish to another. During drying, fiber diameter was reduced but not to original size within 30 minutes, suggesting that the material still retained water. Composition II imaged dry and wet (FIGS. 21B and 21E) under the same conditions as Composition I showed that VPB 102-5 fibers increased in diameter and absorbed water but absorbed less than VPB 105-2 fibers in Composition I. Composition III dry and wet (FIGS. 21C and 21F) under the same conditions as Composition I showed that cellulose fiber (TENCEL® lyocell) swells in water more than VPB 102-5 but less than VPB 105-2 fiber. Cellulose fibers were less transparent than PVOH VPB 105-2 fiber and dried faster than did PVOH fibers as seen by reduction in this fiber in 1 hour. However, wet laying fibrillated fibers provided for a means to produce a range of fiber diameters using a single material.

Figure 3A:
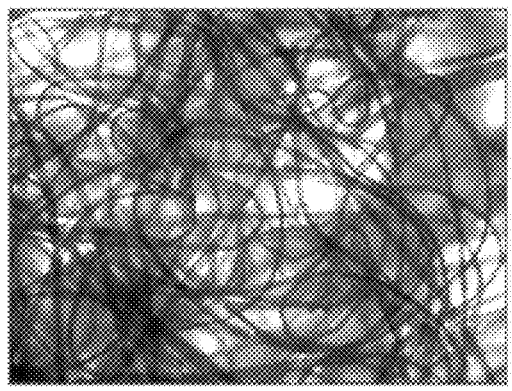
FIG. 3 contains photographs of rigid absorbent substrates comprising (3A) 25% VPB 105-2 polyvinyl alcohol fibers and 75% polyvinyl alcohol (PVOH) coated glass fibers; 5% VPB 102-5 polyvinyl alcohol fibers and 95% PVOH-coated glass fibers in dry (3C) and wet (3D) state; and (3B) PVOH-coated glass fibers. All images were taken at 10× (x=980 µm, y=735 µm).

Composition IV was fabricated following Example 1 with the following exception. After initial glass fiber dispersion by 1 minute sonication, and after initial PVOH fiber mechanical dispersion, a strainer was custom-fitted into the interior of a 50 ml conical tube. The PVOH fibers were first laid on the strainer followed by the addition of glass fibers in 70% EtOH on top of the PVOH fibers. The tube was centrifuged at 1000 rpm for 3 minutes to improve fiber dispersion. Strainer comprising fibers were then removed and a slurry of glass and PVOH fibers were placed in a beaker for a 24-hour wet dispersion. Thereafter, the fabrication in Example 1 was followed. As shown in FIG. 3A, with a centrifuging step, fibers were more curved and curled. The radius of curvature was higher for glass-type fibers than for the PVOH fibers, consistent with the higher rigidity of the former.

Figure 3B:
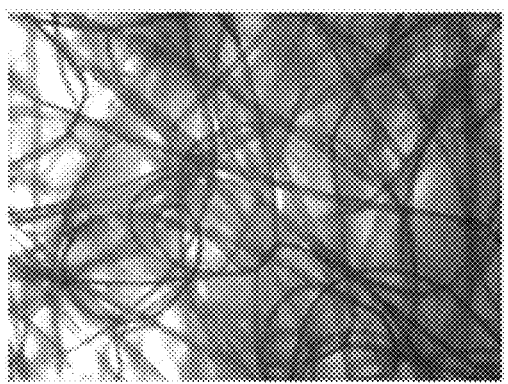
Figure 3C:
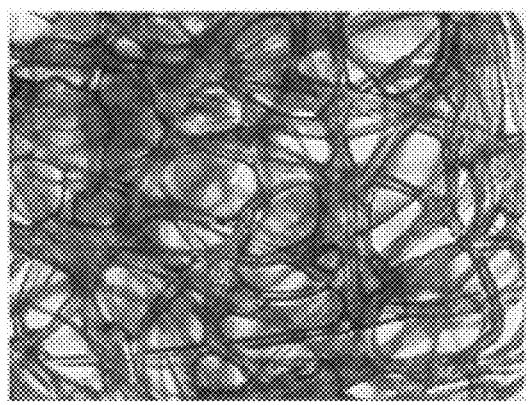

Composition V was fabricated following Example 1 with the following exception. At the end of the 24-hour wet dispersion with a magnetic rod still stirring the slurry, approximately ⅕ of the fiber slurry was removed and transferred into a smaller beaker. The excess 70% Ethanol was aspirated and approximately ⅓ of the fibers were transferred into a 50 ml centrifuge tube comprising a custom-fitted strainer onto which the fibers were laid and then submerged in 70% Ethanol. The tube was centrifuged at 1000 rpm for 3 minutes, after which the strainer comprising the material was removed and transferred into the base of a Petri Dish in a chemical fume hood for 48-hour drying. A photograph taken at the top of the substrate (FIG. 3B) shows that most fibers were PVOH fibers which swell when wet even though their mass fraction in the composition was 5%. Still, in a wick test using 30 μl of sol-state 8 mg/ml protein GFR MATRIGEL™, the wicking rate was similar (instantaneous or under 10 seconds) whether MATRIGEL™ was delivered to the top (comprising predominantly PVOH fibers) or the bottom side (comprising predominantly PVOH-coated glass fibers) of the substrate. This particular centrifuging arrangement provided for a method to stratify fibers in the scaffold and therefore control substrate composition in the z-direction. Materials comprising layers of distinct compositions in the z-direction are advantageous for reconstructing multi-layered tissues, wherein different tissue layers present different cell demands with respect to biomechanical and permeability properties of the extracellular environment.

Figure 3D:
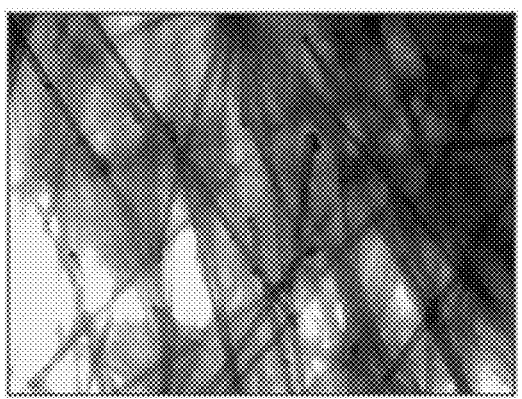

Among all compositions tested, Composition VI, comprising an absorbent (PVOH) coating on rigid glass fibers (FIG. 3D) was the least absorbent. After addition of dye solution in DI-water, followed by 24-hour room temperature drying, the fiber surface was stained as confirmed visually. Still, the staining of absorbent coating on glass fiber was weaker than that of Material D in Example 3, corroborating that EC-11-3-SP fiber coating either comprised a less absorbent form of PVOH than that in CRANEGLAS™ or the coating was thinner. Nevertheless, Composition VI had no absorbent fibers, merely an absorbent coating on rigid glass fibers, yet it was still absorbent.

Accordingly, controlling substrate composition via absorbent polymers and glass provided for a method to control substrate hydrophilicity, absorbency, wet strength, uniformity in circularity of spotted ingredients, and 3D-distribution of said ingredients through the material thickness, and a method to control substrate stiffness, wet strength, ease of handling using tweezers, following days of immersion in common cell culture and pharmaceutical solutions.

Example 3

Characterization of Commercial Materials as Hydrophilic, Absorbent, Rigid, 3D Substrate Compositions It was found that commercial materials may also be used to substitute compositions in Example 2 (with or without additional modifications). The following materials were tested:

| Material label | Supplier, Product No. and Material Description |
| --- | --- |
| A | Millipore Corp., Product No. GFCP203000, G041 glass fiber conjugate pad |
| B | Pall Corporation, Product No. SMCON64, conjugate pad type 8964 |
| C | Pall Corporation, Product No. SMCON75, conjugate pad type 8975 |
| D | Crane Nonwovens, CRANEGLAS™ 230 |

Materials A, B, and C comprising glass fibers with "PVOH binder," "PVOH binder fiber," or "PVOH" of suitable porosity were also available from Whatman—GE Healthcare and Ahlstrom Filtration. Other suppliers such as Munktell or Advantec MFS offer the same in lower porosity (deemed less suitable for 3D cell culture applications due to cell sieving).

For all wicking tests, materials were punched into 9.5 mm-diameter disks using a punch tool and tested. For the MATRIGEL™ wicking test, 30 µl of 8 mg/ml protein ice-cold sol-state GFR MATRIGEL™ was delivered to untreated disks using standard micropipette and standard pipet tips. Prior to dispensing, pipet tips were kept in the freezer to be ice-cold in agreement with BD Biosciences MATRIGEL™ dispensing protocol. For all aqueous dye solution wicking tests, Ateco Spectrum Super Red gel food color was dissolved in DI water followed by filtering through a 0.2 µm filter. The dye solution viscosity was water-like when delivered to material disks in 30 µl volume.

According to the supplier, Material A was 0.41 mm thick and weighed 75 g/m$^2$. The material safety data sheet (MSDS/SDS No. 00001057 Rev. A 26 Mar. 2010) stated that the chemical name was "Borosilicate glass fibers (11 µm in diameter and 1-1.5 cm in length) with Polyvinyl Alcohol." The MSDS further stated in Section 3 Composition/Information on Ingredients: "Glass, Oxide, Chemicals: >90% (content weight percent) and Polyvinyl Alcohol <10% (content weight percent)." Measured material porosity in the lab was approximately 88%. Caliper measured thickness was between approximately 0.355 and 0.406 mm when pressed.

Figure 4:
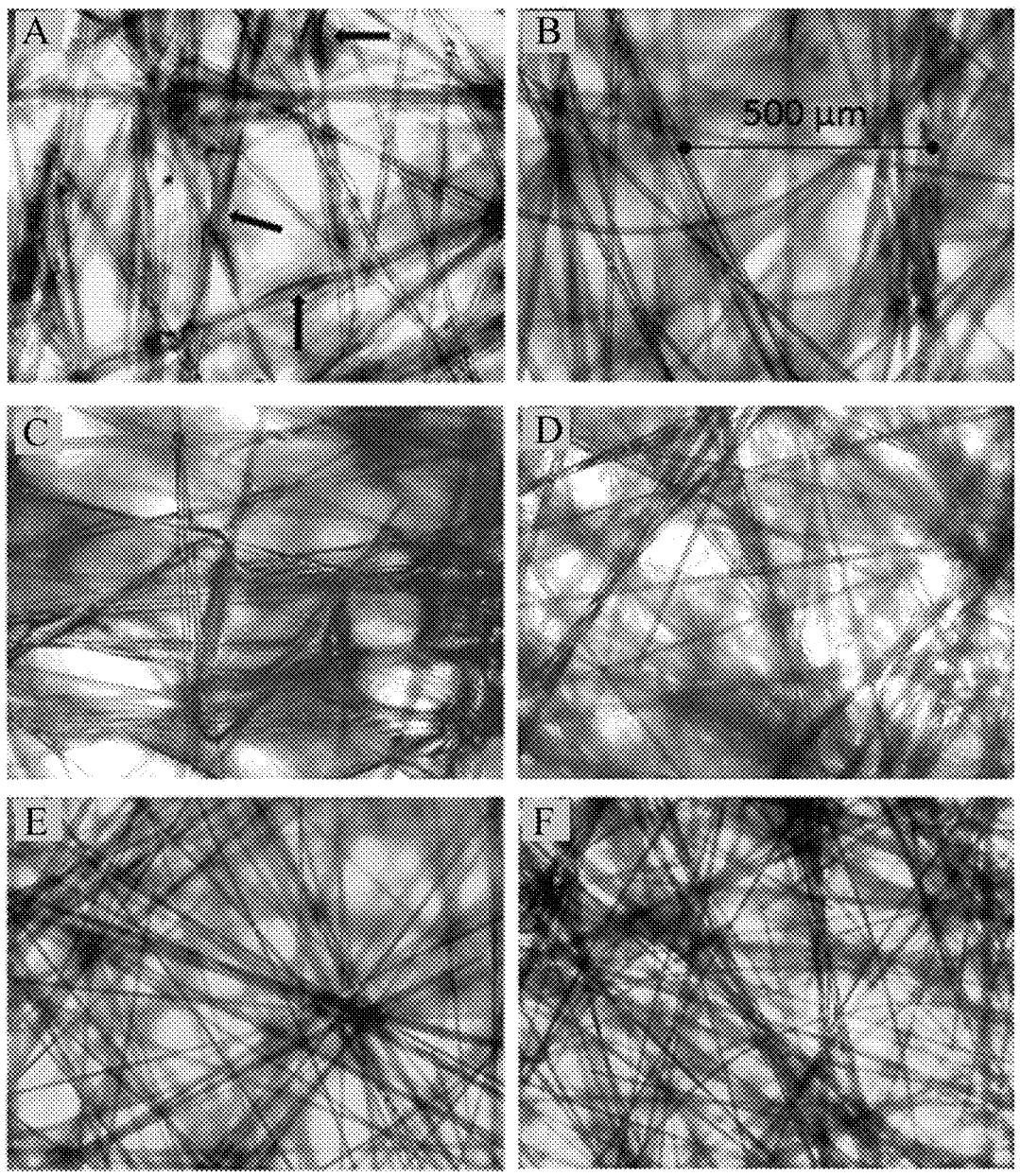
FIG. 4 contains photographs of G041 material in wet (A) and dry state (B), SMCON64 material in wet (C) and dry state (D) and CRANEGLAS™ 230 material 0.102 mm thick (E) and 0.229 mm thick (F) after staining followed by 24-hour room temperature drying. All images were taken at 10× in bright field (x=980 µm, y=735 µm).

Material A disks instantly wicked MATRIGEL™. When wetted with a dye solution, PVOH fibers and/or PVOH coating on glass fibers swell and turned red consistent with the dye uptake by absorbent materials in Material A as shown in FIG. 4A. After a 24-hour room temperature drying, red-stained PVOH binder fiber and/or PVOH coating on glass fibers reduced in diameter as shown in FIG. 4B. After drying, the surface of the glass fibers had a thin red coating confirming that these fibers were PVOH sized (coated) because MSDS stated there were only two ingredients in the material composition (glass and PVOH). The staining showed that absorbent fibers formed a 3D absorbent sub-network within the material extending to all of its surfaces.

According to the supplier, Material B was high wet strength type 8964 conjugate pad comprising borosilicate glass fiber with PVOH binder, measuring 355.6-508 µm in thickness, with a basis weight of 75.1 g/m$^2$, average wicking rate of 141 seconds per 3 cm, and water absorption capacity of 54 µl/cm$^2$. For Material B, the rate of MATRIGEL™ wicking appeared equal to or higher than that of Material A. The radial spread of MATRIGEL™ after dispensing was more circular in Material B than in Material A. In Material B, PVOH fibers were longer and more uniformly wound around the glass fibers than in Material A. Microscopic inspection and dye-staining shown in FIG. 4C revealed that Material B had higher PVOH fiber content than Material A. After a 6-hour drying, the diameter of stained PVOH fibers was reduced (FIG. 4D). The staining showed that absorbent fibers formed a 3D absorbent sub-network within the material extending to all of its surfaces. The PVOH polymer properties in Materials A and B were not known and considered different.

According to the supplier, Material C was type 8975 conjugate pad comprising borosilicate glass fiber with PVOH binder, measuring 228.6-330.2 µm in thickness, with a basis weight of 49.1 g/m$^2$, average wicking rate of 156 seconds per 3 cm, and water absorption capacity of 19 µl/cm$^2$. Consistent with its description, Material C wicked faster than Material B, but retained a smaller volume of aqueous solution without leaks than did Material B under the same test conditions.

According to the supplier, Material D was a nonwoven glass paper constructed from 6.5 µm electrical grade fibers of uniform length with a Polyvinyl Alcohol (PVOH) binder. The data sheet stated that the glass fiber was a continuous chop strand E-glass fiber. CRANEGLAS™ 230 sheets 0.102 to 0.381 mm thick were tested. All four sheets wicked 30 µl of sol-state 8 mg/ml MATRIGEL™ instantly or within 10 seconds. The percent weight of PVOH in the material composition was adjustable by the supplier, but not known for the samples tested. The wicking rate in 0.381 mm thick material was lower than in Materials A and B. Photographs of material after red-dye wicking and staining of the absorbent component followed by a 24-hour room temperature drying are shown in FIGS. 4E-4F. FIG. 4E shows Material D with a basis weight of 18 g/m$^2$ and caliper thickness of 0.102 mm at 7.3 PSI (TAPPI, T-411). FIG. 4F shows Material D with a basis weight of 41 g/m$^2$ and thickness of 0.229 mm at 7.3 PSI. In both samples, the PVOH was seen predominantly as a dye-stained coating on the glass fibers with fewer larger PVOH fibers than in Materials A and B. Staining showed that PVOH-coated glass fibers formed a 3D absorbent network which extended to all of material surfaces. The PVOH coating on the 381 µm-thick material did not solubilize in water during a 2-day immersion in a beaker in a 37° C. 5% $CO_2$ incubator. An amount of coating was solubilized at temperatures >70° C. during a 12-hour immersion in water in a beaker in a forced convection oven. The material wet strength was reduced and the material became weaker at several spots. However, a substantial amount of PVOH was solubilized during material boiling for 3 hours. At that point, glass fibers could no longer be held/bound together in some areas. This showed that for some commercial materials, steam autoclaving may reduce PVOH content.

Example 4

Alterations in Composition of Commercial and Engineered Hydrophilic, Absorbent, Rigid, 3D Substrates and Ramifications Thereof Alterations in the composition of pre-made commercial and engineered substrates provided for a means to further control wettability, wicking, absorbency, liquid holding capacity, sorption and release of molecules. Certain alterations such as steam autoclaving also served to render compositions usable with cell cultures. Exemplary alterations disclosed herein were done using Millipore G041 glass fiber conjugate pad (Material A in Example 3).

Reduction in Mass Fraction of Absorbent Component.

Mass content of PVOH was reduced without causing material to be fluffy or disintegrated using the following procedure: steam autoclaving at 130° C. for 45 minutes, followed by dry heating at 130° C. for 10 minutes, followed by drying for 1 hour (all in the autoclave). In the first run, this procedure removed approximately 1% of the material weight measured prior to autoclaving. The second run removed between 0.5% and 1%. Two cycles were sufficient to substantially reduce the length of approximately 1-mm long or longer PVOH binder fibers in the material. The remaining PVOH material remained predominantly confined to glass fiber junctions. This alteration provided for improved deep culture imaging when cells were embedded into the material, without significant loss in wicking, spreading, and holding properties during and after culture dispensing and routine culture transfer. When used in subsequent testing, G041 material which underwent two runs of the above autoclave steam sterilization, dry heating, and drying was referred to as G041-AH material.

Addition of Absorbent Content by Impregnation.

G041-AH material was impregnated (coated) with custom PVOH coatings. Two grades of polyvinyl alcohol (PVOH) were used: Sigma-Aldrich #363073 and #363103 with a molecular weight of 31-50 kDa and 146-186 kDa, respectively. Both grades were 87%-89% hydrolyzed and supplied as irregularly shaped particles measuring between 0.5 and 2.5 mm. At a concentration of 10% weight to volume, both grades swelled in water, forming enlarged irregularly-shaped chunks of hydrogel which were homogenized into liquid consistency under vigorous mechanical agitation without heat. For each grade, serial dilutions were performed to obtain 0.1%, 1%, 2%, 5% and 10% weight to volume PVOH solutions in water. Both grades in all dilutions were tested as coatings for G041-AH material by submerging 12.7 mm material disks, 3 samples per condition, into respective solutions for a period of 10 minutes, followed by air drying in the chemical fume hood. Under all conditions tested, this created thin, approximately sub-micron thick swellable coating on glass fibers (seen with dye staining) which was insoluble in water at 37° C. when stored in it for at least 1 day. Since coating dissolutions were not apparent at 37° C. in a 5% $CO_2$ incubator, PVOH insolubilization treatments known in the art were not done.

In subsequent wick and hold tests using water as the test medium, 1% weight to volume coating with Sigma-Aldrich #363073 produced the closest water wicking and hold results with respect to that of unaltered G041 material among 10 conditions tested. The 1% PVOH-coated G041-AH material was referred to as G041-AHC and used in further testing.

Differences in wicking between materials G041, G041-AH, and G041-AHC were tested daily for one week. Four samples per material were placed in respective Petri dishes and left uncovered to dry following testing. Daily, a 50 µl drop of DI water was delivered to each sample disk measuring 12.7 mm in diameter using standard micropipette. In the first week, material G041-AH was more hydrophilic and wicked faster than did the materials G041 and G041-AHC. Still, for all materials, the wicking of the 50 µl drop of DI water was fast and lasted less than 1 second. After 1 week and up to one month, tests were conducted twice weekly. All materials continued to wick the 50 µl drop of DI water within approximately 1 second. Wicking was the fastest for G041-AH material and the slowest for G041-AHC material. However, these differences became less pronounced at later time points, likely because uncovered glass became dirty, accompanied by an increase in its contact angle in material G041-AH. For up to 30 days, all materials held onto their 50 µl dispensed water content with no leaks. However, material drying rates at room temperature and the uptake of air moisture were different. For example, materials G041 and G041-AHC were still moist when material G041-AH became dry, consistent with lower PVOH mass fraction in material G041-AH.

Figure 5:
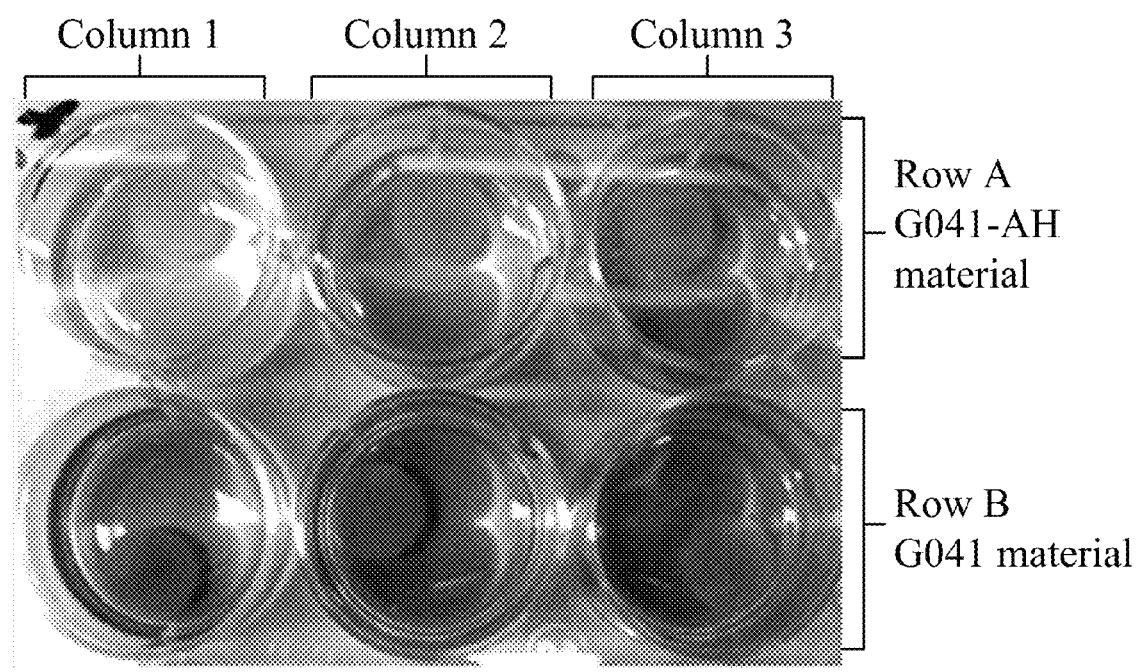
FIG. 5 shows slower rate of dye release from G041 material versus G041 material which underwent two cycles of steam sterilization, followed by heating and drying in the autoclave.
Figure 6:
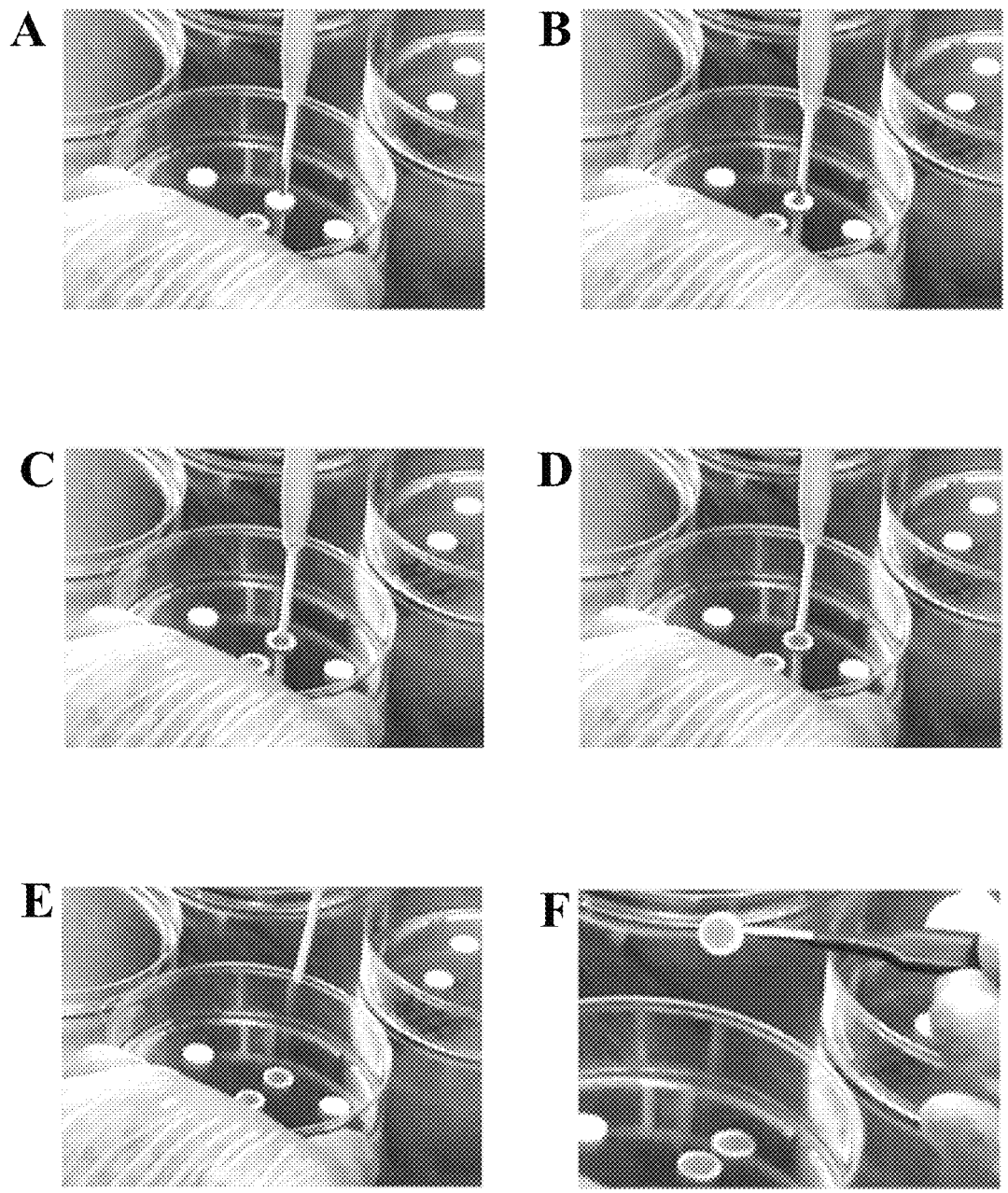
FIGS. 6A-6F contain a sequence of photographs showing delivery and wicking of 30 µl of chilled, Growth Factor Reduced MATRIGEL™ at 16 mg/ml protein in HBSS to 9.5 mm in diameter G041 material substrate disk using a positive displacement pipette and ice cold tips with a tip touching the substrate during delivery.

To confirm that G041 material retained water better than did G041-AH material of lower PVOH content, a release experiment was carried out. First, 12.7 mm in diameter disks (punched out of material which was left uncovered on a laboratory bench for 30 days) were placed in a 6-well plate. G041-AH samples were seated in Row A. G041 samples were seated in Row B. Next, 60 µl of brown food dye solution in DI water was delivered to all samples. All samples instantly wicked and retained the dye solution. Next, 2 ml of DI water was added to all 6 wells in the following order: Row A—Column 1, Row B—Column 1, Row A—Column 2, Row B—Column 2, Row A—Column 3, and Row B—Column 3. The samples started to release the dye. Thirty seconds after delivery of DI water to material sample seated in Row A—Column 1, 2 ml of water plus the leaked dye was aspirated from the wells in the same order in which DI water was previously added. Next, 2 ml of water was added to all wells in the same order. FIG. 5 shows what materials released after 2 minutes. Darker shades of liquid surrounding G041 samples seated in Row B and darker colored G041 material samples in the same row showed that material G041 released less dye during a previous wash step lasting approximately 30 seconds. Lighter shades of liquid surrounding the G041-AH samples seated in Row A and lighter colored G041-AH samples in the same row show that G041-AH material released most of the dye solution during the previous wash step. Hence, G041 material released absorbed dye solution slower than did material G041-AH, consistent with a higher mass fraction of PVOH in the former. Accordingly, the percent weight of absorbent and/or swelling materials in the absorbent rigid substrate composition influenced not only wetting, absorbency, and liquid holding capacity, but also sorption and release of molecules with important ramifications for mass transport in cell culture applications, cell-based assay development and the in vitro drug dosage form development.

The liquid holding capacity of G041 and G041-AH material sheets measuring 20 cm×30 cm was tested next to determine thresholds beyond which the materials could no longer spread and retain water. Prior to testing, materials were kept uncovered on a bench for 30 days under standard laboratory conditions. After 30 days, the materials were suspended horizontally in air using clips on a stand. Next, 300 µl of DI water was delivered to 3 locations on each sheet using a micropipette with the tip touching (but not pressing) the materials during dispensing. Both materials spread and held 300 µl of DI water. Next, 400 µl of DI water was delivered to 3 locations on each sheet. The material G041 spread and retained the water, while material G041-AH leaked. Using the same procedure with another 20 cm×30 cm sheet of G041 material (previously kept on a lab bench for 30 days), 500 µl of DI water was delivered at 3 locations. The material absorbed and retained the water with no leaks. Next, 600 µl of DI water was delivered at 3 locations and the material leaked. It was concluded that material G041 was more absorbent than was material G041-AH, consistent with lower content of absorbent PVOH material in the latter.

These tests were also done with G041 and G041-AHC material sheets. As with G041 material, G041-AHC material retained 500 µl of DI water but not 600 µl. However, the shape of the radial water spread differed between the two materials. The spread had a more uniform circular shape for material G041-AHC than for material G041, consistent with more homogeneous distribution of the PVOH material in the form of a coating (G041-AHC) rather than discrete PVOH fibers in G041 material composition.

Glass Cleaning Methods.

Improved wicking of G041-AH material relative to G041 during the first week was thought to result from glass fibers being more hydrophilic following steam autoclaving and dry heating, which initially cleaned glass and lowered its contact angle. To confirm this, additional 8 samples of G041-AH were prepared. Four samples were treated by UV in the biological safety cabinet by exposing each side to UV for 1 hour. The UV-treated samples which were referred to as G041-AHUV wicked even faster that did G041-AH samples. Since these samples had the same PVOH content, and the UV treatment could have only physically cross-linked PVOH to make it less absorbent, it was conjectured that improved wicking properties in G041-AHUV material were due to a cleaning effect, which further lowered glass contact angle and made it more hydrophilic (wettable), a necessary condition to initiate capillary wicking.

Accordingly, methods which made glass more "clean," as did steam autoclaving and UV irradiation, altered composition and properties of pre-made substrates and they wicked faster.

Example 5

Delivery, Embedding Methods, and Gradient Formation

For materials in Examples 2-4, delivery and embedding of sol-state ingredients including cell culture media and reagents, cells in any sol-state media normally used in cell culture applications (including sol-state hydrogels such as sol-state extracellular matrices), gels, and gelling or non-gelling polymer compositions, biomaterials, active or inactive biologicals, test agents, drugs, pharmaceutical compositions and biopharmaceuticals was done successfully by one or more of the following methods:

Spot-an-Ingredient.

In this method, spots of sol-state ingredients with or without cells were formed and embedded into the substrate by touching the substrate using a dispensing tool such as a pipet tip, followed by ingredient dispensing (using micropipette, for example), or by delivery of a drop without touching the substrate. Under all conditions tested, Material A (Example 3) 9.5 mm in diameter disk wicked sol-state ingredients commonly used in cell culture and pharmaceutical applications instantly or within 1 minute when delivered in 10 to 50 µl volume (see Example 6 and 7). The substrate wicking was not affected by the type of dispensing micropipette or any other tool used for dispensing. However, losses in pipetting were lower with positive displacement micropipette to dispense viscous solutions. FIGS. 6A-6F show substrate wicking during dispensing of 30 µl of chilled high protein concentration Growth Factor Reduced MATRIGEL™ (BD Biosciences Product No. 354263) at 16 mg/ml protein in HBSS. Sol-state MATRIGEL™ was delivered using a positive displacement pipette (Gilson Microman M100) and ice cold tips (Gilson CP100ST capillary pistons) with a tip touching the substrate during delivery. The substrate wicked dispensed gel within 1 minute and, typically, instantly. After dispensing, the substrate self-contained the gel, typically without leaks even though delivered volume was 1.15× the substrate void volume. When substrates were lifted for inspection, typically only condensation from a low-temperature gel was seen in a Petri dish under the substrate.

Photographs were taken of 9.5 mm in diameter, G041 material substrate showing the holding of wicked sol-state MATRIGEL™ embedded in the substrate. (Data not shown.) These photographs showed the front and back view of substrates after delivery of 30 µl of 16 mg/ml ice-cold MATRIGEL™ (top row substrates) and 8 mg/ml ice-cold MATRIGEL™ (bottom row substrates) using a positive displacement micropipette. The photographs also showed the front and back view of the substrates after delivery of 30 µl of 8 mg/ml ice-cold MATRIGEL™ using a standard micropipette. The photographs further showed the front and back view of the substrates which wicked ice-cold 8 mg/ml MATRIGEL™ by partial immersion in the said solution. The photographs still further showed the front and back view of the substrates which wicked ice-cold 8 mg/ml MATRIGEL™ by full immersion in the said solution.

Accordingly, these photographs showed the front and back views of the substrates 30 minutes after delivery of 16 mg/ml MATRIGEL™ (top row substrates) and 8 mg/ml MATRIGEL™ (bottom row substrates) using a positive displacement pipette. The photographs further showed the front and back view of the substrates 30 minutes after delivery of 8 mg/ml protein concentration MATRIGEL™ using a regular micropipette. This showed that substrates uniformly wicked (at a fast rate) and self-contained such high protein concentration (8-16 mg/ml MATRIGEL™) extracellular matrix delivered using standard laboratory tools. Formed spots of 3D-embedded extracellular matrix were uniformly distributed within the substrate thickness as seen by embedded MATRIGEL™ presence at the substrate top and bottom (data not shown).

Wick-an-Ingredient.

In this method, substrate was partly inserted and immersed into solution with or without cells which the substrate wicked. As shown in FIGS. 7A-7H, Material A (Example 3) 9.5 mm-diameter disk was inserted into the conical tube containing sol state 8 mg/ml MATRIGEL™ such that typically under 30% of the substrate volume was immersed into the solution. The substrate wicked sol-state gel until it was saturated (within 1 minute and typically under 30 seconds). Further, the substrate self-contained wicked MATRIGEL™ content when placed in a Petri dish (no leaks) as seen in the substrate front and back view (data not shown).

Dip-In Method.

In this method, substrate was entirely immersed into the solution with or without cells which the substrate wicked until it was saturated. Material A (Example 3) 9.5 mm diameter disk was immersed into the conical tube containing sol state 8 mg/ml MATRIGEL™ which it wicked until it was saturated in a period that lasted less than 30 seconds. The substrate further self-contained wicked and embedded gel since there was no gel spill into the Petri dish into which the substrate was transferred to after dip-in MATRIGEL™ embedding. This method allowed one to embed cultures, polymers, or other ingredients in high throughput without any special equipment by simply dipping a plurality of substrates into a reservoir-containing solution. As shown in Example 6, this method allowed even highly viscous polymers which could no longer be dispensed using micropipette to be uniformly embedded into the substrate.

All disclosed methods provided for substrate-to-substrate consistent and reproducible embedding of different ingredients, including those which were difficult to dispense in Examples 6 and 7. The substrates further allowed ingredients to have a defined shape and volume in x, y and z which was advantageous for seeding cells in 3D cultures, agent and polymer embedding, in vitro dosage form development, and quality control testing of biomaterials, active or inactive biologicals, pharmaceuticals, etc. The substrates further provided for consistent uniformity of ingredient distribution within the substrate volume for reproducible experimentation.

Figure 7:
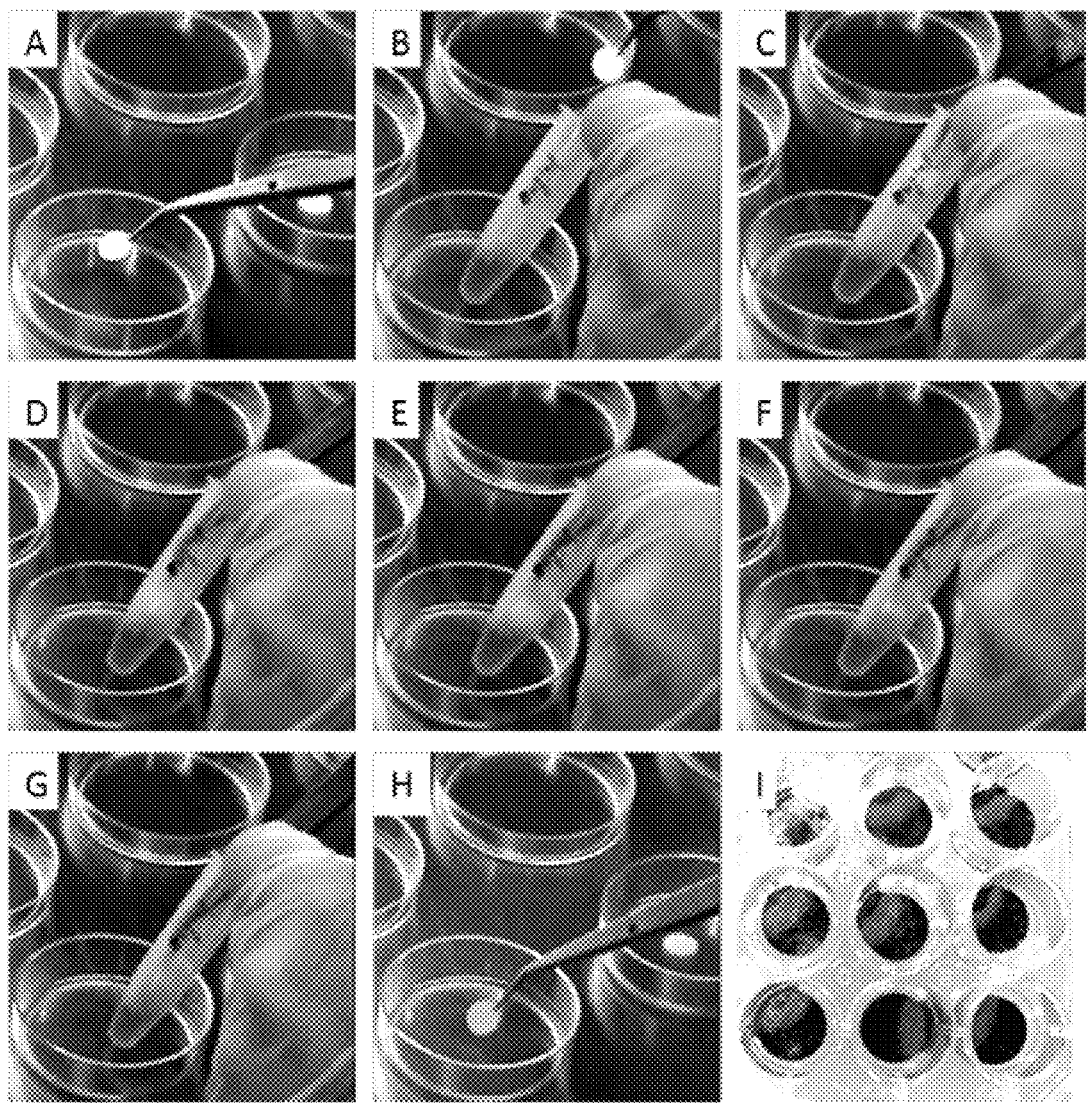
FIGS. 7A-7H are photographs showing delivery and wicking of 30 µl chilled, GFR MATRIGEL™ at 16 mg/ml protein in HBSS to 9.5 mm in diameter G041 substrate disk using a positive displacement pipette and ice cold tips with a tip touching the substrate during delivery.
FIG. 7I shows gradients formed in the substrates by wicking one or more different ingredients/molecules.

The main difference between "spots" and "dips" was the embedded volume of ingredients. In the dip-in method, the substrate was entirely immersed into the ingredient and, therefore, saturated. The spot-an ingredient method (such as spot-a-culture, spot-a-gel or spot-a-drug approach) formed spots of embedded ingredients, wherein the volume of said ingredient did not have to saturate the substrate. A plurality of spots had also been formed in a single substrate and the substrate was saturated or not. In the wick-in method, the substrate did not need to be saturated. For example, rigid absorbent materials were cut into strips and one side wicked an ingredient, but only over the part of the strip length, while the remaining length of the strip stayed dry. In another example, one side of the strip wicked one ingredient and the other side wicked another ingredient so as to form a gradient across the length of the strip. As shown in FIG. 7I, disk-shaped substrates partly wicked one ingredient and then wicked another ingredient, thus forming a gradient of one or more ingredients.

A gradient of one more ingredients was further formed using a variety of means, for example, (a) by using different substrate shapes and exposing one or more sides of the said shape to one or more ingredients; (b) by substrate overlap, wherein substrates self-contained different dye concentrations prior to being partly or entirely overlapped such that molecules contained in different substrates diffused predominantly in the z-direction through the thickness of overlapped substrates; (c) by spotting a plurality of ingredients onto a single substrate; or (d) by combinations of the above.

Accordingly, this made the disclosed delivery and embedding methods amenable to gradient formation. Following delivery, substrate-bound materials had also been further processed (e.g., dried) and further used.

Example 6

Embedding of Molecules, Gels, and/or Polymer Compositions for Different Applications Materials in Examples 2-4 were found suitable for embedding, release, or retention of molecules and polymers used in cell culture applications; biomaterials; extracellular matrix barriers for invasion, chemo-invasion and angiogenesis assays; drugs, drug delivery and drug release formulations; biopharmaceuticals; active and inactive biologicals, etc. Unless written otherwise, the below listed ingredients (suitable for embedding of molecules) formed gels in 9.5 mm-diameter substrates punched out of Millipore G041 glass fiber conjugate pad (Material A in Example 3) and steam autoclaved at 126° C. for 45 minutes:

| Ingredient label | Supplier and Product No. |
| --- | --- |
| Bovine Collagen Type I | BD Biosciences Product No. 354231 |
| GFR MATRIGELTM, extracellular matrix secreted by Engelbreth-Holm-Swarm (EHS) mouse sarcoma cells | BD Biosciences Product No. 354263, Growth Factor Reduced MATRIGELTM, high protein concentration stock |
| Type A gelatin, acid cured tissue | Sigma-Aldrich Product No. G1890 |
| Type B gelatin, lime cured tissue | Sigma-Aldrich Product No. G9382 |
| SeaPrep Agarose | Lonza Rockland Product. No. 50302 |
| Low viscosity Sodium Alginate | FMC Biopolymer Product No. Keltone LVCR |
| High viscosity Sodium Alginate | FMC Biopolymer Product No. Keltone HVCR |
| Methylcellulose, semi-solid medium | Sigma Aldrich Product No. M0387 |
| Pluronic F127 | Sigma-Aldrich Product No. Pluronic F-127 |
| Carbomer Homopolymer Type A | Lubrizol Product No. Carbopol 971P NF |
| Carbomer Homopolymer Type B | Lubrizol Product No. Carbopol 974P NF |

Corresponding solutions were made by following manufacturer instructions and most commonly by stirring a weighed amount of ingredient to dissolve it in a suitable medium using a magnetic stirrer with or without heat over prolonged periods of time until a homogeneous mixture formed. The following solutions were made:

| Ingredient label | Weight to volume ratio, or % w/v | Source/origin/derived from/produced by |
| --- | --- | --- |
| Bovine Collagen Type I | 2.9 mg/ml protein as supplied | Natural, animal, extracellular matrix (ECM) |
| GFR MATRIGELTM | 16 mg/ml protein in HBSS | Natural, animal, extracellular matrix (ECM) |
| Type A gelatin, porcine skin | 2% aqueous solution | Natural, animal, procine skin |
| Type B gelatin, bovine skin | 2% aqueous solution | Natural, animal, bovine skin |
| SeaPrep Agarose | 2.5% in HBSS (Hank's Balanced Salt Solution) | Natural, non-animal, agar from cells walls of red algae |
| Low viscosity Sodium Alginate | 2% aqueous solution | Natural, non-animal, alginates from cell walls of brown algae |
| High viscosity Sodium Alginate | 2% aqueous solution | |
| Methylcellulose, semi-solid media | 2% aqueous solution | Natural, non-animal, cellulose |
| Pluronic F127 | 25% w/v solution in Neurobasal medium | Synthetic, PEO-PPO-PEO |
| Carbomer Homopolymer Type A | 2% aqueous solution | Synthetic, high MW polymers of acrylic acid |
| Carbomer Homopolymer Type B | 2% aqueous solution | |

For many sol-state ingredients delivered using spot-an-ingredient method, substrates were saturated by 50 µl of delivered sol-state ingredient and this volume was used for testing. Photographs of the substrates were taken, which instantly or within 1 minute wicked ingredients of animal origin (data not shown). More specifically, the photographs showed animal origin gels embedded into 9.5 mm in diameter, steam autoclaved, G041 material substrates. They showed embedded extracellular matrix Collagen I at 2.9 mg/ml protein and MATRIGEL™ at 16 mg/ml protein. The photographs further show substrates self-containing, 3D-embedded, gelled Type A and Type B gelatin, respectively. The photographs further showed gels formed by these ingredients. All ingredients were delivered to respective substrates via spot-an-ingredient method using a standard micropipette.hese photographs showed substrates self-containing, 3D-embedded, gelled extracellular matrix (ECM) constituent Collagen Type I, and ECM secreted by Engelbreth-Holm-Swarm mouse sarcoma cells, respectively. These sol-state gels were delivered by spot-an-ingredient method using micropipette. According to the supplier, Collagen (the main component of connective tissues and the most abundant protein in the ECM) gelled in solutions with as little as 0.5 mg/ml protein. The substrates wicked 2.9 mg/ml protein sol-state Collagen instantly or within 1 minute. This allowed seeding of one or more cells in sol-state Collagen at 37° C. (Collagen is used as 2D culture substrate by coating cellware disposables and for seeding cells on top or within Collagen with the objective of forming a 3D culture of cells). According to the supplier, GFR MATRIGEL™ had 61% Laminin, 30% Collagen IV and 7% Entactin ECM constituents. It gelled in solutions with as little as 3 mg/ml protein. The substrates wicked 16 mg/ml protein sol-state MATRIGEL™ instantly or within 1 minute. (MATRIGEL™ is used as a coating on 2D culture ware or as a gelled ECM for 3D cultures. It resembles the extracellular environment of many tissues and promotes and maintains differentiated phenotypes of many cell types.) As most ECM components degrade and many cell types need ECM in long term culture as they do not secrete their own, or exogenous ECM degrades before cells secrete their own, the use of the substrate to support 3D cultures comprising one or more cells in an ECM or other hydrogel has many advantages. Accordingly, the photographs that were taken showed that commonly used ECM components in 2D and 3D cell culture applications were successfully embedded in the substrates.

Hydrocolloidal materials derived from natural sources are fully or partially soluble in water and used as gelling agents in 3D cell culture applications. Commonly, these are protein-based or polysaccharide-based biomaterials. An example of gel derived from animal proteins is gelatin. Polysaccharide-based polymers represent a large class of biomaterials used in 3D cell culture applications including agarose, alginate, carageenan, dextran, chitosan, cellulose derivatives, etc. These biomaterials are also used in preparation of drug delivery systems (alginates, gelatins, etc.) and used as substrates for controlled drug release (agarose, cellulose derivatives, chitosan, etc.) among other applications. Rigid absorbent substrates allowed embedding of such sol-state gels while providing for a convenient 3D framework for cell culture studies, cell-based assay development, drug release studies and other applications.

The photographs referenced above further showed substrates self-containing, 3D-embedded, gelled Type A and Type B gelatin, respectively. They also showed said ingredients which formed gels in a Petri dish. Sol-state solutions were delivered at 37° C. using spot-an-ingredient method with an ordinary micropipette. The substrates wicked these solutions instantly or within 1 minute.

Photographs were also taken of the substrates self-containing, 3D-embedded, natural, non-animal derived semi-solid media (Methylcellulose) and hydrogels cross-linked (Agarose) or uncross-linked (Alginates) and their respective gels where applicable (data not shown). More specifically, these photographs were of steam autoclaved, 9.5 mm in diameter G041 material substrates comprising 3D-embedded, natural, non-animal derived, gelled hydrogels (Agarose), uncross-linked hydrogels (Sodium Alginates) and semi-solid media (Methylcellulose). In some of the photographs, agarose solution was delivered at 60° C. by standard pipette using spot-an-ingredient method. In the first two photographs, the agarose gel sample was prepared under identical condition. Sodium alginates of low viscosity and high viscosity were delivered using spot-an-ingredient method by a positive displacement pipette. In some photographs, methylcellulose was embedded into the substrate using dip-in method. Other photographs showed drops of methylcellulose (identical to that contained in the substrates in prior photographs) held almost vertical in a Petri dish to show viscoelasticity of the semi-solid medium.

The first set of photgraphs showed gelled SeaPrep Agarose delivered to the substrates in sol-state at a 60° C. solution temperature using spot-an-ingredient method with a standard micropipette. The solution was wicked instantly or within 1 minute and gelled fast when cooled to approximately 37° C. An amount of the corresponding gel, formed in a beaker, was transferred to a Petri dish and imaged. In its gelled state, agarose is used as a matrix for 3D cell aggregates (such as spheroids) and 3D cell cultures of dissociated cells. It melts at higher temperatures and gels at temperatures close to 37° C. This makes agarose suitable for cell-based assay development, molecular biology applications and drug release studies. For example, agarose is used as a matrix through which chemoattractants diffuse to study cell motility in the "agarose drop" assay, the "agarose plug" assay, and the "under agarose" assay.

The next set of photographs showed uncross-linked Sodium Alginates of low and high viscosity, respectively, embedded into the substrates. They were delivered using spot-an-ingredient method by a positive displacement micropipette and wicked within 1 minute. For higher viscosity alginate dip-in method was more appropriate. According to the supplier, a 2% low viscosity alginate solution and 1.25% high viscosity alginate solution had a viscosity of 100-300 cPs and 600-900 cPs, respectively. For high viscosity alginate, 2% solution was tested. For reference, water viscosity is about 1 cP and that of honey about 10,000 cPs. Alginates are used as polymer matrices for 3D cell cultures of dissociated cells and spheroids, or cells are encapsulated in alginate beads or microcarriers. Dipping or short-term incubation in a Calcium buffer at close to physiological conditions forms cross-linked gel with embedded cells. Sodium alginates tested are also used as extended release drug-polymer matrices (e.g., polymer matrices for tablets used in orally administered controlled drug delivery).

The third set of photographs showed, respectively, methylcellulose semi-solid medium embedded into the substrates and the drops of said medium held almost vertical in a Petri dish to show its viscoelasticity (1,500 cPs). Due to high viscosity and high gelling temperature, methylcellulose semi-solid medium rather than a gel is used for the culture of human cells, clonal cells, embryoid bodies, neurospheres, etc., and further used in assays such as methylcellulose-based colony forming assays and anchorage independence assays.

This and other cellulose ethers are used as excipients in drug formulations or sustained release of other biomolecules. In solid tablets, cellulose ethers enable a swelling-driven release of the drug in contact with physiological fluids.

Photographs were also taken of the substrates self-containing, 3D-embedded, synthetic gelled polymers (data not shown). More specifically, photographs were taken of steam autoclaved, 9.5 mm in diameter G041 material substrates self-containing, 3D-embedded, synthetic gelled polymers and their corresponding gels seated in a Petri dish. The first photograph showed Pluronic F-127 delivered to the substrates using positive displacement pipette with the corresponding gel shown in the second photograph. Pluronic F127 is the trade name for Poloxamer 407, a nontoxic copolymer used in 3D cell culture applications, in cell encapsulation, as a substrate in tissue engineering (e.g., cartilage), as a component in drug delivery and pharmaceutical formulations, as an additive to cell culture media in bioreactors, as a surfactant and reagent which facilitates solubilization of hydrophobic molecules in water, etc. Pluronic F127 forms gel at physiological temperatures at concentrations higher than approximately 20% w/v.

The next set of photographs showed Carbomer Homopolymers Type A and Type B, respectively, embedded into substrates using dip-in method with their corresponding gels. Carbomer Homopolymers Type A and Type B were embedded into substrates using dip-in method and compared to the corresponding gels (data not shown). Carbomers are high MW polymers of acrylic acid with widespread use in formulations for drug delivery. CARBOPOL® 971P NF is a lightly cross-linked polymer (more efficient in controlling drug release) whereas Carbopol 974P NF is a highly cross-linked polymer producing highly viscous gels with rheology similar to mayonnaise.

Disclosed exemplary naturally derived ingredients, synthetic or other ingredients and their combinations (often used in preparation of drug-polymer matrices) embedded in substrates provided for a convenient method for in vitro testing of drugs and drug release (or in vitro drug dosage form development and testing) with 3D cell cultures in configurations wherein, for example, one substrate contained a 3D cell culture and was overlapped by a substrate comprising extended release drug-polymer matrix or any other reagent (see for example, Brain Culture #5 in Example 9).

Example 7

Coatings

Materials in Examples 2, 3 and 4 were coated with diverse molecules used in 3D cell culture applications or otherwise. In addition to ingredients tested in Example 6, most of which coat the substrates in suitable concentration, the additional following ingredients were tested:

| Ingredient label | Concentration | Origin/source | Supplier; Product No. |
|---|---|---|---|
| Laminin | 1 mg/ml protein | Animal, ECM from EHS mouse sarcoma | Sigma-Aldrich; L2020 |
| Fibronectin | 2.5 mg/ml protein | Human, plasma | Life Technologies; 33016-015 |
| PDL Poly-D-Lysine | 100 µg/ml in DI water | Synthetic | Sigma-Aldrich; P7405 |
| PLO Poly-L-Ornithine | 100 µg/ml in DI water | Synthetic | Sigma-Aldrich; P4957 |

Solutions were delivered by a micropipette using spot-an-ingredient method in 50 µl volume to 9.5 mm in diameter substrates punched out of Material A in Example 3, and steam autoclaved at 126° C. for 45 minutes prior to solution delivery. All solutions were wicked instantly or within 10 seconds, with the exception of high molecular weight PDL (>300 kDa, Sigma-Aldrich Product No. P7405), which was wicked within 5 seconds to 1 minute. Photographs were taken of steam autoclaved, 9.5 mm in diameter, G041 material substrates self-containing molecules they are being coated with (data not shown). These molecules are used in cell culture applications for the coating of planar cellware disposables including Laminin, Fibronectin, Poly-D-Lysine, and Poly-L-Ornithine. The photographs showed these sol-state solutions self-contained in the substrates. Lower molecular weight PDL polymers suitable for cell culture (not shown) were normally wicked instantly or within 10-30 seconds (30-70 kDa polymer and 70-150 kDa polymer at 100 µg/ml, Sigma-Aldrich P7886 and P0899, respectively).

All of the above coatings are normally used to coat commercial cellware disposables or the disposables are sold pre-coated with the above ingredients in order to promote cell adhesion to planar plastic surfaces and for other reasons, for example, to maintain differentiated cell function or to promote cell survival, growth and proliferation. Out of the ingredients tested in Examples 6 and 7, MATRIGEL™ was used as a gelled extracellular matrix in a 3D cell culture of brain cells and hepatic cells and as a coating in a 3D cell culture of brain and hepatic cells; Poly-D-Lysine was used as coating in 3D cell culture of brain, hepatic, and osteoblastic cells; and Fibronectin (Sigma Aldrich Product No. F-1141 at 20 µg/ml in DI water) was used as a coating in a 3D cell culture of osteoblastic cells shown in the later Examples.

Notably, MATRIGEL™ gels at 3 mg/ml protein or higher. If cells are suspended in gelling MATRIGEL™, they are encapsulated in 3D when MATRIGEL™ gels. Cells can also be seeded in a lower protein concentration MATRIGEL™. When cells were seeded in a gelled extracellular matrix, the MATRIGEL™ was at a 1 mg/ml concentration. At this concentration, MATRIGEL™ did not gel but made the whole cell suspension viscous and sticky so it stuck cells to the substrate. MATRIGEL™ can also be used as a coating. In this approach normally 0.5-1 mg/ml protein MATRIGEL™ was used to coat substrate before seeding cells. The cells were then seeded in medium in a MATRIGEL™ coated substrate. It is very different if MATRIGEL™ is used as a gel and as a coating. In the former, most cell surface is surrounded by this extracellular matrix. In the latter, only where the cell touches the substrate it contacts this ECM—the rest of the cell body is exposed directly to medium (or other cells).

Example 8

Spheroids and Spread 3D Cultures of Multipotent Stem Cells (Neural Progenitor Cells)

"Neurospheres" (spheroids of multipotent stem cells) and their spread 3D cultures (at later time points in culture) were cultured in steam-autoclaved (126° C. for 45 minutes) 9.5 mm in diameter substrates punched out of Millipore G041 material. Cells from lateral ganglionic eminence of E-18 rat were seeded using spot-an-ingredient method into the substrates seated in the 24-well plate and cultured in a humidified 5% $CO_2$ 37° C. incubator. The medium composition was Neurobasal+2% B-27+1% G-5+0.5 mM Glutamax+0.1% bFGF. Medium was not changed other than to account for evaporative losses for up to 5 days in culture, and every day bFGF was added at 0.1% to medium in each well comprising substrate. For culturing beyond 5 days, half the medium was renewed. At the end of culturing period, cultures were stained by Calcein AM, which intracellularly labeled live cells, and Hoechst 33342, which labeled nuclei of all cells blue. Culture viability at any time of imaging and for all cultures was greater than 90%. The following seeding and culturing conditions were tested:

| NPC Culture | Cell conditions at seeding | Conditions at seeding | Substrate coating |
|---|---|---|---|
| #1 | 1 X passaged cells seeded as single cells and spheroids | $10^5$ cells/substrate seeded in 60 μl medium | none |
| #2 | 1 X passaged cells seeded as single cells and spheroids | $10^5$ cells/substrate seeded in 60 μl medium | PDL 100 μg/ml Sigma P4957 |
| #3 | Harvested cells were seeded into a stack of 2 substrates per well | About 1/8 of cells per hemisphere buldge were seeded | none |

Figure 8:
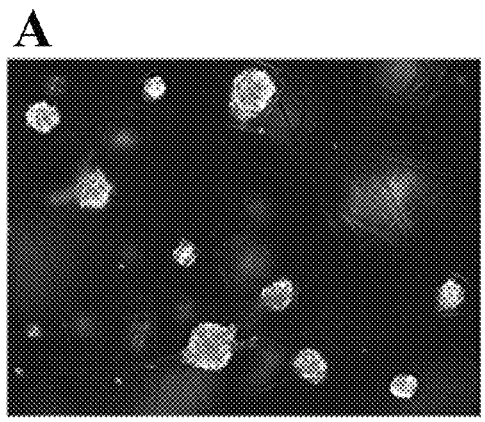
FIG. 8 contains fluorescence micrographs of Calcein AM/Hoechst 33342 labeled multipotent stem cells cultured in steam autoclaved G041 substrates. Cells were passaged once and seeded as single cells and up to 5-10 cells in diameter spheroids.
Figure 8:
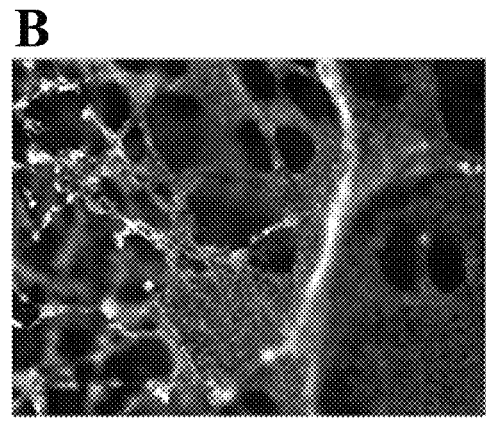
Figure 8:
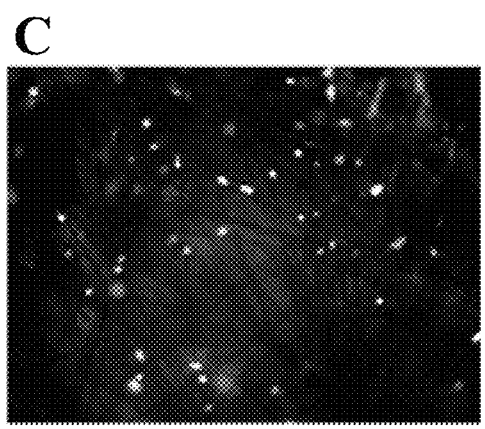
Figure 8:
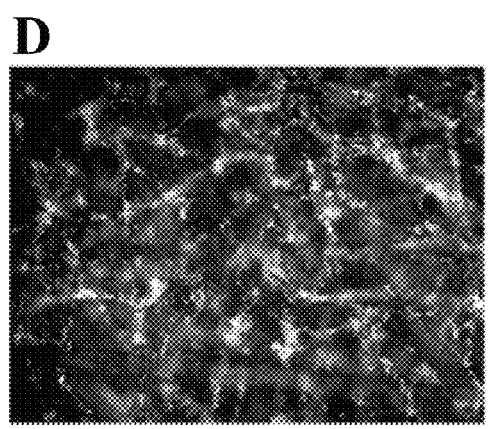
Figure 8:
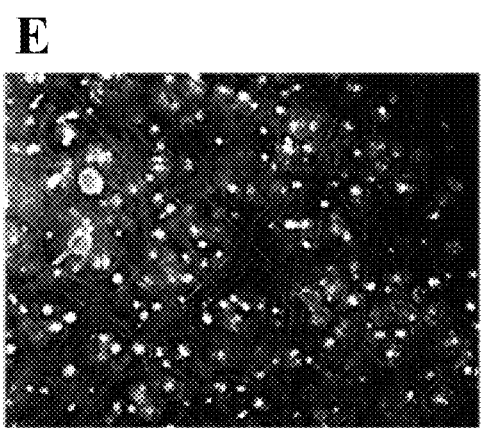
Figure 8:
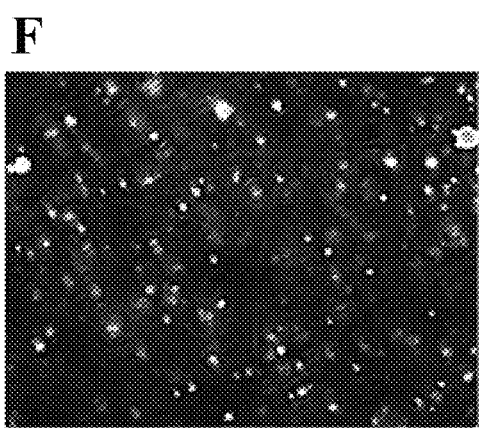

Long-term culture of undifferentiated stem cells is important for many applications, including cell based therapies. In an undifferentiated state these cells form spheroids. When committed to a specific cell type (e.g., neuron, astrocyte or oligodendrocyte), seeded cells spread because in a differentiated state these cells normally do not form spheroids in culture. NPC Cultures #1 and #2 were seeded as a population of single cells and spheroids. Seeded spheroids typically measured less than 5-10 cells in diameter. By day 3 in culture, cells remained in spheroids only within uncoated substrates (FIG. 8A). In PDL-coated substrates, cells were typically spread (FIG. 8B) forming a 3D cell culture with fewer spheroid aggregates. Out of six cultures in PDL-coated substrates, two still had spheroids while the rest had fewer spheroids and formed a 3D-distributed cell culture through the full substrate thickness as shown in FIGS. 8C-8D, respectively. FIGS. 8C-8D show the bottom of the substrate after the culture was flipped using tweezers in order to image its bottom side and confirm that cells were present throughout the substrate. In control cultures, cells seeded under identical conditions in wells of an uncoated 24-well plate had a planar layer of cells on or before day 3 for a given cell seeding density. In contrast, as shown by the top and bottom view of cultures in uncoated substrates, FIGS. 8E-8F, respectively, spheroids were still present and present in large numbers after day 4 in culture. This point demonstrated that the substrate was able to sustain cell spheroids at cell seeding densities at which planar cultures could no longer do so.

Figure 9A:
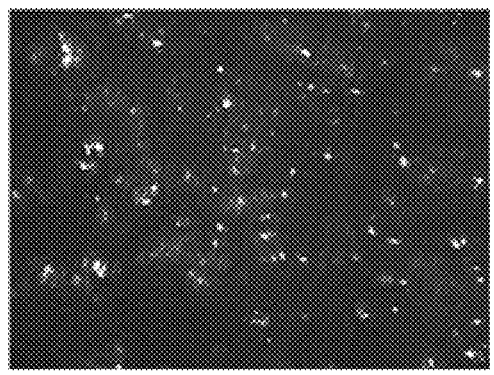
FIGS. 9A-9C are 4× images of spheroids after 3, 4 and 6 days in culture, respectively, showing spheroid growth (x=3 mm, y=2.25 mm).
Figure 9B:
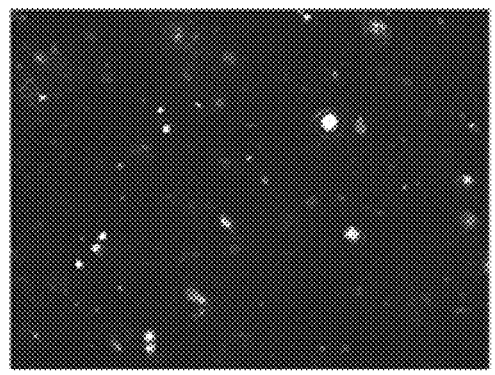
Figure 9C:
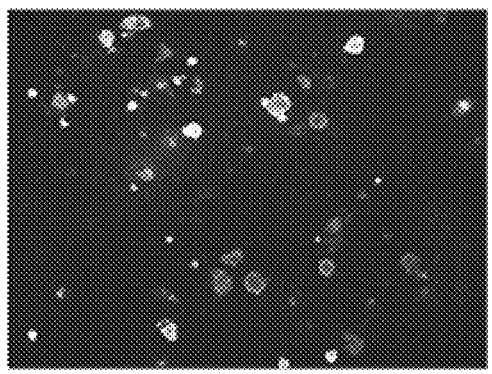
Figure 9D:
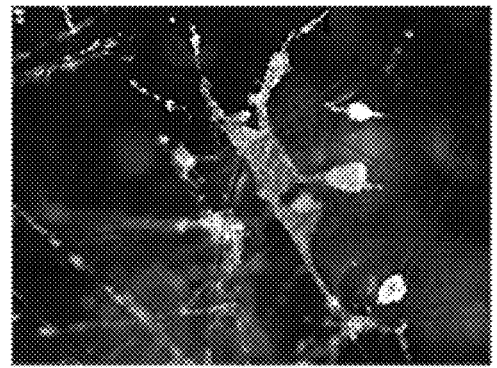
FIG. 9D is a 10× (x=1.18 mm, y=0.88 mm) image of neural progenitor cell seeded into uncoated substrates cultured for 10 days, at which time some but not all spheroids spread, forming differentiated 3D culture of cells.

In NPC Culture #3, multipotent stem cells were seeded in two overlaid substrates right after harvest/dissociation. The cells were not passaged prior to seeding and there were no spheroids at seeding. Cells aggregated, formed spheroids of relatively uniform size, and grew in spheroids up to approximately 1 week in culture (FIGS. 9A-9C). Beyond 1 week in culture, some but not all spheroids started to spread and merge. By day 10 in culture, while spheroids were still present, cells formed 3D-distributed cell culture as shown in FIG. 9D.

Taken together, the data demonstrated that substrates and overlaid substrates provided a suitable platform to aggregate multipotent stem cells into a large population of spheroids suspended within the substrates without any rotary, rocking or shaking equipment and at cell seeding densities at which cells spread on planar substrata after a few days in culture.

Example 9

Brain 3D Cell Cultures

Brain 3D cell cultures were cultured in 9.5 mm in diameter substrates punched out of Millipore G041 glass fiber conjugate pad (Material A in Example 3). The substrates were sterilized by steam autoclaving at 126° C. for 45 minutes prior to use with cells for the below Brain Cultures #1 through #5, and by UV irradiation for Brain Cultures #6 and #7. Cells were seeded using spot-an-ingredient method and cultured in uncoated and PDL-coated substrates, and without or with gelled GFR MATRIGEL™ in a humidified 5% $CO_2$ 37° C. incubator. The following seeding and culturing conditions were tested:

| Brain Culture | Cell types in culture at seeding | Sol-state suspension in which cells were seeded | Substrate coating |
|---|---|---|---|
| #1 | 2:1 cell ratio of neurons: mixed glia | Medium | PDL 100 μg/ml |
| #2 | 2:1 cell ratio of neurons: mixed glia | 7.5 mg/ml GFR MATRIGEL™ | none |
| #3 | mixed glia: astrocytes and microglia | 3.75 mg/ml GFR MATRIGEL™ | none |
| #4 | mixed glia: astrocytes and microglia | 3.75 mg/ml GFR MATRIGEL™ | PDL 100 μg/ml |
| #5 | mixed glia: astrocytes and microglia | 3.75 mg/ml GFR MATRIGEL™ | none |
| #6 | 1:1 cell ratio of neurons: astrocytes | 8 mg/ml GFR MATRIGEL™ | none |
| #7 | 1:1 cell ratio of neurons: astrocytes | 8 mg/ml GFR MATRIGEL™ | PDL 100 μg/ml |

Brain Culture #1.

Mixed cultures of E-18 harvested primary cortical neurons and P0-harvested and 1× passaged mixed glia (astrocytes and microglia; about 15% microglia in total glia) were seeded at $4 \times 10^6$ cells/ml in 30 µl volume into 100 µg/ml PDL-coated substrates seated in the wells of a 48-well plate. During the first 3 days in culture, the medium composition was Neurobasal+2% B-27(-AO)+1% G-5+0.5 mM Glutamax. At day 4, the medium composition was changed to Neurobasal+2% B-27(-AO)+0.5 mM GlutaMAX. Cultures were fed every 2-3 days by exchanging half the medium. After 1 week in culture, cells were stained and imaged on Nikon Eclipse 80i at 10× as shown in FIG. 10A.

Brain Culture #2.

Figure 10:
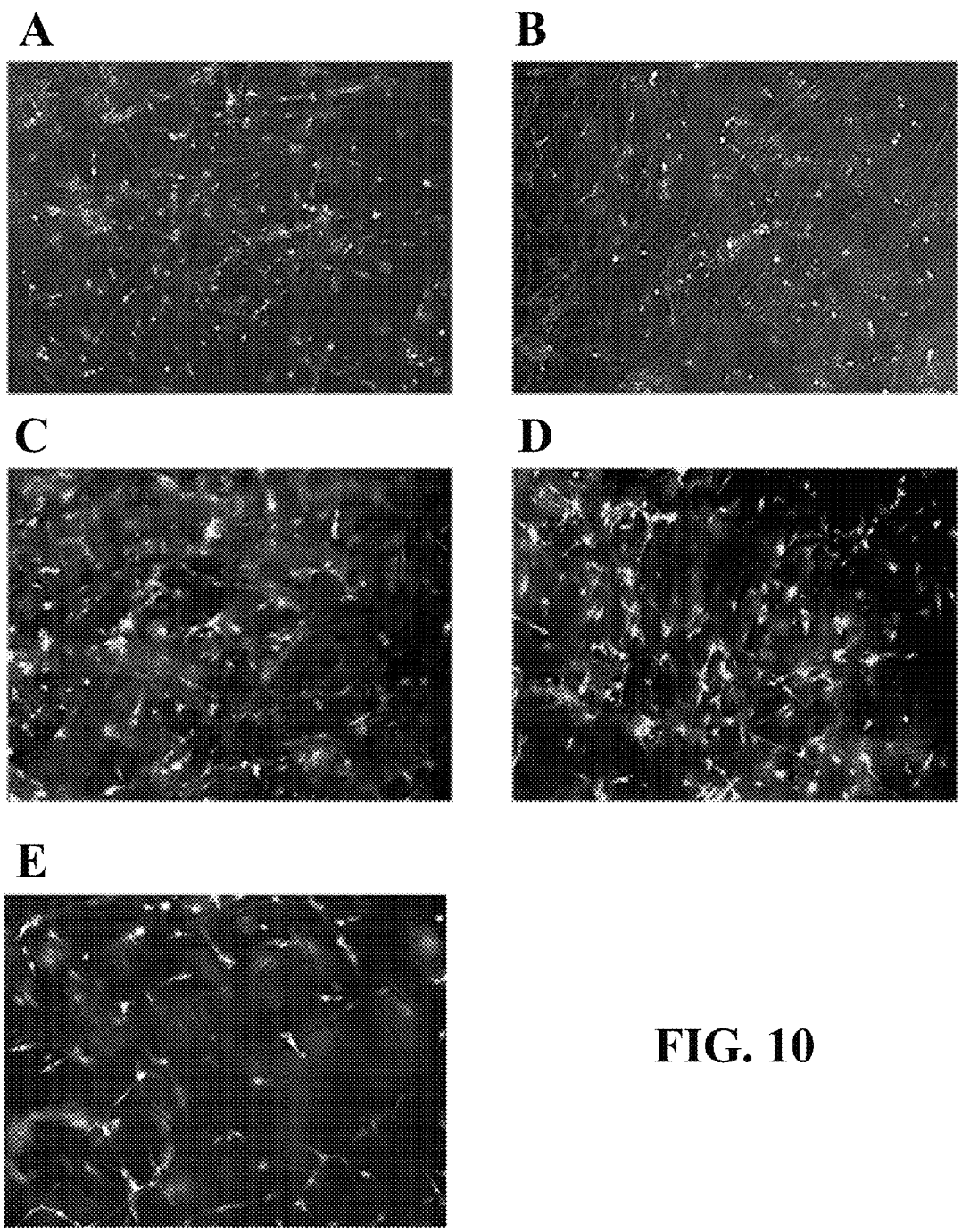
FIG. 10 comprises fluorescence micrographs of brain 3D cultures cultured in steam-autoclaved G041 substrates, labeled and imaged on Nikon Eclipse 80i at 10× (x=1.18 mm, y=0.88 mm).

In these cultures, delivery and culturing conditions were the same as with the Brain Culture #1 with the exception that cells were seeded in 7.5 mg/ml sol-state GFR MATRIGEL™ into uncoated substrates and cultured for 2 weeks and then stained and imaged (FIG. 10B).

Brain Culture #3.

P0-harvested and 1× passaged mixed glia (astrocytes and microglia) were seeded at $2.5 \times 10^6$ cells/ml in 45 µl volume in 3.75 mg/ml GFR MATRIGEL™ into uncoated substrates seated in the wells of a 48-well plate. The medium composition was DMEM/F-12+10% FBS. After 1 day in culture, cells were stained by live cell stains and imaged using Nikon Eclipse 80i at 10× as shown in FIG. 10C.

Brain Culture #4.

In these cultures, delivery and culturing conditions were the same as with the Brain Culture #3 with the exception that 30 µl of MATRIGEL™ sol-state cell suspension was seeded into PDL-coated substrates. After 1 day in culture cells were stained and imaged (FIG. 10D).

Brain Culture #5.

In these cultures, delivery and culturing conditions were the same as with the Brain Culture #4 with the exception that cultures were seeded into PDL-coated substrates and cultured in serum-free DMEM/F-12 medium for 1 week without media exchange. Next, the medium was aspirated and another substrate comprising DMEM/F-12 in 3.75 mg/ml GFR MATRIGEL™ was placed on top of the substrate containing culture; no additional media was added. Said overlaid substrates were then transferred to an incubator for another 3-day culturing. After 10 days in culture, the top substrate was removed and cells cultured in the bottom substrate were stained and imaged as shown in FIG. 10E. FIG. 10E confirms that although cells were deprived of free (substrate-unbound and gel-unbound) medium, cell morphology was round, cells extended long processes, and cells used the substrate to form 3D cell networks. These cultures showed that cells may be deprived of medium for a period of time if embedded in a hydrogel in the substrate when a hydrogel and the absorbent substrate "trapped" medium were overlaid by another absorbent substrate with a hydrogel (both of which previously absorbed medium), and cultured in a humidified incubator. This is significant as it enabled setup of diffusion assays with 3D cell cultures using overlaid rigid absorbent substrates wherein at least one substrate comprised substrate-bound or substrate+hydrogel bound test agent and at least one substrate comprised cells or cells in a hydrogel.

Brain Culture #6.

Figure 11:
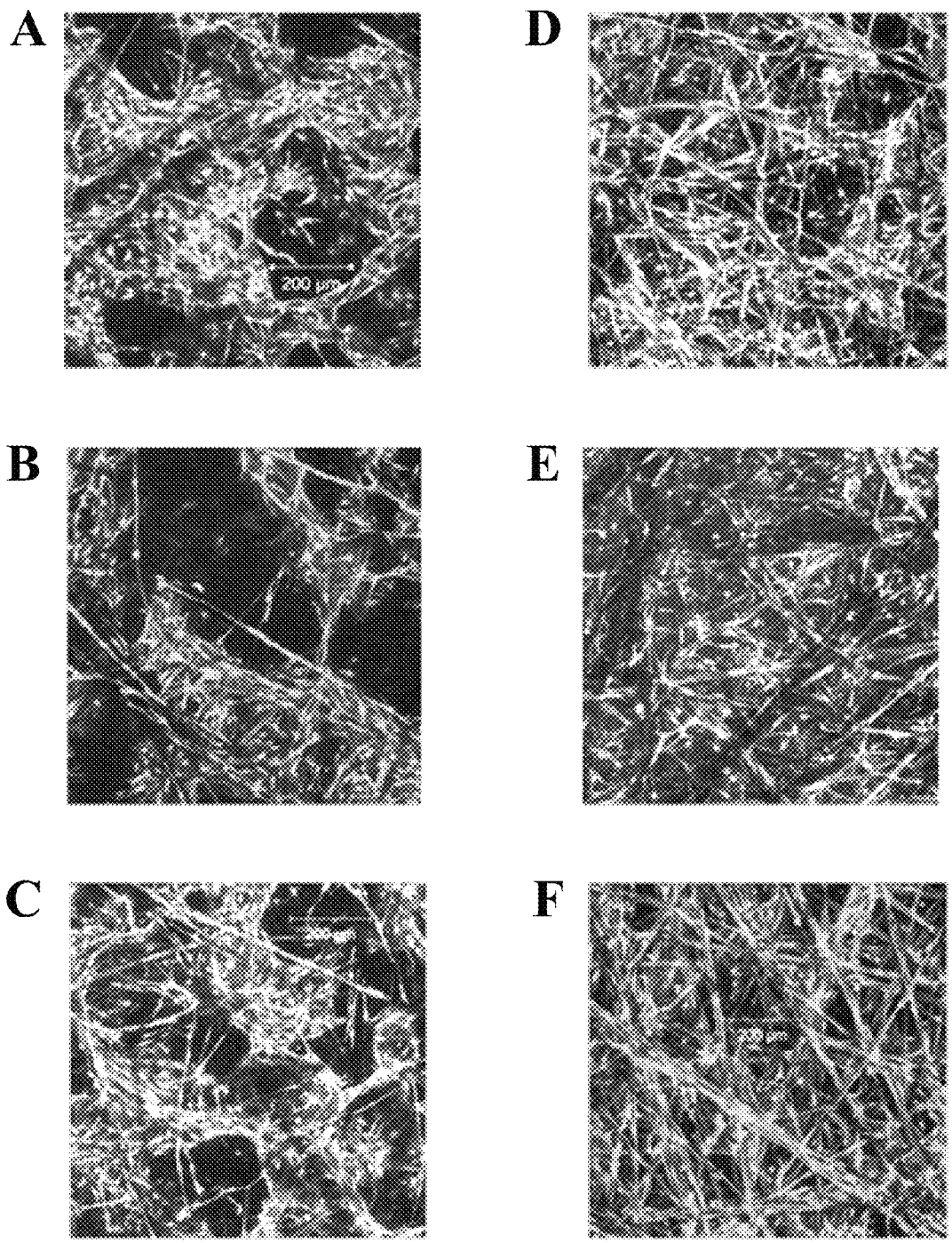
FIG. 11 contains z-stacked fluorescence confocal micrographs of brain 3D cultures through their full thickness of 400 μm, cultured in UV sterilized G041 substrates. Mixed cultures of neurons and astrocytes in 8 mg/ml MATRIGEL™ were cultured in uncoated (FIGS. 11A-11C) and PDL-coated (FIGS. 11D-11F) substrates. After 10 days in culture, MATRIGEL™ was stained by Calcein Blue, live cells labeled by Calcein AM and dead cell nuclei labeled by Ethidium Homodimer-1 and imaged with Zeiss LSM 510 with three-channel excitation at 10× (x=898.24 μm, y=898.24 μm. A few dead cells were found.
Figure 12:
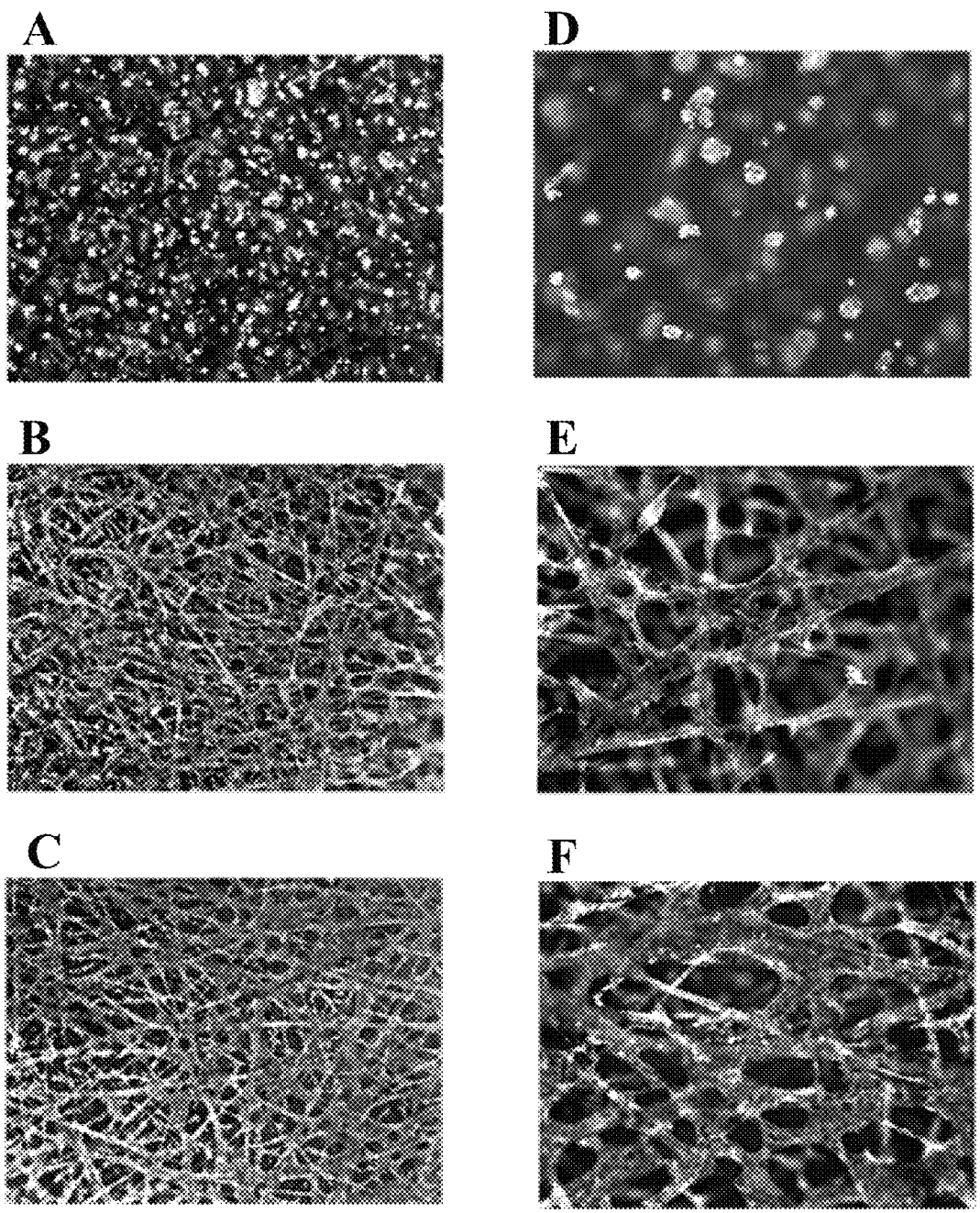
FIG. 12 comprises fluorescence micrographs of Calcein AM labeled HepG2 liver 3D cultures seeded in 3.75 mg/ml GFR MATRIGEL™ into steam-autoclaved and then PDL-coated substrates, cultured and then imaged on Nikon Eclipse 80i. Images A, B, and C designate magnification of 4× (x=3 mm, y=2.25 mm) and images D, E, and F designate magnification of 10× (x=1.18 mm, y=0.88 mm). Images A and D correspond to the day of imaging after 4 days in culture, images B and E correspond to the day of imaging after 9 days in culture, and images C and F correspond to the day of imaging after 26 days in culture.
Figure 13:
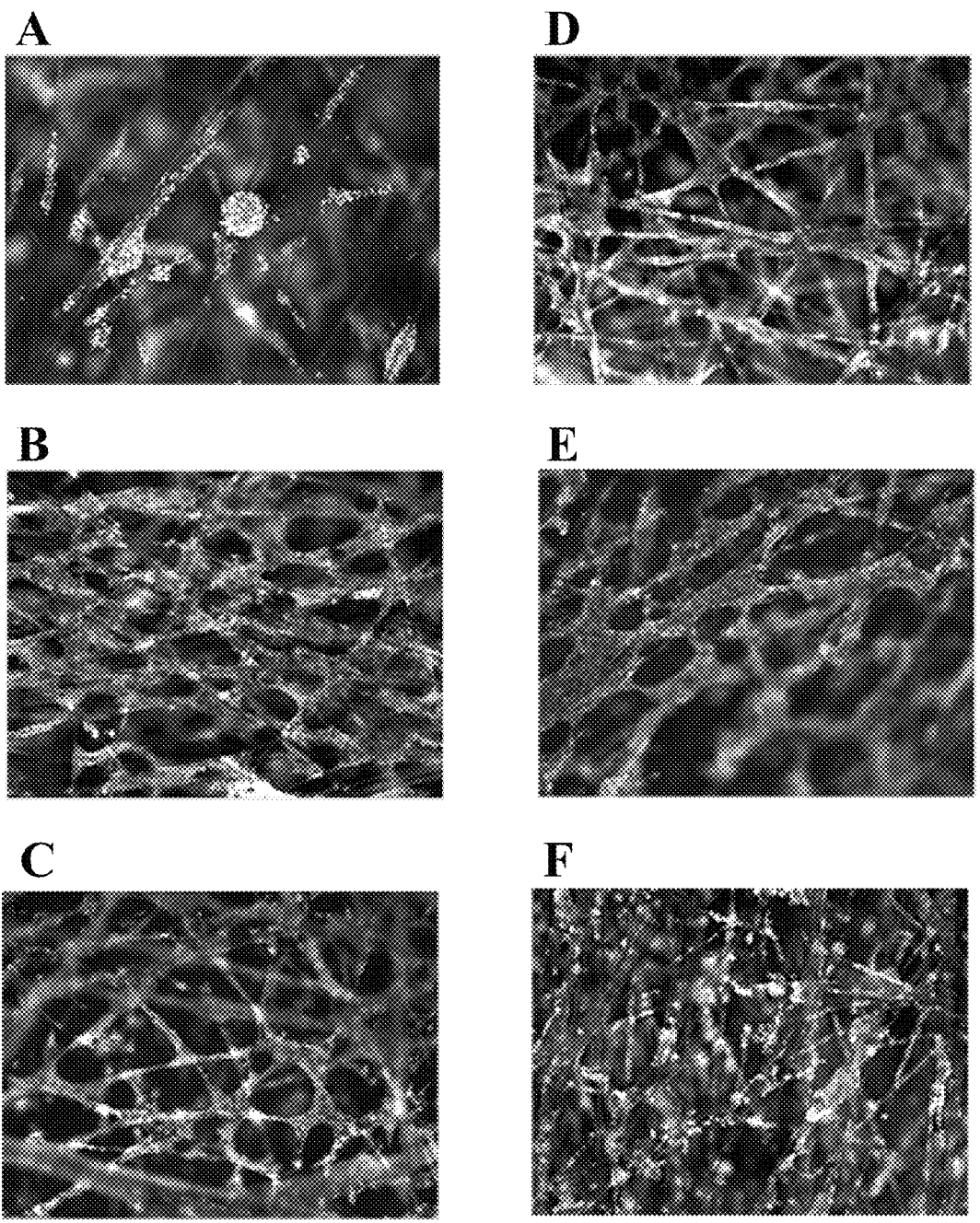
FIG. 13 contains 10× (x=3 mm, y=2.25 mm) fluorescence micrographs of Calcein AM labeled HepG2 liver cells 3D cultured in gelled or ungelled GFR MATRIGEL™ in steam-autoclaved G041 substrates. Images A, B, and C designate cultures seeded in 3.75 mg/ml MATRIGEL™, which gelled. Images D, E, and F designate cultures seeded in 1 mg/ml MATRIGEL™, which formed a coating. Images A, B, and C correspond to the day of imaging after 4, 9 and 26 days in culture, respectively. Images D, E, and F correspond to the day of imaging after 5, 24 and 30 days in culture.
Figure 14:
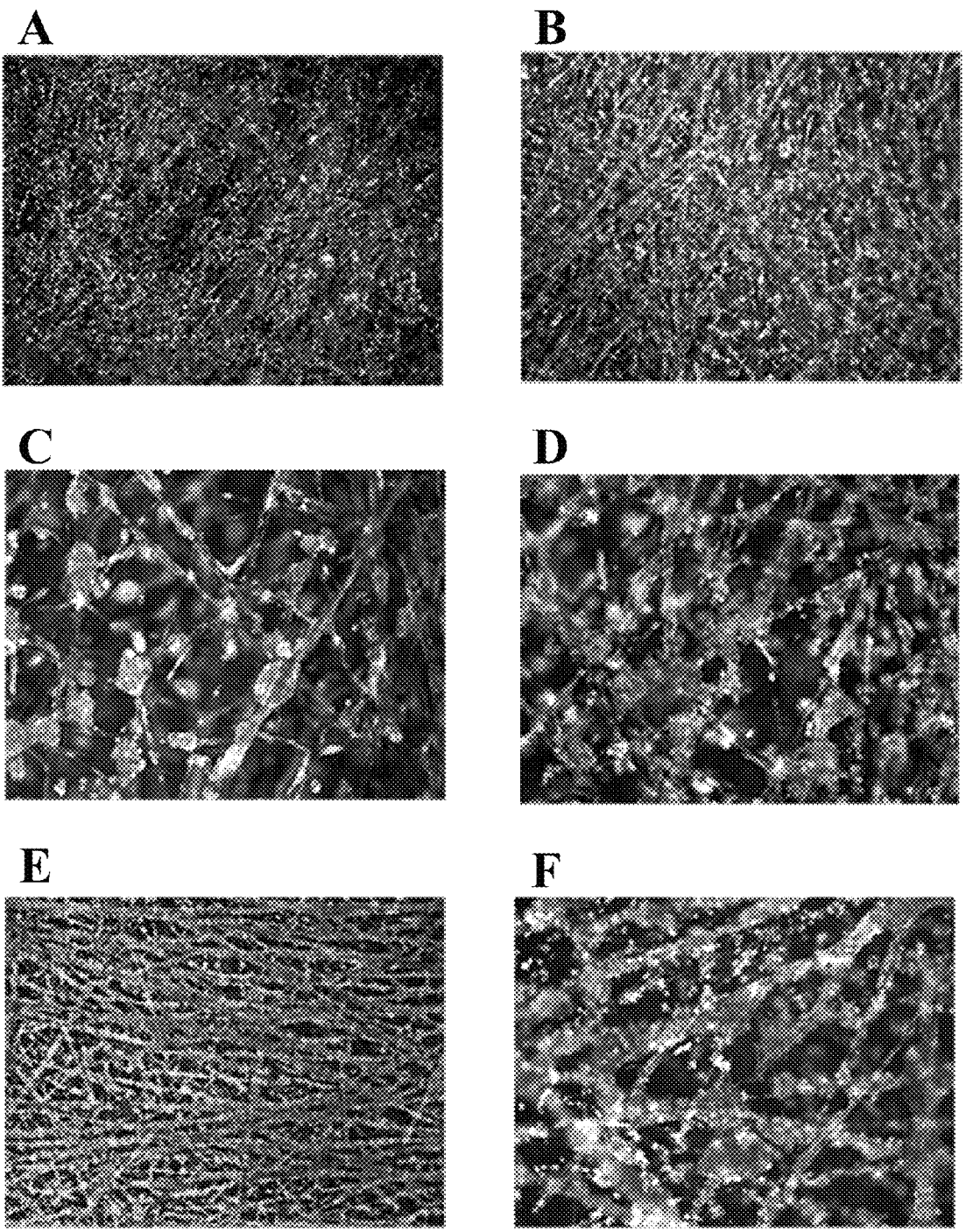
FIG. 14 contains fluorescence micrographs of Calcein AM labeled HepG2 liver cells 3D-cultured in steam-autoclaved and then PDL-coated G041 substrates.
Figure 15:
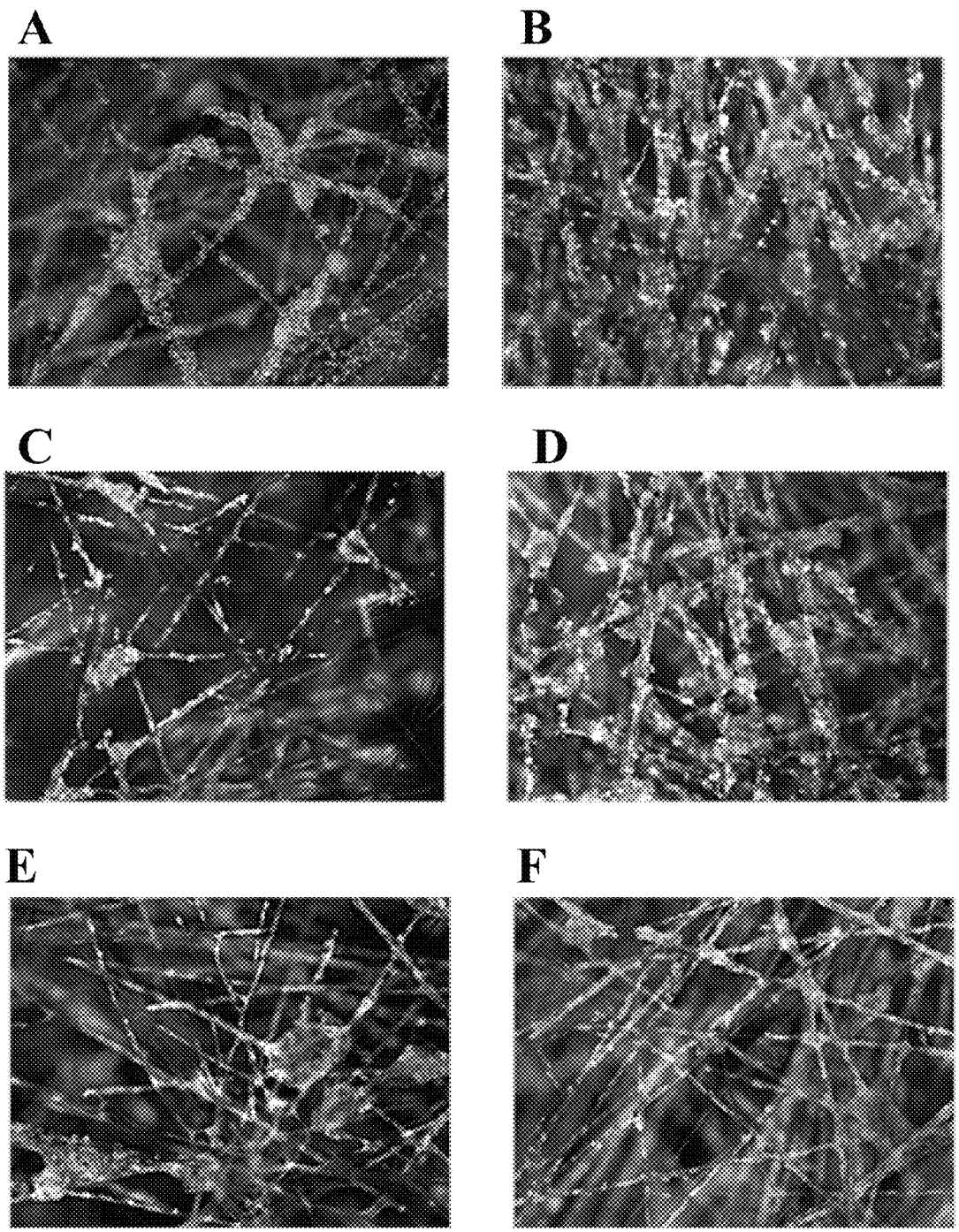
FIG. 15 contains fluorescence micrographs of Calcein AM labeled HepG2 liver cells, 3D-cultured in steam-autoclaved G041 substrates at different seeding densities.
Figure 16:
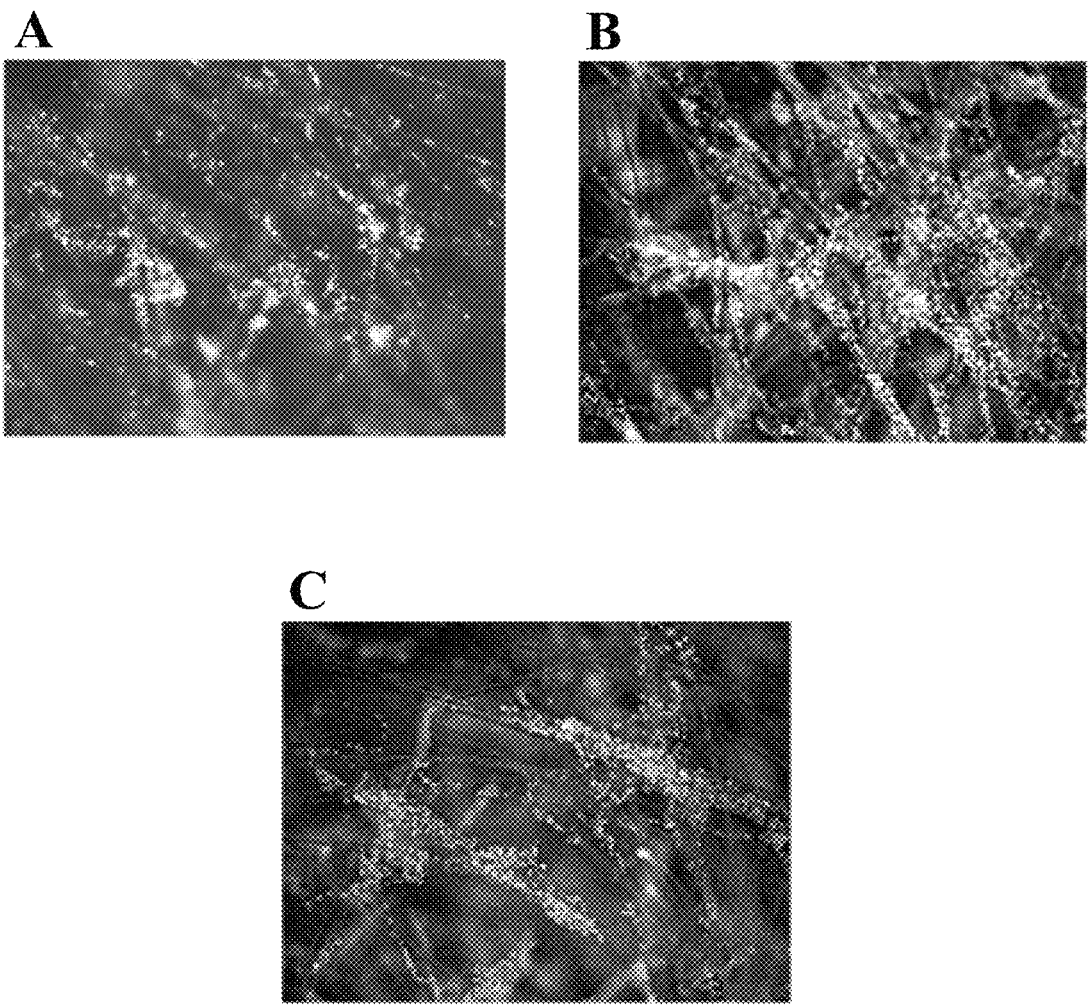
FIG. 16 contains 10× (x=1.18 mm, y=0.88 mm) fluorescence micrographs of Hoechst 33342 labeled HepG2 cells, 3D-cultured in steam-autoclaved G041 and then coated or uncoated substrates after 7 days in culture. Label A stands for 100 μg/ml Poly-D-Lysine coated substrate, label B for 1 mg/ml GFR MATRIGEL™ coated substrate and label C for uncoated substrate.
Figure 17:
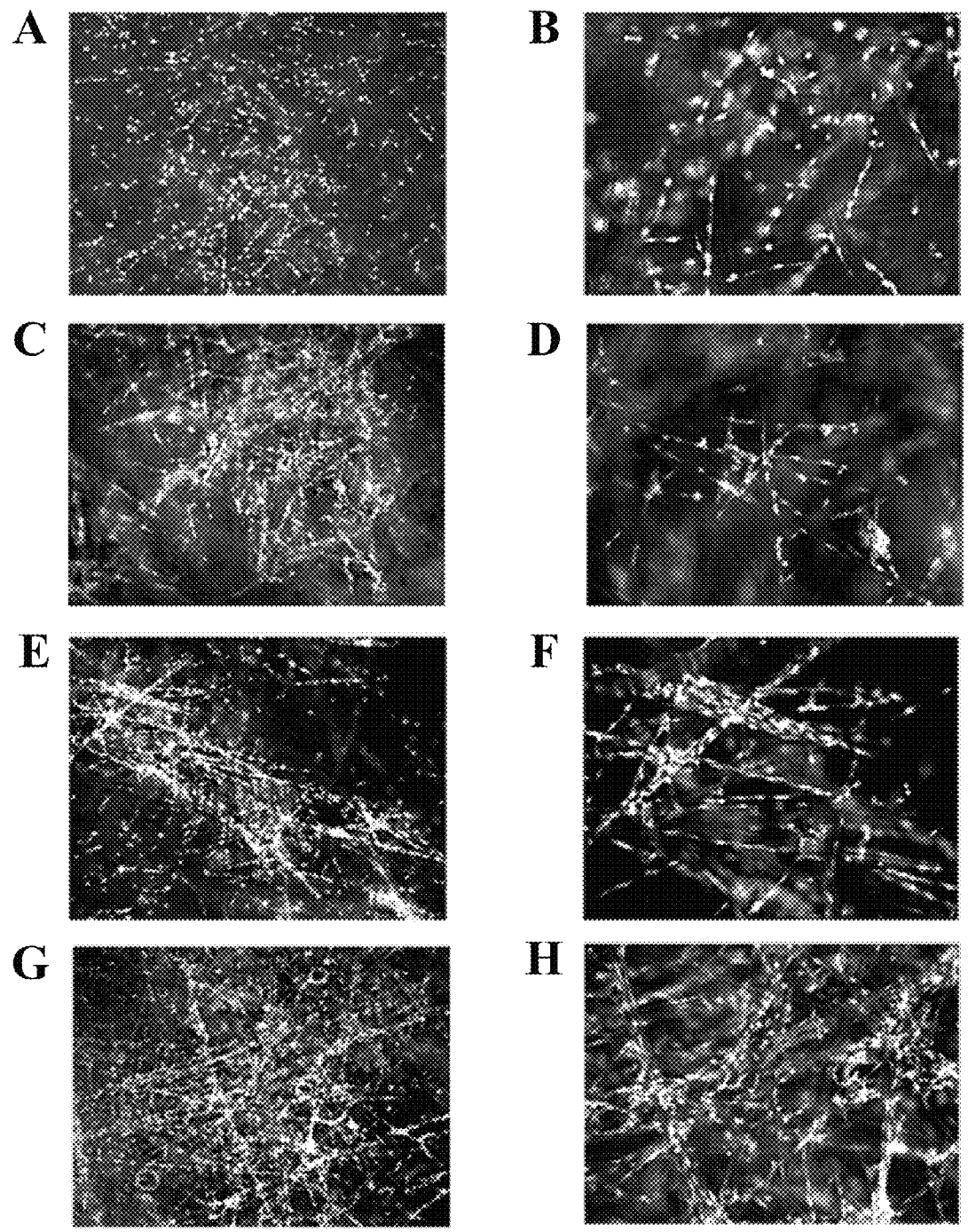
FIG. 17 shows fluorescence micrographs of Calcein AM labeled NIH 3T3 cells, 3D-cultured in steam-autoclaved G041 substrates after 7 days (FIGS. 17A-17B), 21 days (FIGS. 17C-17D), 28 days (FIGS. 17E-17F) and 35 days (FIGS. 17G-17H) in culture.
Figure 18:
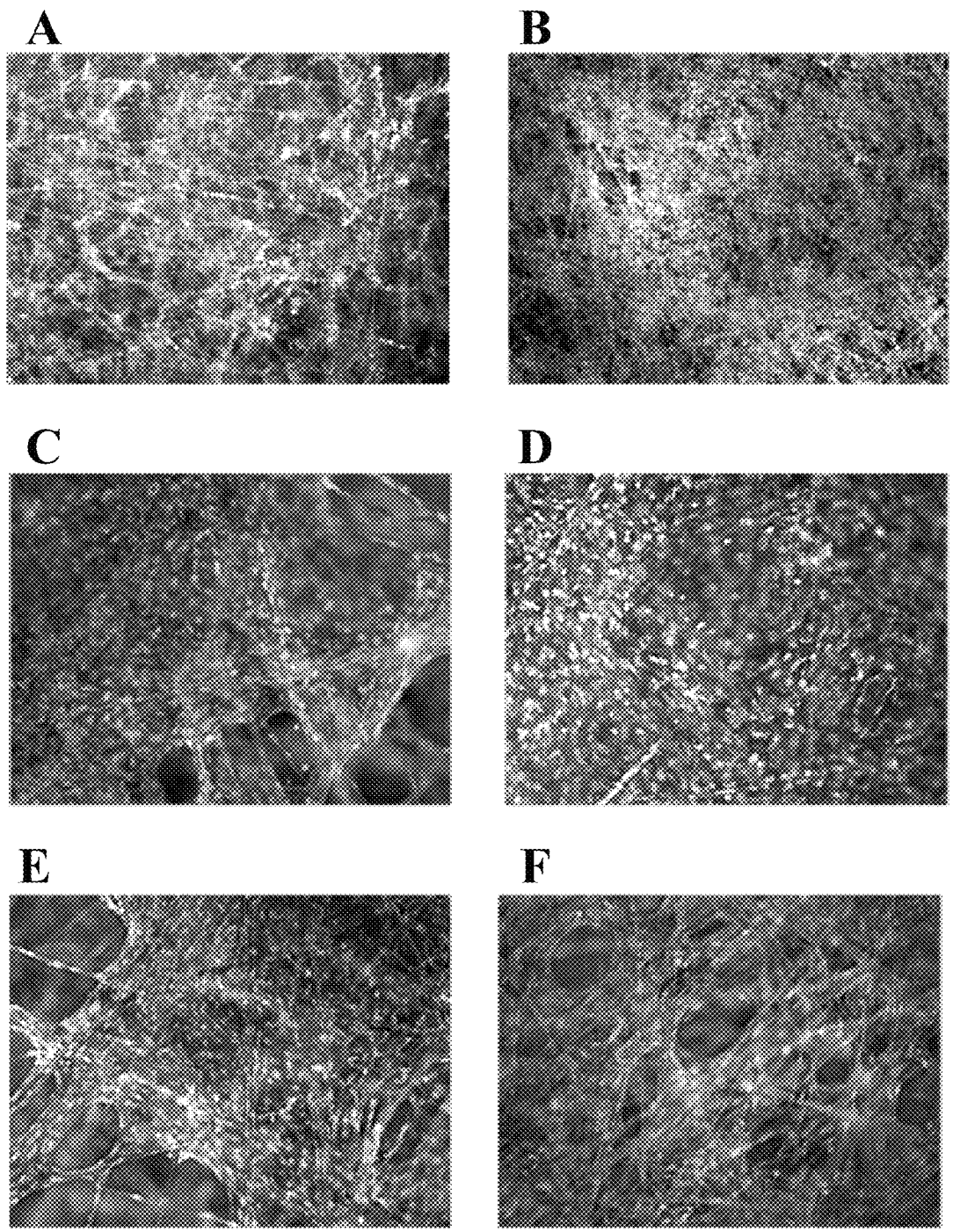
FIG. 18 contains fluorescence micrographs of Calcein AM or X-Rhodamine-1 AM and Hoecst 33342 labeled MC3T3-E1 cells, 3D-cultured in steam-autoclaved G041 substrates. The matrix was labeled by Calcein to show mineralization, if any.
Figure 19:
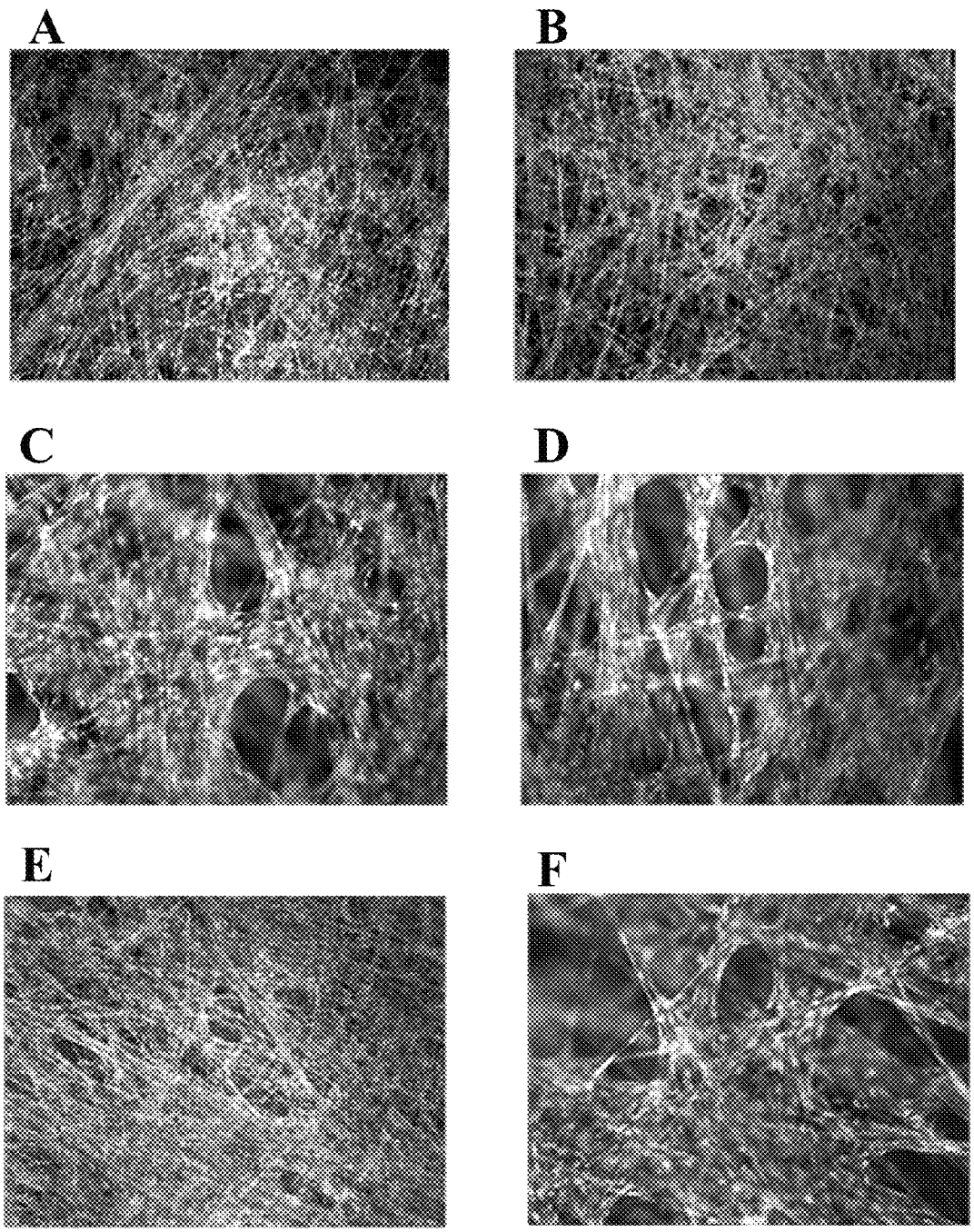
FIG. 19 contains fluorescence micrographs of Calcein AM or X-Rhodamine-1 AM and Hoecst 33342 labeled MC3T3-E1 cells, 3D-cultured in steam-autoclaved G041 substrates. The matrix was labeled by Calcein to show mineralization, if any.
Figure 20:
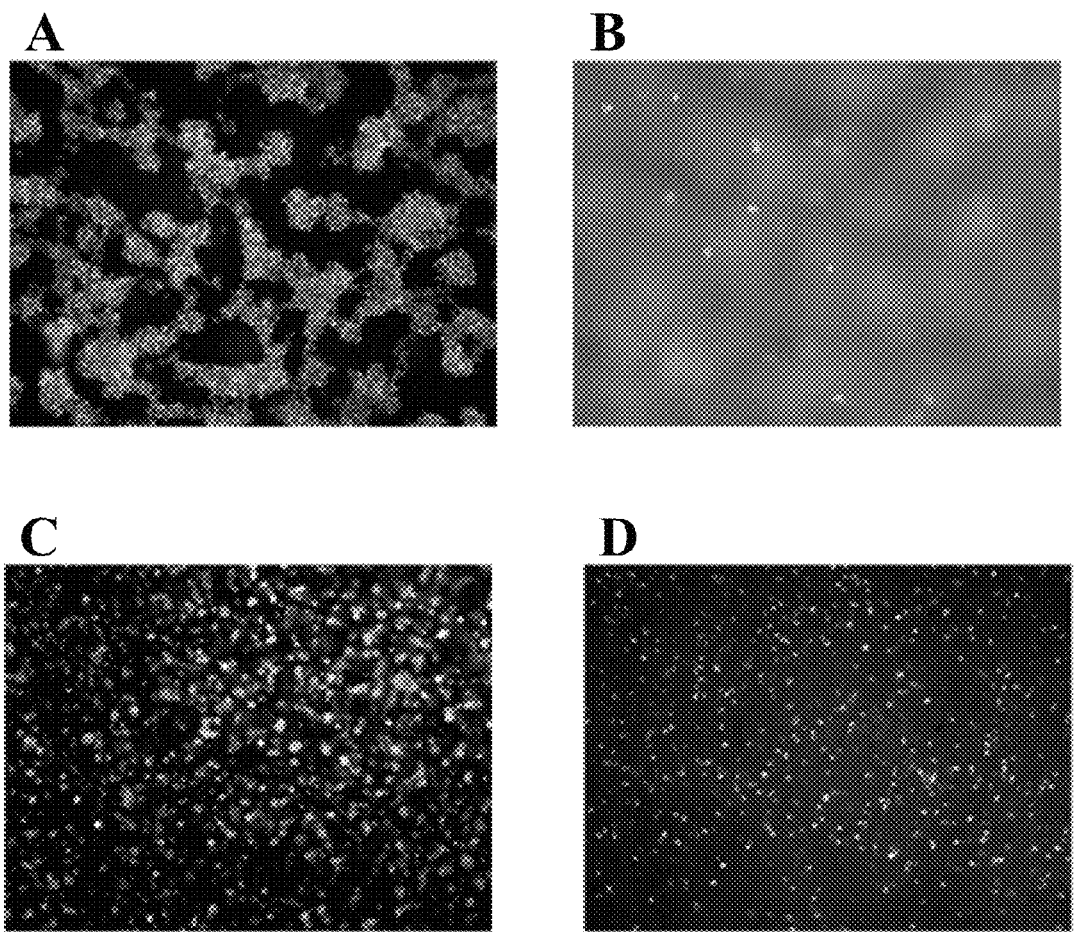
FIG. 20 contains fluorescence micrographs of Hoechst 33342 labeled HepG2 cells, seeded at $5 \times 10^5$ cells in 3.75 mg/ml GFR MATRIGEL™ and imaged after 3 days in culture.

Mixed cultures of E-18 primary cortical neurons and P0-harvested and passaged astrocytes (passage 4-8) were seeded at $2.5 \times 10^6$ cells/ml in 30 µl volume in 8 mg/ml GFR MATRIGEL™ into uncoated substrates and cultured in the wells of a 12-well plate. The medium was Neurobasal+2% B27+1% G5+0.5 mM Glutamax+1% Antibiotic/Antimycotic. Cultures were fed every 2 days by complete medium replacement. FIGS. 11A-11C show confocal micrographs of three representative cultures imaged after 10 days in culture. MATRIGEL™ was stained by Calcein Blue to confirm its presence and cells were stained using live/dead Calcein AM/EthD-1 assay.

Brain Culture #7.

In these cultures, delivery and culturing conditions were the same as with the Brain Culture #6 with the exception that cells were seeded into PDL-coated substrates. FIGS. 11D-11F show confocal micrographs of three representative cultures stained and imaged after 10 days in culture using the same dyes and imaging methods as with the Brain Culture #6.

Example 10

Liver 3D Cell Cultures

Liver 3D cell cultures were cultured in 9.5 mm in diameter substrates punched out of Millipore G041 glass fiber conjugate pad. The substrates were sterilized by steam autoclaving at 126° C. for 45 minutes prior to use with cells. For all cultures, human liver hepatocellular carcinoma cell line HepG2 (ATCC® HB-8065™) was used as a suitable in vitro model of polarized human hepatocytes. The cells were seeded using spot-an-ingredient method and cultured in uncoated-, MATRIGEL™-coated, Collagen-coated, and PDL-coated substrates, with or without gelled GFR MATRIGEL™ in a humidified 5% $CO_2$ 37° C. incubator. The substrates were seated into a 24-well plate. Cultures were fed every other day by exchanging approximately half the medium. The medium composition was MEM (+) L-Glutamine+1% MEM NEAA+ 1% Sodium Pyruvate+10% FBS. The first 3 medium components were Life Technologies #11095-072, #11140-050 and #11360-070. At the end of culturing, cultures were stained by Calcein AM, which intracellularly labeled live cells, and Hoechst 33342, which labeled nuclei of all cells blue. Culture viability at any time of imaging and for all cultures was greater than 90%. The following culturing conditions were tested:

| Liver Culture | Number of cells and the volume of cell suspension delivered to substrates at seeding | Suspension in which cells were seeded and whether it formed gel. "(*)" indicates suspension formed a gel. | Substrate coating | Fig. |
|---|---|---|---|---|
| #1 | $5 \times 10^5$ cells in 50 µl | 3.75 mg/ml GFR MATRIGEL™ (*) | PDL 100 µg/ml Sigma P7405 | 17 |
| #2 | $5 \times 10^5$ cells in 50 µl | 3.75 mg/ml GFR MATRIGEL™ (*) | none | 18A-18B |
| #3 | $5 \times 10^5$ cells in 50 µl | 1 mg/ml GFR MATRIGEL™ | none | 18C-18D |

-continued

| Liver Culture | Number of cells and the volume of cell suspension delivered to substrates at seeding | Suspension in which cells were seeded and whether it formed gel. "(*)" indicates suspension formed a gel. | Substrate coating | Fig. |
|---|---|---|---|---|
| #4 | $5 \times 10^5$ cells in 50 μl | Culture medium | PDL 100 μg/ml, P7405 | 19 |
| #5 | $10^6$ cells in 50 μl | Culture medium | PDL 100 μg/ml, P7405 | 19 |
| #6 | $2 \times 10^6$ cells in 50 μl | Culture medium | none | 20 |
| #7 | $10^6$ cells in 50 μl | Culture medium | none | 20 |
| #8 | $5 \times 10^5$ cells in 50 μl | Culture medium | none | 20 |
| #9 | $2.5 \times 10^5$ cells in 50 μl | Culture medium | none | 20 |
| #10 | $1.25 \times 10^5$ cells in 50 μl | Culture medium | none | 20 |
| #11 | $1.5 \times 10^5$ cells in 50 μl | Culture medium | Collagen I, calf skin, 1 mg/ml Sigma C8919 | 21 |
| #12 | $1.5 \times 10^5$ cells in 50 μl | Culture medium | GFR MATRIGEL™ 1 mg/ml | 21 |
| #13 | $1.5 \times 10^5$ cells in 50 μl | Culture medium | none | 21 |

Calcein AM stained liver cells are shown in FIGS. 12-26. The plane of imaging was about 50-200 μm from the culture top. For all cultures, during the first four days and up to 1 week in culture, cultures comprised a large population of 3D hepato-aggregates such as "hepatospheres" and "hepatograpes." For all conditions, the number of cells in spheroids at a given time in culture depended on how well cells were dissociated prior to seeding, i.e., whether suspension had single cells or a mixture of single cells and clusters of cells. These aggregates continued to grow and started to merge between 5-30 days in culture, ultimately forming engineered liver tissue constructs.

Example 11

3D Cell Cultures of Connective Tissues

For all cultures, standard mouse embryonic fibroblast cell line NIH 3T3 (ATCC® CRL-1658™) was used with 9.5 mm in diameter substrates punched out of Millipore G041 glass fiber conjugate pad (Material A in Example 3). The cells were seeded into steam-autoclaved (126° C. for 45 minutes) substrates, at $2 \times 10^5$ cells per substrate, using spot-an-ingredient method and cultured in a 24-well plate in a humidified 5% $CO_2$ 37° C. incubator. Cultures were fed every 3 days by exchanging all medium. The medium was DMEM (high glucose) (Life Technologies #11965-092)+10% newborn calf serum (NBCS)+1% Pen/Strep. At the end of culturing, cultures were stained by Calcein AM, which intracellularly labeled live cells, and Hoechst 33342, which labeled nuclei of all cells blue. Culture viability at any time of imaging and for all cultures was 85-90% or higher. FIGS. 17A-17H shows Calcein AM labeled cells after 7, 21, 28, and 35 days in culture.

Example 12

3D Cell Cultures of Bone Forming Cells 3D cell cultures of bone forming cells were cultured in 9.5 mm in diameter substrates punched out of Millipore G041 glass fiber conjugate pad (Material A in Example 3). The substrates were sterilized by steam autoclaving at 126° C. for 45 minutes prior to use with cells. MC3T3-E1 mouse osteoblastic cell line was used. The cells were seeded into uncoated, PDL-coated (Sigma-Aldrich P7405 at 100 μg/ml in DI water) and Fibronectin-coated (Sigma-Aldrich F-1141 at 20 μg/ml in DI water) substrates, at $1.5 \times 10^5$ cells per substrate, using spot-an-ingredient method and cultured in a 24-well plate in a humidified 5% $CO_2$ 37° C. incubator. Cultures were fed every 2-3 days by complete medium exchange. The medium was Alpha MEM (with GlutaMax) (Life Technologies 32571-036)+10% FBS+1% Pen/Strep without osteogenic supplements other than L-ascorbic acid present in Alpha MEM. At the end of culturing, all cultures were stained by Calcein AM or X-Rhodamine-1 AM (live cells) and Hoechst 33342, which labeled nuclei of all cells blue. Calcein was used for staining and detection of matrix mineralization, if any. Culture viability at any time of imaging and for all cultures was 90% or higher. Cultures cultured in PDL-coated and Fibronectin-coated substrates are shown in FIGS. 18A-18F and those cultured in uncoated substrates in FIGS. 19A-19F after up to 8 weeks in culture. This point demonstrated that cultures residing in the substrate could be handled using sterile tweezers, stained and imaged after 8 weeks in culture.

Example 13

Superiority of 3D MATRIGEL™ Cultures Embedded in the Substrate Versus MATRIGEL™ Control Cultures 3D cell cultures in MATRIGEL™ are one of the most commonly used 3D culture models. However, seeding cells in ice-cold MATRIGEL™ yielded uneven z-distribution of cells because cells settled before MATRIGEL™ gelled (cultures were normally transferred to incubator after seeding to speed up gelling). Accordingly, under 5-10 cell layer thick cultures were formed in MATRIGEL™ which were no longer considered 3D. FIGS. 20A-20D demonstrate this point by showing Hoechst 33342 labeled HepG2 3D cultures in 3.75 MATRIGEL™ seeded, cultured and imaged under identical conditions without (FIGS. 20A-20B) and with autoclaved G041 substrate (FIGS. 20C-20D). FIG. 20A shows labeled cells at gel base in a MATRIGEL™ control. FIG. 20B is the same culture imaged at a distance of about 100 μm above the gel base. As can be seen, few cells were present in planes above the culture base. In contrast, cells seeded under identical conditions but into the substrate formed spheroids 3D-distributed throughout the full substrate thickness as shown in FIG. 20C (top of the substrate) and FIG. 20D (bottom of the substrate). This shows that the substrate formed 3D cultures, rather than a few cell-layer-thick cultures with 3.75 mg/ml GFR MATRIGEL™ cell suspension at seeding.

Figure 2:
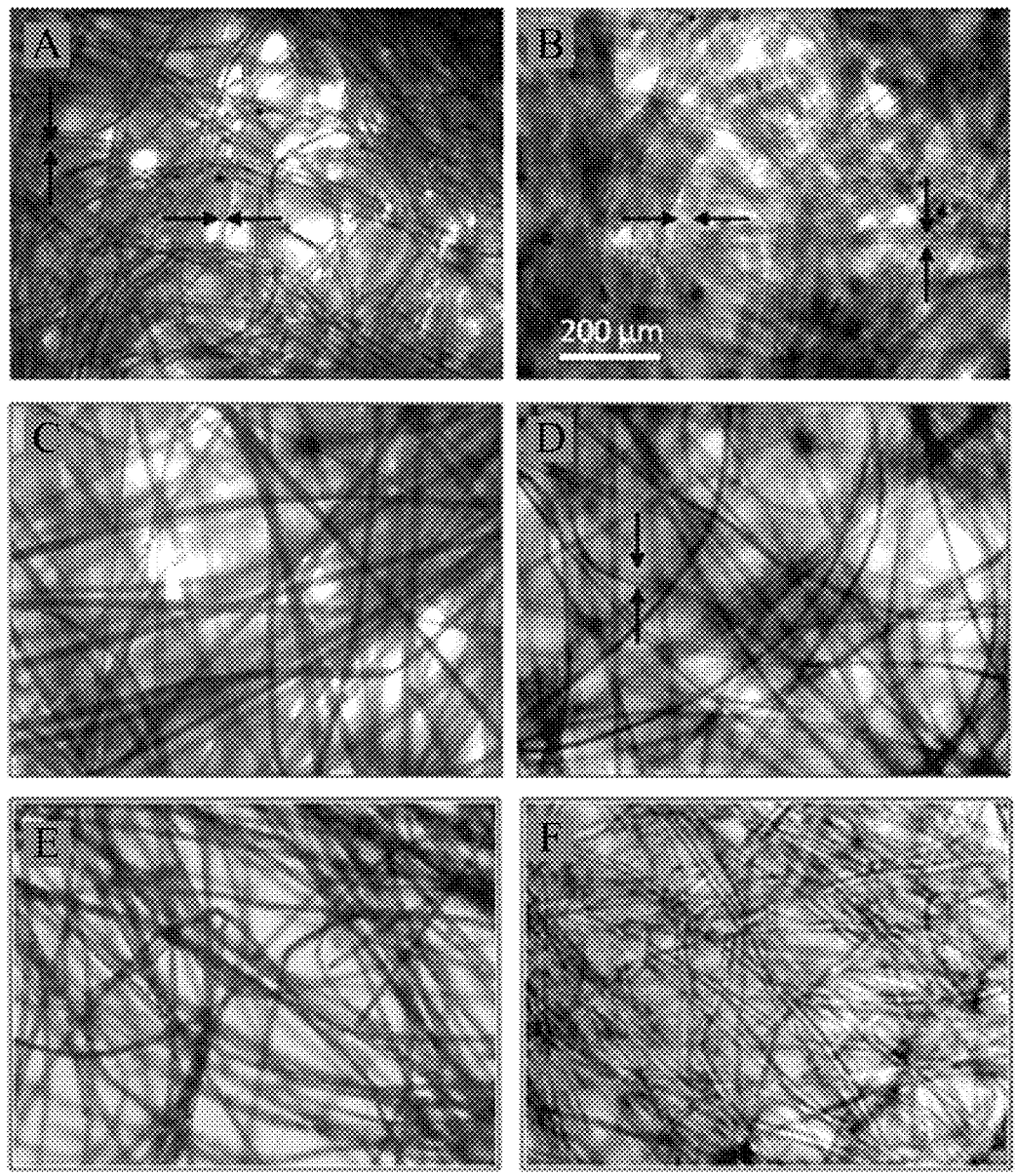
FIG. 2 contains photographs of rigid absorbent substrates in dry (A, C, E) and wet state (B, D, F) of the following composition: (A, B) VPB 105-2 polyvinyl alcohol fiber, (C, D) 50% VPB 102-5 polyvinyl alcohol fibers and 50% PVOH-coated glass fiber and (E, F) a 2:1 ratio of PVOH-coated glass fibers and fibrillated lyocel (cellulose) fiber. All images were taken at 10× in bright field (x=980 µm, y=735 µm).
Figure 21F:
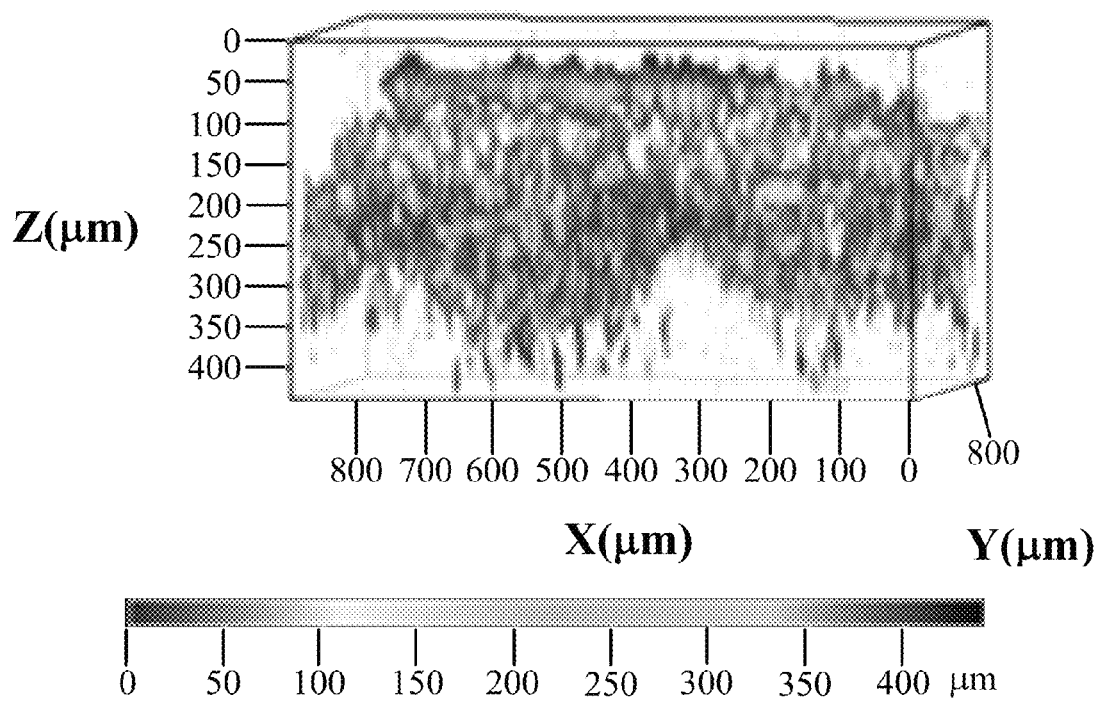
Figure 21G:
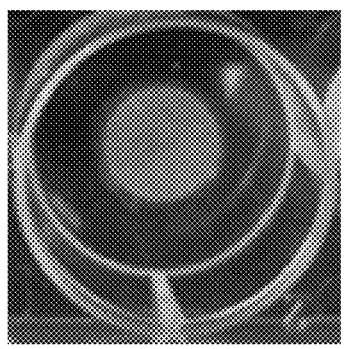
Figure 21H:
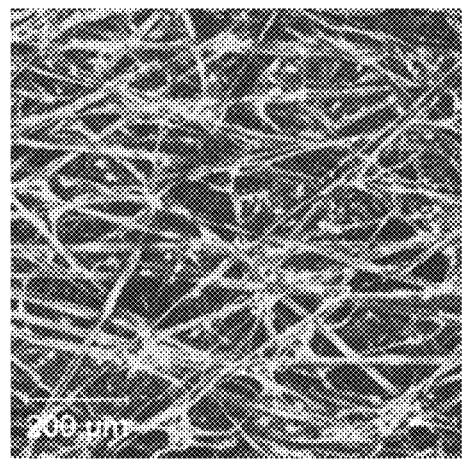
Figure 21I:
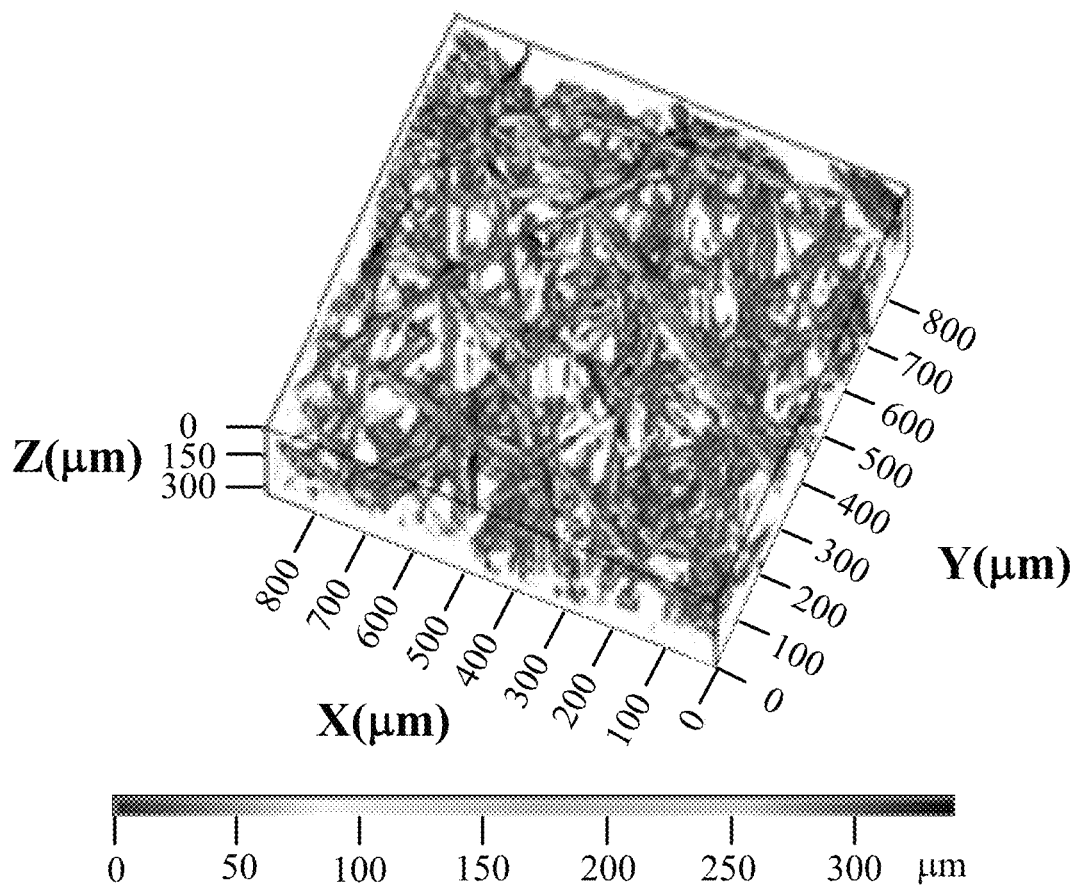
Figure 22:
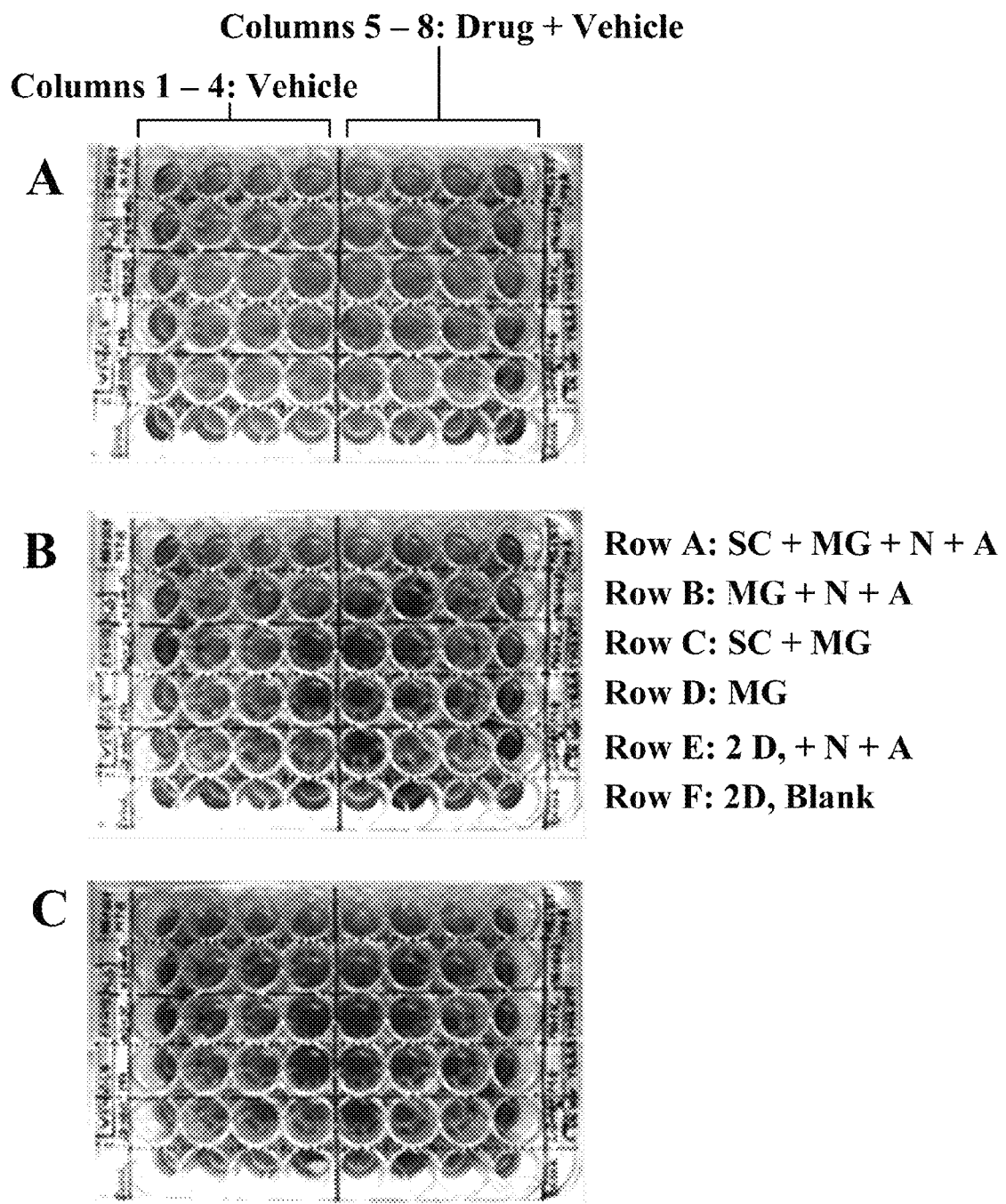
FIG. 22 contains photographs of a 48-well plate comprising 3D cell cultures, 2D cultures and their respective controls after 10 days in culture+72 hours of drug+vehicle treatment and the respective vehicle-treated controls.

Increasing MATRIGEL™ concentration from 3.75 mg/ml to 8 mg/ml contributed to faster MATRIGEL™ gelling (normally done by transferring cultures to incubator after seeding). Still, cells were more uniformly distributed in the z-direction if seeded in MATRIGEL™ in the substrate than in MATRIGEL™ controls (FIGS. 21A-21I). Next, although MATRIGEL™ control cultures were imaged near the vertical culture axis where the gel thickness was greater than the substrate thickness, cell spread in z-direction (FIG. 21C) was less than that of the corresponding z-direction cell spread in MATRIGEL™ in the substrate (FIG. 21F and FIG. 21I). Next, in MATRIGEL™ controls, characteristic dimensions of plano-convex cultures differed; culture diameter at base and culture height varied among 4 replicates. In contrast, cultures seeded in MATRIGEL™ in the substrates, whether uncoated (FIG. 2B) or PDL-coated (FIG. 2C), were contained and fully spread within the interior of substrates, which reproducibly defined culture dimensions at seeding. This is significant because variations in culture dimensions, and cell distribution across these dimensions, influenced cell function and network formation contributing to gel culture variability if no substrate was used.

Another problem with MATRIGEL™ cultures was frequent culture aspiration in routine media exchanges due to poor gel adhesion to plastic surface in long-term culture. In general, with these cell types, planar 2D cultures (even with PDL coating) and MATRIGEL™ 3D cultures all had adhesion problems, peeled off, and were even aspirated after a couple of weeks in culture. In contrast, gel cell cultures embedded in the substrate could not be aspirated after weeks in culture and were therefore superior. Next, substrates were of sufficient "wet strength" to routinely handle cultures using tweezers after 10 days and weeks in culture, while the gel cultures were difficult to transfer and sometimes disintegrated with such handling.

FIG. 21 also shows functional differences among cultures as 3D cell networks were more developed, and cell processes longer and more spread in MATRIGEL™ cultures grown in substrates than in MATRIGEL™ controls. This was associated with differences in the extracellular environment between the gel cultures and the gel cultures in the substrate. For example, substrate composition (and embedded gel composition) dictated mechanical and chemical stimuli presented to cells in culture. Exemplary mechanical stimuli were stiffness and/or rigidity of materials comprising the substrate and the embedded gel. Exemplary chemical stimuli were coatings or reagents absorbed by the absorbent component of the substrate or the embedded gel, in addition to coatings applied to fibers at the time of manufacture. Accordingly, the substrate provided for a method to cater to the needs of different cell types, wherein one or more cell type preferred stiffer materials such as glass, and one or more cell types preferred less stiff materials (like PVOH), and one or more cell types preferred soft material as was MATRIGEL™ to grow in and on. Next, intra-culture availability of soluble factors was generally different between gel cultures and gel cultures in the substrate due to different permeability to mass transport of the mass transport permeable substrate component (PVOH) and the embedded gel. All these mechanical and chemical stimuli influenced cell morphology, cytoskeletal organization, motility, migration, cell distribution, metabolism, survival, growth, differentiation, and proliferation, among other cell and cell network functions.

Taken together, substrate in conjunction with any coating or embedded gel provided for a cell culture model which could be better controlled and manipulated to model specific tissue, in health or disease, or at different age, for example, by using higher glass content in the substrate or higher protein concentration MATRIGEL™ to model stiffening extracellular environment with age.

Example 14

Demonstration of Higher Metabolic Activity in 3D Cell Cultures than in 2D Culture Controls for Drug Toxicity Testing UV-sterilized G041 material disks, 9.5 mm in diameter, were packaged in a standard 48-well plate, and used for drug toxicity testing in brain cell cultures. 10 mM Acetaminophen was incubated with cells after 10 days in culture, for 72 hours. Cytotoxicity was assessed after drug withdrawal and 4 days post-drug withdrawal using ALAMARBLUE™ assay in a high-throughput screening process. Results were compared among several culture models including (A) 2D cultures, (B) 3D cultures in MATRIGEL™, and (C) 3D cultures in MATRIGEL™ in the substrate. The term "two-dimensional culture" (2D culture) refers to one layer of cells. The following abbreviations were used: N=E-18 primary cortical neurons; A=P0-harvested and passaged astrocytes; 2D=two-dimensional cell culture; 3D=three-dimensional cell culture; PDL=Poly-D-Lysine; MG=8 mg/ml GFR MATRIGEL™; SC=UV-sterilized G041 material disk of 9.5 mm in diameter; APAP=Acetaminophen (MW=151 g/mol); DMSO=Dimethyl Sulfoxide; SD=Standard Deviation.

Cell Seeding and Culturing.

Neural-astrocytic co-cultures at 1:1 cell ratio and cell density of 62,500 cells/well were seeded in (A) 2D in Poly-D-Lysine coated wells; (B) in 3D in MATRIGEL™; and (C) in 3D in MATRIGEL™ into the substrates. In 2D, the plating was done by dispensing cells in 25 µl droplet of medium per well. In 3D, cells were dispensed in 25 µl of sol-state 8 mg/ml MATRIGEL™ droplet per well (3D MATRIGEL™ control) and into the substrate (3D culture). After seeding, the 48-well plate comprising 2D cultures, 3D MATRIGEL™ controls and 3D cultures was placed in a 5% $CO_2$ 37° C. incubator for 30 minutes for MATRIGEL™ to gel. Next, 500 µl of media was added to each well. Thereafter, subsequent media change was done every other day. During 10-day culturing, the medium was Neurobasal+2% B27+1% G5+0.5 mM Glutamax+1% Antibiotic/Antimycotic. The medium during and post-drug and vehicle treatment was Neurobasal+1% B27+0.5 mM Glutamax+1% Antibiotic/Antimycotic.

Culturing Caveats.

Care needed to be taken during media changes to not peel or accidentally aspirate 3D MATRIGEL™ controls and 2D cultures, especially those which spread to the well periphery. Therefore, during media exchanges only 50% of the media was removed per well, and replaced with 60% media (10% more to account for evaporative losses).

Drug/Vehicle Treatment and ALAMARBLUE™ Assay.

Vehicle Controls=0.2% DMSO in medium. Drug Treatment=10 mM AAP+0.2% DMSO. After 10 days in culture all incumbent media was removed and cultures treated. The plate was then placed into the 5% $CO_2$ 37° C. incubator for 72-hour incubation. The assay was done after drug withdrawal. 50 µl of ALAMARBLUE™ solution was added to the well and incubated for 5 hours. Fluorescence of cell-metabolized ALAMARBLUE™ product red fluorescing Resorufin was read in situ and after transfer of solutions (400 µl per well) to corresponding wells of another 48-well plate by Biotek Synergy H4 Hybrid Plate Reader at Ex 565 nm±9 nm and Em 585 nm±9 nm. After reads, ALAMARBLUE™ solution in media was removed and all cultures rinsed gently with HBSS, followed by addition of fresh medium (without vehicle or drug) for another 4-day-long culturing. Medium was not replaced during this period as 2D cultures and 3D MATRIGEL™ controls were prone to peeling and aspiration after 10 days in culture, and especially after drug and vehicle treatment.

Experimental Layout.

| Blank 2-D No cells | 2-D N + A 62,500 cells/well | MG No cells | SC + MG No cells | MG + N + A 2,500 cells/mm$^3$ 62,500 cells/well | MG + SC + N + A 2,500 cells/mm$^3$ 62,500 cells/well |
|---|---|---|---|---|---|
| Controls 4 | Controls 4 | Controls 4 | Controls 4 | Controls 4 | Controls 4 |
| Drug Treatment 4 | Drug Treatment 4 | Drug Treatment 4 | Drug Treatment 4 | Drug Treatment 4 | Drug Treatment 4 |

Results.

Figure 23:
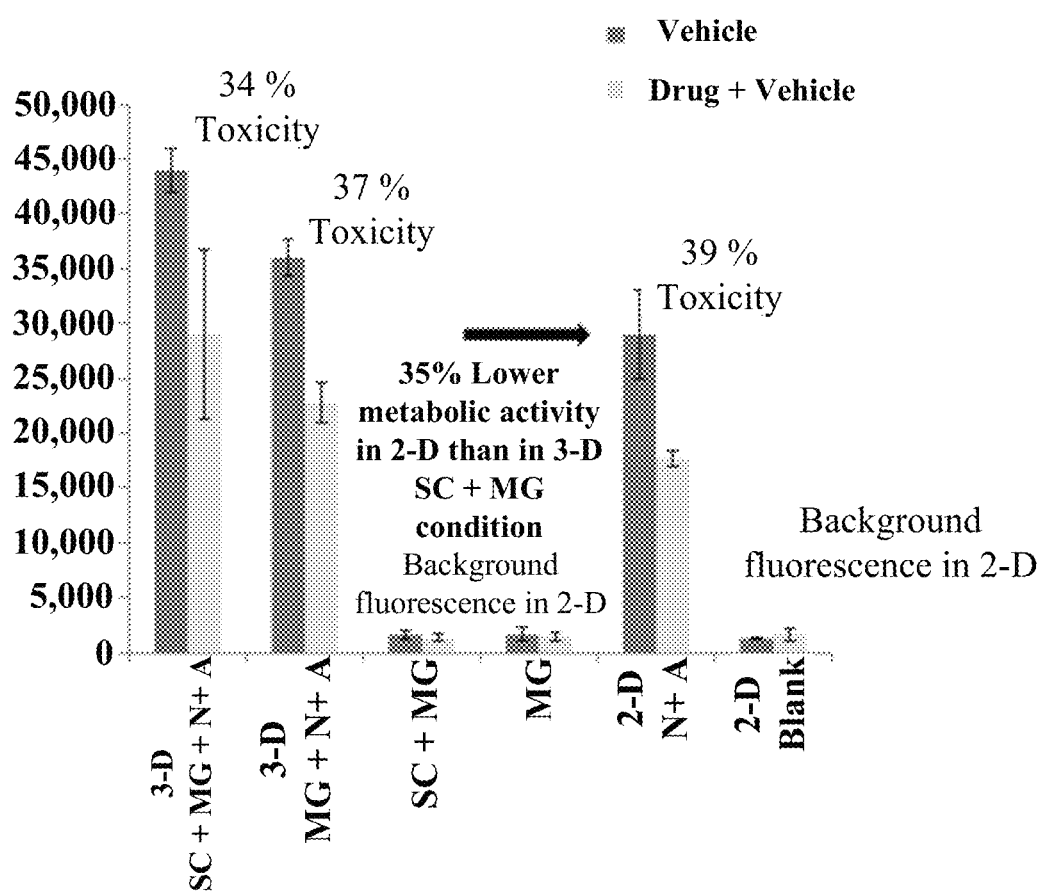
FIG. 23 shows a graph of ALAMARBLUE™ assay mean±SD fluorescence read taken in a 48-plate into which ALAMARBLUE™ solutions were transferred to after Acetaminophen cytotoxicity study. The abbreviations on the graph are: N=E-18 primary cortical neurons; A=P0-harvested and passaged astrocytes; 2D=two-dimensional cell culture; 3D=three-dimensional cell culture; PDL=Poly-D-Lysine; MG=8 mg/ml GFR MATRIGEL™; SC=UV-sterilized G041 material disk of 9.5 mm in diameter; APAP=10 mM Acetaminophen (MW=151 g/mol); DMSO=Dimethyl Sulfoxide; SD=Standard Deviation.

FIG. 22A shows a 48-well plate after 10 days in culture+72 hour vehicle (controls) and drug (drug+vehicle) treatment, and right after delivery of ALAMARBLUE™ in media. As seen in color, all wells were blue because cells did not have time to reduce ALAMARBLUE™ (Resazurin, blue) to Resorufin (red). FIG. 22B shows the plate after 5-hour incubation in ALAMARBLUE™ solution. As seen in color, culture columns in the left side of the plate (Vehicle controls) were more red than Drug Treated cultures (right side of the plate). As Vehicle controls were not exposed to toxic drug dose, they had a higher number of live and metabolically active cells, which converted blue Resazurin to red Resorufin. FIG. 22C shows a photograph of the 48-well plate into which ALAMARBLUE™ solutions were transferred to from corresponding wells shown in FIG. 22B. The readings from this plate are shown in FIG. 23. The reads showed that drug dose was toxic and that 3D culture controls were generally healthier than 2D control cultures, indicating that cells survived better in 3D than in 2D culturing conditions, an important quality for drug screens in matured and developed cell networks. Plate reads were also done 4 days after drug withdrawal. However, by that time, results were more difficult to compare because all cultures without substrates had adhesion problems and when cells failed to adhere, they died, which could be mistakenly attributed to drug cytotoxicity. In sum, 3D MATRIGEL™ cultures in the substrates were healthier and metabolically more active, and therefore more suitable for drug testing than were their corresponding 2D culture counterparts.

Example 15

Substrate Integration into Multi-Well Plates and Multi-Well Insert Systems

For materials in the Examples 2-4, substrates had been punched or cut by scissors into any shape, sterilized and then inserted or integrated into any disposable cellware or culture ware whether commercial or custom.

Figure 24:
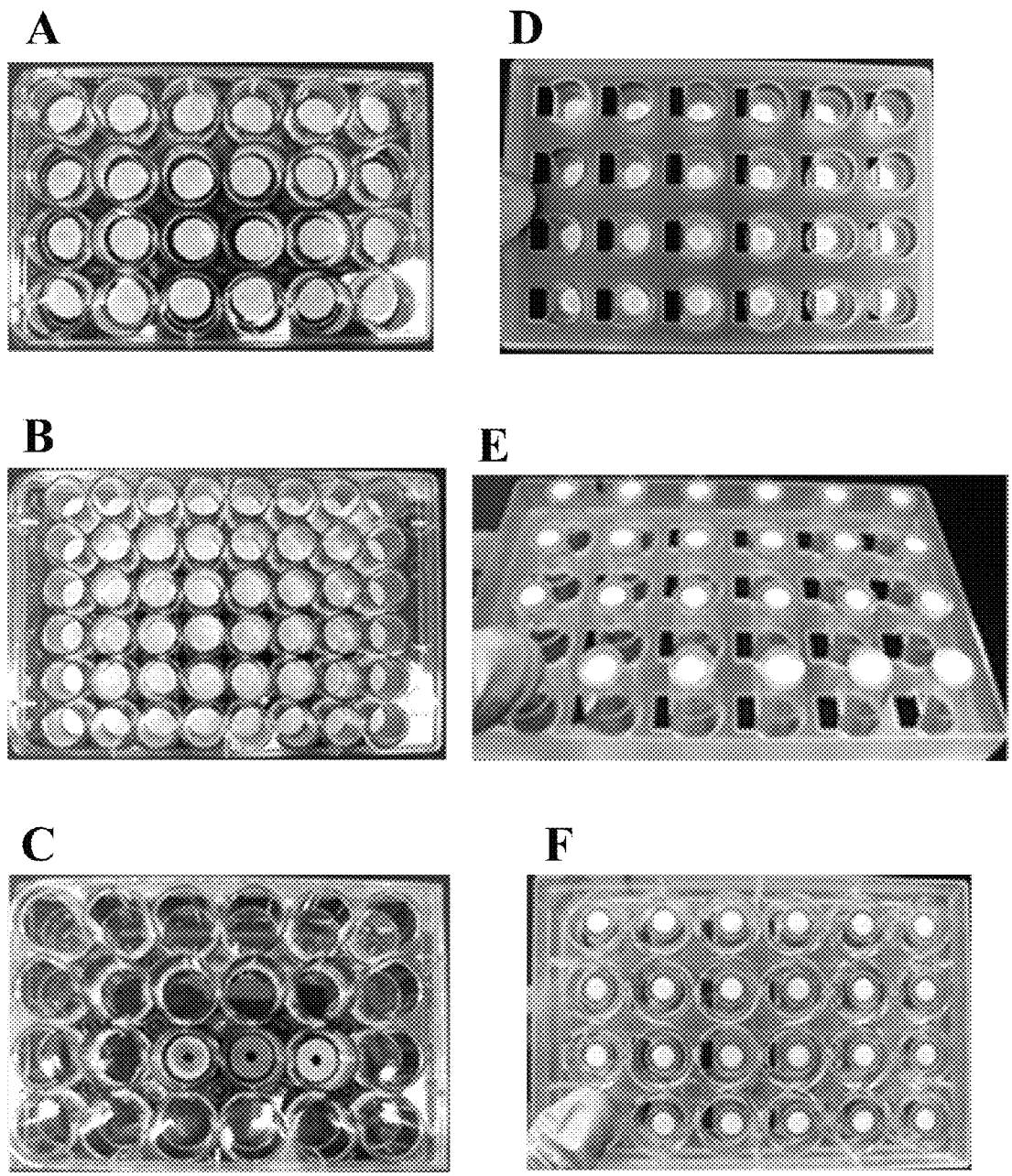
FIG. 24 contains photographs of substrates cut into different shapes and integrated into standard multi-well plates (FIGS. 24A-24C) and multi-well insert systems (FIGS. 24D-24F).
Figure 25:
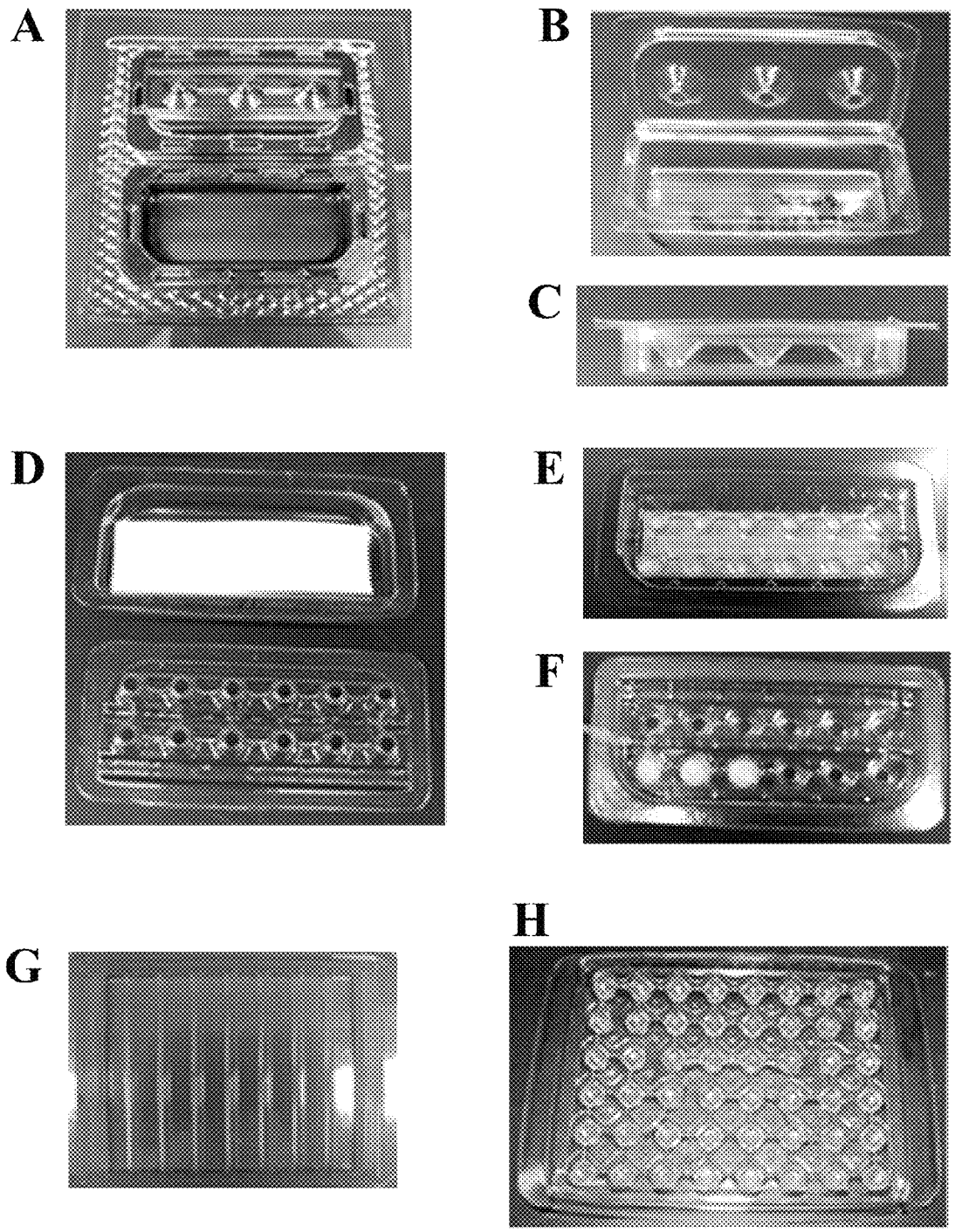
FIGS. 25A-25H contain photographs of custom fabricated multi-well plates and multi-well insert systems and substrates cut into different shapes and integrated into them.

In Examples 5-7 substrates were seated into Petri dishes. In FIG. 24 substrates were seated or integrated into high-throughput disposables such as multi-well plates (FIGS. 24A-24C) and multi-well inserts (FIGS. 24D-24F) and used as components of multi-well insert systems (FIG. 24F). In FIG. 24A there was one substrate per well of a 24-well plate. In FIG. 24B there were 2 substrates per well of a 48-well plate. In FIG. 24C substrates were cut in a ring shape and seated in some wells of a 24-well plate. In FIGS. 24D-24E substrates were integrated (one per well) into an integral multi-well insert and then seated into a multi-well plate (FIG. 24F). To integrate substrates into inserts, off-the-shelf inserts with membranes were used. Openings were made in membranes such that substrates cut into disks of appropriate diameter could be snugly seated on membrane disks. The fit was tight and substrates could not come off. In another method, membranes were punched out and the insert was dipped into the PVOH solution, slightly cured, followed by the attachment of substrate disks to wells, followed by insert placement under the platen of a "wide mouth" T-shirt heat press for a 2-hour-long cure at 50° C., after which a strong bond was formed between the substrates and respective wells of the insert.

Next, substrates were inserted or integrated into custom disposables. An example of such a disposable is shown prior to being separated from the mold in FIG. 25A. It was fabricated using standard manufacturing using a mold and a vacuum former. A similar 3-well disposable made using this approach is shown in FIGS. 25B-25C in two views. A custom 12-well insert system comprising a 12-well insert and a receiving tray seating a substrate strip is shown in FIG. 25D without the lid. FIGS. 25E-25F show that substrates may be integrated into the wells of the insert or seated as a strip or other shape in a receiving tray. Receiving trays may be in the form of a plurality of reservoirs as shown in FIG. 25G, wherein each reservoir accepts at least one substrate strip or any other substrate shape; or in the form of a custom multi-well plate (FIG. 25H), wherein each well seated at least one substrate.

In general, by disclosed fabrication method all substrates may be integrated into the inserts and seated into reservoirs of any shape and form, such that each reservoir accepts at least one substrate in the insert; or all substrates can be integrated into the insert; or at least one substrate may be integrated into the insert and at least one substrate may be integrated into at least one reservoir in the tray. The spacing between the bottom of the insert well and the base of the receiving reservoir was adjustable by the disclosed fabrication method and may have been present (for example, when substrates were attached to insert) or not present.

Any biocompatible method known in the art may be used to bond substrates to plastic disposables such as ultrasonic sealing, RF sealing, heat sealing, chemical bonding, etc. These methods are normally used for attachment of membranes to inserts in commercial multi-well insert systems. For custom plates and inserts, the following additional methods were used to bond substrates to plastic: (A) corona treatment of substrates and plastic; (B) coating of plastic by Dow Corning Sylgard 184 (a 10:1 ratio of thoroughly mixed pre-cursor to cross-linking agent), followed by 45 minute drying, followed by placement of substrates on partly-cured Sylgard, followed by 48-hour room temperature cure; (C) coating of plastic by 1%-10% water solution of PVOH Sigma-Aldrich #363103), followed by 30 minute drying in the hood, followed by placement of substrates on partly cured polymer, followed by 2-day room temperature cure with or without pressure; and (D) use of ring-shape punched double sided tape TESA part #4965, etc., except for Corona treatment which did not ensure good attachment (at least under energy tested), all other tested methods were successful. With all methods care was taken that bonding materials were partly cured before substrates were attached to them (to prevent wicking).

Example 16

Superiority of Substrates for Generation of Gradients and their Maintenance

For materials in the Examples 2-4, substrates were punched or cut into shapes, sterilized and used to setup gradients of one or more ingredients. In some tests, gradients were further applied to cells in culture. In other tests, suspension of uncultured cells was suspended inside the substrate to which a gradient was applied. Chemotaxis of human neutrophils suspended inside G041 substrate to which a gradient of Interleukin 8 was applied was recorded in a 45-minute video.

Figure 26:
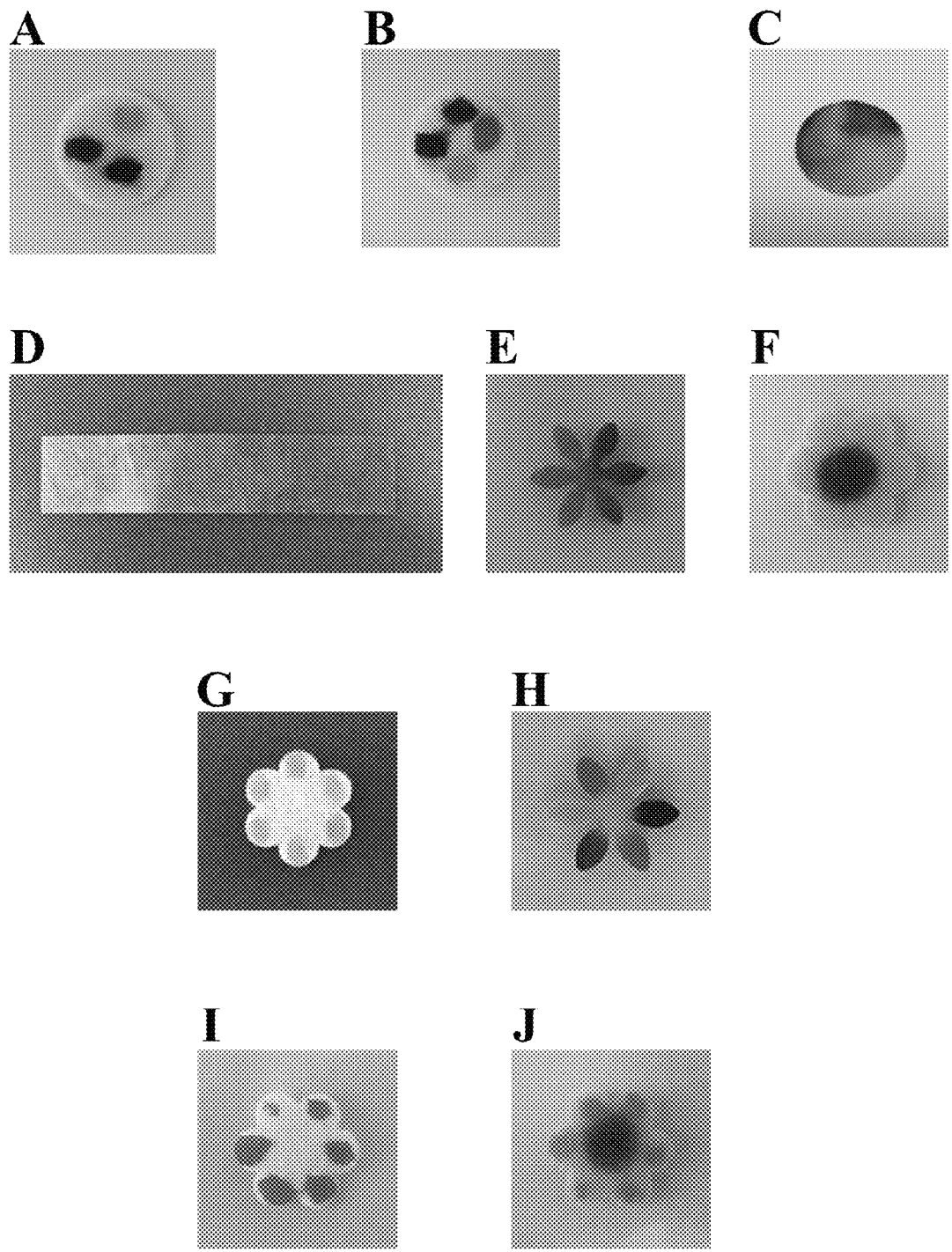
FIGS. 26A-26J contain photographs of substrates containing gradients of one or more molecules. Substrates were cut into different shapes and gradients formed by spotting molecules side-by-side, by wicking, or by the combination of spotting and wicking.

FIG. 26 shows substrates with gradients formed using one or more of the following dye solutions: yellow—fluorescein, blue—Methylene Blue, brown and red—Ateco Spectrum Chocolate Brown and Super Red gel food color, respectively. In FIG. 26A, 5 µl of blue, brown and yellow dye was spotted. In FIG. 26B additional 5 µl of red dye was spotted after 2 minutes. This formed steep gradients of molecules in unsaturated substrate. Next, 40 µl of HBSS was added and the substrate saturated. All four dyes diffused and formed a smoother gradient (FIG. 26C). In FIG. 26D, gradient was formed by wicking yellow and red dye, one of each, on the opposite sides of the substrate. In FIG. 26E, the substrate was dipped into red dye until it was uniformly stained. Next, tips of 3 petals were dipped into the brown dye. Petals wicked brown dye and formed a gradient. In FIG. 26F, the substrate was dipped into yellow dye until it was uniformly stained. Next, 20 µl of brown dye was spotted near the center and the gradient was formed. In FIG. 26G 5 µl of yellow dye was spotted to each substrate lobe. In FIG. 26H 1 µl, 2 µl, 3 µl, 4 µl, 5 µl and 6 µl of red dye was spotted, one per lobe, to each lobe. Smoother gradients were formed by addition of 40 µl of HBSS to the center of the substrate. In FIG. 26I yellow, red, blue and brown dyes were spotted, a dye per petal, to saturate the petals. Next, DI water was delivered at the center to form a gradient. In FIG. 26J, the substrate was dipped into yellow dye until it was uniformly stained. Next, 1 µl, 2 µl, 3 µl, 4 µl, 5 µl and 6 µl of red dye was spotted, one per lobe, to each lobe, followed by spotting of brown dye near the center.

FIG. 26 shows some of the methods used to spot and/or wick and/or dip ingredients, including cell cultures, or cell suspensions, into the one or more substrates to form gradients and to test them with the cells in culture or with the cells in suspension (suspended within the interior of the substrate). Tested ingredients were cell suspensions, gels and polymers, drugs (e.g Methylene Blue), dyes, culture media, buffers (e.g. HBSS), excipients and pharmaceutical ingredients used in drug dose formulations, oral and other forms or drug delivery (e.g. Carbopol). Notably, any other suitable molecule; active or inactive biologicals; biomaterials, polymers or test compounds which could be wicked by the substrate could have been used. All or some ingredients were either applied to one substrate or to a plurality of substrates which were further partly or wholly overlapped or placed side-by-side so as to have at least one point of contact.

As shown in Example 9 (Brain Culture #5) cells survived without free (substrate-unbound) medium, if overlapped by another substrate with the embedded medium. Accordingly, molecule diffusion studies, and this included gradients formed in one or more substrates, were maintained for longer periods of time without significant gradient "dilution" (by otherwise present surrounding pool of medium) when applied to cells in culture (or to uncultured cells suspended inside the substrate) by way of a substrate overlap method. In short term studies in a humidified incubator, neutrophils were exposed to a gradient inside the substrate, and the substrate was not overlapped by another substrate, yet a significant fraction of cells taxed in a suitable gradient.

The invention claimed is:
1. A three-dimensional cell culture scaffold composition comprising a rigid absorbent component, and a gel, wherein
   a. the rigid absorbent component is hydrophilic, comprises between approximately 70% and 95% w/w insoluble borosilicate glass fibers having an absorbent polymer coating, has a void volume of between approximately 70% and 95%, which void volume comprises the gel; and
   b. the gel is
      a composition comprising Laminin, Collagen IV, Entactin, and heparin sulfate proteoglycan at a total protein concentration of between 3.75 and 16 mg/ml.
2. The composition of claim 1, wherein the glass fibers have a diameter between approximately 5 and 30 µm.
3. The composition of claim 1, wherein the absorbent coating is poly vinyl alcohol.
4. The composition of claim 1, wherein the void volume is between approximately 85-95%.
5. The composition of claim 1, wherein the void volume further comprises one or more eukaryotic cells.
6. The composition of claim 5, wherein the eukaryotic cell is a human or animal cell.

* * * * *